US006995008B1

(12) United States Patent
Liu et al.

(10) Patent No.: US 6,995,008 B1
(45) Date of Patent: Feb. 7, 2006

(54) COORDINATE IN VIVO GENE EXPRESSION

(75) Inventors: Margaret A. Liu, Rosemont, PA (US); John W. Shiver, Doylestown, PA (US); Helen C. Perry, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/393,803

(22) Filed: Sep. 10, 1999

Related U.S. Application Data

(63) Continuation of application No. 08/702,502, filed as application No. PCT/US95/02633 on Mar. 3, 1995, now abandoned, which is a continuation-in-part of application No. 08/207,525, filed on Mar. 7, 1994, now abandoned.

(51) Int. Cl.
*C12N 15/63* (2006.01)
*C12N 15/64* (2006.01)
*C12N 15/85* (2006.01)
*C12N 15/867* (2006.01)

(52) U.S. Cl. ................. 435/320.1; 536/23.1; 536/23.5; 536/23.72; 536/24.1

(58) Field of Classification Search .................. 514/44; 536/23.1, 24.1; 435/320.1, 6, 455, 7.1; 530/387.1; 424/130.1
See application file for complete search history.

(56) References Cited

U.S. PATENT DOCUMENTS

| | | | | |
|---|---|---|---|---|
| 3,931,397 | A | 1/1976 | Harnden | 514/44 |
| 4,124,702 | A | 11/1978 | Lampson et al. | 514/44 |
| 4,224,404 | A | 9/1980 | Viza et al. | 435/2 |
| 4,394,448 | A | 7/1983 | Szoka, Jr. et al. | 435/458 |
| 4,396,601 | A | 8/1983 | Salser et al. | 424/94.5 |
| 4,405,712 | A | 9/1983 | Vande Woude et al. | 435/5 |
| 4,689,320 | A | 8/1987 | Kaji | 514/44 |
| 4,806,463 | A | 2/1989 | Goodchild et al. | 430/604 |
| 4,897,355 | A | 1/1990 | Eppstein et al. | 424/450 |
| 4,937,190 | A | 6/1990 | Palmenberg et al. | 525/193 |
| 4,946,787 | A | 8/1990 | Eppstein et al. | 264/4.1 |
| 5,036,006 | A | 7/1991 | Sanford et al. | 435/459 |
| 5,049,386 | A | 9/1991 | Eppstein et al. | 424/427 |
| 5,168,062 | A | 12/1992 | Stinski | 435/366 |
| 5,208,036 | A | 5/1993 | Eppstein et al. | 424/450 |
| 5,256,553 | A | 10/1993 | Overell | 435/456 |
| 5,298,422 | A | 3/1994 | Schwartz et al. | 435/320.1 |
| 5,674,703 | A * | 10/1997 | Woo et al. | 435/69.1 |
| 5,736,524 | A * | 4/1998 | Content et al. | 514/44 |
| 5,861,290 | A * | 1/1999 | Goldsmith et al. | 435/456 |
| 5,866,553 | A * | 2/1999 | Donnelly et al. | 514/44 |
| 6,107,062 | A * | 8/2000 | Hu et al. | 435/91.41 |
| 6,228,844 | B1 * | 5/2001 | Wolff et al. | 514/44 |

FOREIGN PATENT DOCUMENTS

| | | | |
|---|---|---|---|
| EP | 0 187 702 A1 | 7/1986 | |
| EP | 0 187 702 B1 | 7/1986 | |
| EP | 0 585 983 A2 | 7/1993 | |
| WO | WO 86/00930 | 2/1986 | |
| WO | WO 90/01543 | 2/1990 | |
| WO | WO 90/11092 | 10/1990 | |
| WO | WO 91/00359 | 1/1991 | |
| WO | WO 91/07487 | 5/1991 | |
| WO | WO 91/16024 | 10/1991 | |
| WO | WO 91/17424 | 11/1991 | |
| WO | WO 93/03143 | 2/1993 | |
| WO | WO 93/03709 | 3/1993 | |
| WO | WO 93/11250 | 6/1993 | |
| WO | WO 93/12240 | 6/1993 | |
| WO | WO93/12756 | 7/1993 | |
| WO | WO 93/17706 | 9/1993 | |
| WO | WO 93/20212 | 10/1993 | |
| WO | WO 93/19768 | 11/1993 | |
| WO | WO93/11250 | * 12/1993 | 435/69.1 |
| WO | WO 93/24640 | 12/1993 | |
| WO | WO 94/04196 | 3/1994 | |

OTHER PUBLICATIONS

Haynes, Scientific and Social Issues of HIV . . . , Science vol. 260, pp. 1279-1285, May 1993.*
Schwartz et al, Expression of HIV-1 vif and vpr mRNAs is REV dependent . . . , vol. 183, pp.677-86, Aug. 1991.*
Smarda et al, Dicistronic selection for nuclear proteins in living animal cells, Gene vol. 137, pp.145-149, Dec. 1993.*
Ulmer et al., Heterologous Protection against Influenza by injection of DNA encoding a viral protein, Science vol. 259, 1745-49, Mar. 1993.*
Petit, "Antibodies That Fight AIDS Can Also Incite It, Report Says", San Francisco Chronicle, (Dec. 15, 1993).
Robinson et al., Protection Against a Lethal Influenza Virus Challenge by Immunization with a Haemagglutinin-Epxressing Plasmid DNA, Vac., vol. 11, Issue 9, pp. 957-960 (1993).
Petricciani, "Global Immunization Against AIDS, Economic Considerations", Vac., vol. 11, Issue 8, pp. 873-877 (1993).
Burke, et al., "Vaccine Therapy for HIV: A Historical Review of the Treatment of Infectous Diseases by Active Specific Immunization . . . ", Vac., vol. 11, Issue 9, pp. 883-891 (1990).

(Continued)

*Primary Examiner*—David Guzo
(74) *Attorney, Agent, or Firm*—J. Mark Hand; Jack L. Tribble

(57) ABSTRACT

Nucleic acids, including DNA constructs and RNA transcripts, capable of inducing coordinate expression of two to three cistrons upon direct introduction into animal tissues, are bi- or tri-cistronic polynucleotides of this invention include those encoding and co-expressing HIV gene products, genes encoding antigens unrelated to HIV, and immunostimulatory gene products, including but not limited to GM-CSF, interleukins, interferon and members of the B7 family of proteins which act as T-cell costimulatory elements. The methods and polynucleotides of this invention are generally applicable to co-ordinate expression in vivo of any two or more genes in a single cell.

12 Claims, 29 Drawing Sheets

OTHER PUBLICATIONS

Troni, et al., "HIV-1 Gag Mutants Can Dominantly Interfere with the Replication of the Wild-Type Virus", Cell, vol. 59, pp. 113-120 (Oct. 6, 1989).

Kobayashi, et al., "Identification and Purification of Natural Killer Cell Stimulatory Factor (NKSF), A Cytokine with Multiple Biologic . . . ", J. Exp. Med., vol. 170, pp. 827-845 (Sep. 1989).

Stern, et al., "Purification to Homogeneity and Partial Characterization of Cytotoxic Lymphocyte Maturation Factor from Human B-Lymphoblastoid Cells", Proc. Natl. Acad. Sci., Imm., vol. 87, pp. 6808-6812 (Sep. 1990).

Afonso, et al., "Adjuvant Effect of Interleukin-12 in a Vaccine Against Leishmania major", Sci., vol. 263, pp. 235-237, (Jan. 14, 1994).

Townsend & Allison, "Tumor Rejection After Direct Stimulation of $CD8^+$ T Cells by B7-Transfected Melanoma Cells", Sci., vol. 259, pp. 368-270 (Jan. 15, 1993).

Gimmi, et al., "B-cell surfact antigen B7 provides a costimulatory signal that induces T cells to proliferate and secrete interleukin 2", Proc. Natl. Acad. Sci. USA, Imm., vol. 88, pp. 6575-6579 (Aug. 1991).

Freeman, et al., "B7, A New Member of the Ig Superfamily with Unique Expression on Activated and Neoplastic B Cells", J. Immunology, vol. 143, pp. 2714-2722, No. 8, (Oct. 15, 1989).

Edginiton, "Turning On Tumor-Fighting T-Cells", Bio/Tech., vol. 11, pp. 1117-1119 (Nov. 10, 1993).

Calin-Laurens, et al., "Can one predict antigenic peptides for MHC class I-restricted cytotoxic T lymphocytes useful for vaccination?", Vac., vol. 11, Issue 9, pp. 944-978.

Eriksson, et al., "Systematic identification of T-cell activating epotopes on the human immunodeficieicy virus type 1 envelope glcoprotein gp120 in primates immunized with synthetic peptides", Vac., vol. 11, Issue 8, pp. 859-8865.

Berzofsky, et al., "Construction of Peptides Encompassing Multideterminant Clusters of Human Immunodeficiency Virus Envelope to Induce in Vitro T Cell", J. Clin. Inves., Inc., vol. 88, pp. 876-884 (Sep. 1991).

Choppin, et al., "HLA-Binding Regions of HIV-1 Proteins", J. Immunology, vol. 147, No. 2, pp. 575-583 (Jul. 15, 1991).

Choppin, et al., "HLA_Binding Regions of HIV-1 Proteins", J. Innunology, vol. 147, No. 2, pp. 569-574 (Jul. 15, 1991).

Tsuliyama, et al., "Internal Ribosome Entry Site within Hepatitis C Virus RNA", J. Virology, vol. 66, No. 3, pp. 1476-1483 (Mar. 1992).

Shirai, et al., "Broad Recongnition of Cytotoxic T Cell Epitopes from the HIV-1 Envelope Protein with Multiple Class I Histocompatibility . . . ", J. Immunology, vol. 148, No. 6, pp. 1657-1667 (Mar. 15, 1992).

Gheysen, et al., "Assembly and Release of HIV-1 Precursor Pr55gag virus-like Particles from Recombinant Baculovirus-Infected Insect Cells", Cell, vol. 59, pp. 103-112 (Oct. 6, 1989).

Felber, et al., "A Quantitative Assay for HIV-1 Based on Trans-Activiation", Sci., vol. 239, pp. 184-187 (Jan. 8, 1988).

Coben, "A New Goal: Preventing Disease, Not Infection", Sci., vol. 262, pp. 1820-1821 (Dec. 17, 1993).

Shafferman, et al., "Prevention of transmission of simian immunodeficiency virus from vaccinated macaques that developed transient virus infection following challenge", Vac., vol. 11, Issue 8, pp. 848-853 (1993).

Colombo, et al., "Granulocyte Colony-stimulating Factor Gene Transfer Supresses Tumorigenicity of a Murine Adenocarcinoma In Vivo", J. Exp. Med., vol. 173, pp. 889-897 (Apr. 1991).

Chan, et al., "Induction to Interferon γ Prodcution by Natural Killer Cell stimulatory Factor: Characterizationof the Responder Cells . . . ", J. Exp. Med., vol. 173, pp. 869-879 (Apr. 1991).

Philip, et al., "In Vivo Gene Delivery", J. Bio Chem., vol. 268, No. 22, pp. 16087-16090 (Aug. 5, 1993).

Novagen, pCITE™0 System Protocols, 565 Science Dr., Madison, WI 53711.

Viral Testing System Corp., Catalog showing availability of IAM 41-2F5.

Davis, et al., "DNA-based immunization induces continuous secretion of hepatitis B surface antigen and high levels of circulating antibody", J. Exp. Med., vol. 173, pp. 889-897 (Apr. 1991).

Dubensky, et al., "Direct transfection of viral and plasmid DNA into the liver or spleen of mice", Proc. Natl. Acad. Sci. USA, Genetics, vol. 81, pp. 7529-7533 (Dec. 1984).

Seeger, et al., "The cloned genome of ground squirrel hepatitis virus is infectious in the animal", Proc. Natl. Acad., Sci. USA, Med. Sci., vol. 81, pp. 5849-5852 (Dec. 1984).

Bluestone, "Genes in a Bottle", Bio/Tech., vol. 10, pp. 132-136 (Feb. 1992).

Luckow, et al., "CAT constructions with multiple unique restrictors sites for the functional analysis of eukaryotic promoters and regulatory elements", IRL Press Ltd., Oxford, England, vol. 15, pp. 5490 (1987).

Edgington, "PCR: Catching the Next Wave", Bio/Tech.,, vol. 10, pp. 137-140 (Feb. 1992).

Takahasi, et al., "Inductionof Broadly Cross-Reactive Cytotixic T Cells Recognizing an HIV-1 Envelope Determinant", Sci., vol. 255, pp. 333-336 (Jan. 17, 1992).

Yang,et al., "In vivo and in vitro gene transfer to amammalian somatic cells by particle bombardment", Proc. Natl. Acad. Sci. USA, Genetics, vol. 87, pp. 9568-9572 (Dec. 1990).

Emini, et al., Antibody-Mediated In Vitro Neutralization of Human Immunodeficiency Virus Type 1 Abolishes Infectivity for Chimpanzees, J. of Virology, vol. 64, No. 8, pp. 3674-3678 (Aug. 1990).

Characterization of Bicistronic Retroviral Vector Composed of the Swine Vesicular Disease Virus Internal Ribosome Entry Site, J. Virol., vol. 67, No. 4, pp. 2142-2148 (Apr. 1993).

Eisenbraum, et al., "Examination of Parameters Affectin the Elicitation of Humoral Immunes Responses by Particle Bomabarment-Mediated Genetic Immunizations", DNA and Cells Bio., vol. 12, No. 9, pp. 791-797 (1993).

Rankauckas, et al., "Long-Term Anti-Nucleoprotein Cellular and Humoral Immunity Is Induced by Intramuscular Injection of Plasmid DNA Containing NP Gene", DNA and Cell Bio., vol. 12, No. 9, pp. 771-776 (1993).

Cheng, et al., "In vivo promoter activity and transgene expression in mammalian somatic tissue evaluated by using particle bombardment", Proc. Natl. Sci. USA Gentics, vol. 90, pp. 4455-4459 (May 1993).

Nabel, et al., "Direct gene transfer with DNA-liposome complexes in melanoma: Expression, biologic activity, and lack of toxicity in humans", Proc. Natl. Acad. Sci. USA, Med. Sci., vol. 90, pp. 11307-11311 (Dec. 1993).

Montgomery, et al., "Heterolgous and Homologous Protection Against Influenza A by DNA Vaccination: Optimization of DNA Vectors", DNA and Cell Bio., vol. 12, No. 9, pp. 777-783 (1993).
Frynan, et al., "Use of DNA Encoding Influenza Hemagglutinin as an Avian Influenza Vaccine", DNA and Cell Bio., vol. 12, No. 9, pp. 785-789 (1993).
Kolata et al., "Once More, HIV Refuses to Play by the Rules", NY Times, (Dec. 12, 1993).
Lu, "U1 small nuclear RNA plays a direct role in the formation of a rev-regulated human immunodeficiency virus env mRNA that remains unspliced", Proc. Matl. Acad. Sci. USA, Med. Sci., vol. 87, pp. 7598-7602 (Oct. 1990).
Cohen, "Jitters Jeopardize AIDS Vaccine Trials", Sci., vol. 262, pp. 980-981 (Nov. 12, 1993).
Washington AP, The Wall Street Journal, "AIDS Vaccines fail in Laboratory Tests, Researchers Report", (Nov. 12, 1993).
Vaishav , "Impact of Tat on Cellular Functions", Ann. Rev. Biochem., vol. 60, pp. 613 (1991).
Rekosh, et al., "Coexpression of human immunodeficiency virus envelope proteins and tat froma single simian virus 40 late replacement vector", Proc. Natl. Acad. Sci. USA, Biochem., vol. 85, pp. 334-338 (Jan. 1998).
Wang et al., "Gene inoculation generates immune responses against human immunodeficiency virus type 1", Proc. Natl. Acad. Sci. USA, Immunology, vol. 90, pp. 4156-4160 (May 1993).
Zhu, et al., "Systemic Gene Expression After Intravenous DNA Delivery Into Adult Mice", Sci., vol. 261, pp. 209-211 (Jul. 9, 1993).
Kolata, Antibiotics Block HIV in Laboratory Studies, New York Times.
Wolff, et al., "Long-term persistence of plasmid DNA and foreign gene expression in mouse muscle", Human Molecular Genetics, vol. 1, No. 6, pp. 363-370 (Sep. 1992).
Davies, et al., The Sequence Context of the Initiation Codon in the Encephalomyocarditis Virus Leader Modulates Efficiency of Internal Translation Initiation:, J. Virol., vol. 66, No. 4, pp. 1924-1932 (Apr. 1992).
Ghattes, et al., "The Encephalomyocarditis Virus Internal Ribosome Site Allows Efficient Coexpression of Two Genes from a Recombinant Provirus . . . ", Mol. and Cell Biol., vol. 11, No. 12, pp. 5848-5859 (Dec. 1991).
Chang, et al., "Regulation by HIV Rev Depends Upon Recognition of Splice Sites", Cell., vol. 59, pp. 789-798 (Dec. 1, 1989).
Kaufman, et al., "Improved vectors for stable expression of foreign genes in mammalian cells by use of the untranslated leader sequence from EMC virus", Nucleic Acids Res., vol. 19, No. 16, pp. 4485-4490 (1991).
Chapman, et al., "Effect of intron A from human cytomegalovirus (Towne) immediate-early gene on heterologous expression in mammanial cells", Nucleic Acids Res., vol. 19, No. 14, pp. 3979-3986 (1991).
Dorin, et al., "Selection for Precise Chromosomal Targeting of a Dominant Marker by Homologous Recombination", Science., vol. 243, pp. 1357-1360 (Mar. 10, 1989).
Lavitrano, et al., "Sperm Cell as Vectors for Introducing Foreign DNA into Eggs: Genetic Transformation of Mice", Vell, vol. 57, pp. 717-723 (Jun. 2, 1989).
Nabel, et al., "Site-Specific Gene Expression in Vivo be Direct Gene Transfer into the Arterial Wall", Sci., vol. 249, pp. 1285-1288 (Sep. 14, 1990).
Malone, et al., "Cationic liposome-mediated RNA tranfection", Proc. Natl. Acad. Sci. UDS, Biochem., vol. 86, pp. 6077-6087 (Aug. 1989).
Soriano, et al., "Targeted and nontargeted lipsomes for in vivo transfer to rat liver cells of a plasmid containing the preproinsulin I gene", Proc. Natl. Acad. Sci. UDS, Biochem., vol. 80, pp. 7128-7131 (Dec. 1983).
Mannino, et al., "Liposome Mediated Gene Transfer", Bio/Tech., vol. 6, No. 7, pp. 682-680 (1988).
Selter, et al., "Gene Therapy Advance—Anti-HIV Antibodies Work Inside Cells", C&EN, pp. 3-4 (Aug. 16, 1993).
Nicolau, et al. "Liposomes as Carriers for in Vivo Gene Transfer and Expression", Meth. in Cnzym., vol. 149, pp. 157-177.
Schwartz, et al., "Induction of HIV-1neutralising and syncytium-inhibiting antibodies in uninfected receipients of HIV-1 IIIB rgp120", Lancet, vol. 342, pp. 69-73 (Jul. 10, 1993).
Lin, et al., "Expression of Recombinant Genes in Myocardium In Vivo After Direct Injection of DNA", Circulation, vol. 82, No. 6, pp. 2217-2221 (Dec. 1990).
Acsadi, et al., "Direct Gene Transfer and Expression into Rat Heart In Vivo", New Biologist, vol. 3, No. 1, pp. 71-81 (Jan. 1991).
Kitsis, et al., "Hormonal modulation of a gene injected into rat heart in vivo", Proc. Natl. Acad. Sci. USA, Genetics, vol. 88, pp. 4138-4142, (May 1991).
Buttrick, et al., "Behavior and Genes Directly Injected Into the Rat Heart in Vivo" Circulation Res., vol. 70, No. 1, pp. 193-198 (Jan. 1992)
Gal, et al, "Direct Myocardial Transfection in Two Animal Models", Lab. Invest., vol. 68, No. 1, pp. 18-25 (1993).
von Harsdorf, et al., "Gene Injection Into Canine Myocardium as Useful Model for Studying Gene Expression in the Heart of Large Mammals", Circulations Res., vol. 72, No. 3, pp. 688-395 (Mar. 1993).
Hansen, et al., "Strong Expression of Foreign Genes Following Direct Injection into Fish Muscle", Fed. European Biochem. Soc., vol. 290, No. 1,2 pp. 73-76 (Sep. 1991).
Jiao, et al., "Direct Gene Transfer into Nonhuman Primate Myofibers In Vivo", Human Gene Therapy, vol. 3, pp. 21-33 (1992).
Ulmer, et al., "Heterologous Protection Against Influenza by Injection of DNA Encoding a Viral Protein", Sci., vol. 259 pp. 1745-1749 (Mar. 19, 1993).
Cox, et al., "Bovine Herpesvirus 1: Immune Repsonses in Mice and Cattle Injected with Plasmid DNA"< J. Virol., vol. 67, pp. 5664-5997 (Sep. 1993).
Robinson, et al., "Modern Approaches to New Vaccines", Abs. of papers presented at 1992 meeting, Cold Spring Harbor, NY.
Freeman, et al., "Structure, Expression, and T Cell Costimulatory Activity of the Murine Homologue of the Human B Lymphocyte Activation Antigen B7", J. Exp. Med., vol. 174 , pp. 625-631 (Sep. 1991).
Cudd, et al., "Intracellular fate of liposime-encapsulated DNA in mouse liver.", Biochinica et Biophysica Acata, vol. 845, pp. 477-497 (1985).
GENEBANK Accession No. KO 3455 M38432, sequence of HIV-1 isolate of HXB2 Strain.
Abstract, 88-164720/24, Medisa Shinyaku KK, B04 D16 J6 3102-682-A.
Abstract, 89-098031/13, Vitimin Kenkyushok, B04 D16 J0 1047-381-A.

Will, et al., "Infectious hepatitis B virus from cloned DNA of known nucleotide sequence", Proc.Natl. Acad. Sci., vol. 82, pp. 891-895 (1985).
Freitelson, et al., "A Chronic Carrierlike State is Established in Nude Mice Injected with Cloned Hepatitis B Virus DNA", J. of Virol., vol. 62, No. 4, pp. 1408-1415 (1988).
Sureau, et al., "Cloned Hepatitis Delta Virys cDNA is Infectious in the Chimpanzee", J. of Virol., vol. 63, No. 10, pp. 4292-4297 (1989).
Seeger, et al., "In Vitro Recombinants of Ground Squirrel and Woodchuck Hepatitis Viral DNAs Produce Infectious Virus in Squirrels", J. of Virol., vol. 61, No. 10, pp. 3241-3247 (1987).
Sprengel, et al., "Homologous Recombination between Hepadnaviral Genomes following in Vivo DNA Transfection: Implications for Studies of Viral Infectivity", Virol., vol. 61, No. 159, pp. 454-456 (1987).
Sprengel, et al., "Cloned Duck Hepatitis B Virus DNA Is Infectious in Peking Ducks", vol. 52, No. 159, pp. 454-156 (1987).
Will, et al., "Cloned HBV DNA Causes Hepatitis in Chimpanzees", Nature, vol. 299, pp. 740-742 (1982).
Pestka, et al., "Anti-mRNA: Specific inhibition of translation of single mRNA molecules", Proc. Natl. Acad. Sci., vol. 81, pp 7525-7528 (1984).
Felgner, et al., "Cationic liposome-mediated transfection", Nature, vol. 337, No. 6205, pp. 387-388 (1989).
Brigham, et al., "Rapid Communication: In Vivo Transfection of Murine Lungs with a Functioning Prokaryotic Gene Using a Liposome Vehicle", Am. J. Med. Sci., vol. 298, pp. 278-281 (1989).
Furth, et al., "Gene Transfer into Somatic Tissues by Jet Injection", Analytical Biochem., vol. 205, pp. 365-368 (1992).
Grosse, et al., "Flow Cytofluorometric Investigation of the Uptake by Hepatocytes and Spleen Cells of Targeted and Untargeted Liposomes . . . ", Biochem. et Biophysica Acta, vol. 805, pp. 354-361 (1984).
Wu, et al., "Receptor-mediated Gene Delivery and Expression in Vivo", Bio. Chem., vol. 263, No. 29, pp. 14621-14624 (1988).
Wang, et al., "pH-sensitive immunoliposomes mediate target-cell-specific delivery and controlled expression of a foreign gene in mouse", Proc. Natl. Acad. Sci., vol. 83, pp. 7851-7855 (1987).
Nicolau, et al., "In vivo expression of rat insulin after intravenous administration of the liposime-entrapped gene for rat insulin I", Proc. Natl. Acad. Sci., vol. 83, pp. 1608-1072 (1983).
Felgner, et al., "Particulate systems and polymers for in vitro and in vivo delivery of polynucleotides", Advanced Drug Delivery Reviews, vol. 5, pp. 1-25 (1990).
Brigham, et al., "Epxression of a Prokaryotic Gene in Cultured Lung Endothelial Cells After Lopefection with a Plasmic Vector", Amer. J. Res. Cel. and Mol. Bio., vol. 1, pp. 95-100 (1989).
Holt, et al., "Lipefection of cDNAs in the Embryonic Vertebrate Central Nercous System", Neuron, vol. 4, pp. 203-214 (1990).
Tang, et al., "Genetic immunization is a simple method for eliciting an immune response", Nature, vol. 356, pp. 152-154 (1992).
Friedman, et al., "Progress Toward Human Gene Therapy", Sci. vol. 244, pp. 1275-1281 (1989).
Felgner, et al., "Lipofection: A highly efficient, lipid mediated DNA-transfection procedure", Proc. Natl. Acad. Sci., vol. 83, pp. 7413-7417 (1987).
Wolff, et al., "Direct Gene Transfer into Mouse Muscle in Vivo", Sci., vol. 247, pp. 1465-1468 (1990).
Benvenisty, et al., "Direct introduction of genes into rats and expression of the genes", Proc. Natl. Acad. Sci., vol. 83, pp. 9551-9555 (1986).
Louis, et al., "An alternative approach to somatic cell gene therapy", Proc. Natl. Acad. Sci., vol. 85, pp. 3150-3154 (1988).
Verma, "Gene Therapy", Scientific Am., pp. 68-84 (1990).
Physicians' Desk Ref., pp. 1232-1234 (1993).
Marantz-Henig, "New Vaccine Method Using DNA Protects Mice Against a Flu Virus" NY Times Med. Sci., pp. C3 (1993).
Furth, et al., Analytical Biochem., vol. 205, pp. 365-368 (1989).
Kaneda, et al., "Increased Epxression of DNA Cointroduced with Nuclear Protein in Adult Rat Liver", Sci., vol. 243, pp. 375-378 (1989).
Gammelin, et al., "Two Subtypes of Nucleoproteins (NP) of Influenza A Viruses", Virol., vol. 170, pp. 71-80 (1989).
Townsend, et al., "Antigen Recognition by Class I-Restricted T Lymphocytes", Ann. Rev. Immunol., vol. 7, pp. 601-624 (1989).
de Wet, et al., "Firefly Luciferase Gene: Structure and Epxression in Mammalian Cells", Molec. and Cell Biol., vol. 7, No. 2, pp. 725-737 (1987).
Johnston, "Biolistic Transformation: Microbes to Mice", Nature, vol. .46, pp. 776 (1990).
Germain, et al., "The ins and outs of antigen processing and presentation", Nature, vol. 322, pp. 687-689 (1986).
Lichtenstein, et al., "Transgenic cereals by direct injection of DNA into plants", Nature, vol. 325, pp. 192-194 (1987).
Acsadi, et al., "Human dystrophin expression in mdx mice after intramuscular injection of DNA constructs", Nature, vol. 352, pp. 815-818 (1991).
Giguere, et al., "Identification of a receptor for the morphogen retinoic acid", Nature, vol. 330, pp. 624-629 (1987).
Ono, et al., "Plasmid DNAs directly injected into mouse brain with lipofectin can be incorporated and expressed by brain cells", Neuroscience Ltrs., vol. 117, pp. 259-263 (1990).
Whang, et al., "Expression of the Epstein-Barr Virus gp350/220 Gene in Rodent and Primate Cells", J. Virol., vol. 61, No. 6, pp. 1796-1807 (1987).
Gorman, et al., "Evolution of Influenza A Virus Nucleoptotein Genes: Implications for the Orgins of H1N1 Human and Classical Swine Viruses", J. Virol., vol. 65, No. 7, pp. 3704-3714 (1991).
Brigham, et al., Am. J. Med. Sci., vol. 298, pp. 278-281 (1989).
Wu, et al., "Targeting Genes: Delivery and Persistent Expression of a Foreign Gene Driven by Mammalian Regulatory Elements in Vivo", J. Bio. Chem., vol. 264, No. 29, pp. 16985-16987 (1989).
Cohen, "Naked DNA Points Way to Vaccines", Sci., vol. 259, pp. 1691-1692 (1993).
Frieng, "Gene Therapy may aid heart ailments", USA Today, p. 1-D, Feb. 11, 1991.
1993 Conf., Washington, DC, Bioeast, pp. 57-58, Jan. 24-27 (1993).

Waldholz, "Merck Team Develops a New Type of Vaccine from Gene Inside Virus", Wall Street Journal, Tech. & Med. Sect., Mar. 19, 1993.
Yakubov, et al., "Mechanism of oligonucleotide uptake by cells: Involvment of specific receptors?", Proc. Natl. Acad. Sci., USA, vol. 86, pp. 6454-6458 (1989).
Selden, et al., "Expression of the human growth hormone variant gene in cultured fibroblasts and trangenic mice", Proc. Natl. Acad. Sci., USA, vol. 85, pp. 8241-8245 (1988).
Loyter, et al., "Mechanisms of DNA uptake by mammaian cells: Fate of exogenously added DNA monitored by the use of fluorescent dyes", Proc. Natl. Acad. Sci., USA, vol. 79, pp. 422-426 (1982).
de Wet, et al., Firerly Luciferase Gene: Structure and Expression in mammalian Cells:, Mol. and Cell. Biol., pp. 725-734 (1987).
Chen, et al., "High-Efficiency Transformation of Mammalian Cells by Plasmid DNA", Mol. and Cell. Bio., pp. 2745-2752 (1987).
Felgner, et al., Proc. Natl. Acad. Sci., USA, vol. 84, pp. 7413-7417 (1987).
Cheng, et al., Proc. Natl. Acad. Sci., USA, vol. 90, pp. 4455-4459 (1993).
Berton, et al., "Antigenic Structure of the Infuenza B Virus Hemagglutinin: Nucleotide Sequence Analysis of Antigenic Variants Selected with Monoclonal Antibodies", J. Virol. vol. 52, No. 3, pp. 919-927.
Rota, et al., "Comparison of the Immune Response to Variant Infuenza Type B Hemagglutinins Expressed in Vaccinia Virus", vol. 161, No. 2, pp. 269-275 (1987).
Rodriguez, et al., Vectors a Survey of Molecular Cloning Vectors and their Uses, Buttersworth, Boston, pp. 467-492 (1988).
Physicians' Desk Ref., 46th Ed., Med. Economics, NJ, pp. 1204-1206 (1992).
Davis, et al., Microbiology—Including Immunology and Molecular Genetics, Third Edition, Hagerstown, Jarper and Row, p. 294 (1980).
Ledley, et al., "Clinical Considerations in the Design of Protocols for Somatic Gene Therapy", Human Gene Therapy, vol. 2, p. 77-83 (1991).
Haynes, et al., "Scientific and Social Issues of Human Immunodeficiency Virus Vaccine Development", Science, vol. 260, pp. 1279-1286, (May 28, 1993).
Hoffenbach, et al., "Unusually High Frequencies of HIV-Specific Cytotoxic T Lymphocytes in Humans", J. of Immunl., vol. 142, pp. 452-462, No. 9, Jan. 15, 1983.
Torpey, et al., "Effects of Adoptive Immunotherapy with Autologous CD8+ T Lymphocytes in Immunologic Parameters: Lymphocyte Subseys . . . ", Clin. Immunol. and Immunopathology, vol. 68, No. 3, Sep., pp. 263-272, 1993.
Butini, et al., J. of Cellular Biochemistry, Supplement 18B, p. 147, Abstract No. J306.
Knuth, et al., "Cellular and bumoral immune responses again cancer: implications for cancer vaccines", Current Opinion in Immunology, vol. 3, pp. 659-664 (1991).
Wang, et al., "Genetic Immunization: A Novel Method forVaccine Development against HIV", Vaccines 93 Cold Spring Harbor Laboratory Press, pp. 143-150.
Hammarskjold, et al., "Regulation of Human Immunodeficiency Virus env Expression by the rec Gene Product", J. of Vir., May 1989, pp. 1959-1966.
Morgan, et al., "Retroviral vectors containing putative internal ribsome entry sites: development of a polycistronic gene transfer system . . . ", Nucleic Acids Research, Vo. 20, No. 6, pp. 1293-1299.
Smarda, et al., "Dicistronic selection for nuclear proteins in living animal cells", Gene, vol. 137, pp. 145-149 (1993).

* cited by examiner

1 TCGCGCGTTT CGGTGATGAC GGTGAAAACC TCTGACACAT GCAGCTCCCG

51 GAGACGGTCA CAGCTTGTCT GTAAGCGGAT GCCGGGAGCA GACAAGCCCG

101 TCAGGGCGCG TCAGCGGGTG TTGGCGGGTG TCGGGGCTGG CTTAACTATG

151 CGGCATCAGA GCAGATTGTA CTGAGAGTGC ACCATATGCG GTGTGAAATA

201 CCGCACAGAT GCGTAAGGAG AAAATACCGC ATCAGATTGG CTATTGGCCA

251 TTGCATACGT TGTATCCATA TCATAATATG TACATTTATA TTGGCTCATG

301 TCCAACATTA CCGCCATGTT GACATTGATT ATTGACTAGT TATTAATAGT

351 AATCAATTAC GGGGTCATTA GTTCATAGCC CATATATGGA GTTCCGCGTT

401 ACATAACTTA CGGTAAATGG CCCGCCTGGC TGACCGCCCA ACGACCCCCG

451 CCCATTGACG TCAATAATGA CGTATGTTCC CATAGTAACG CCAATAGGGA

501 CTTTCCATTG ACGTCAATGG GTGGAGTATT TACGGTAAAC TGCCCACTTG

551 GCAGTACATC AAGTGTATCA TATGCCAAGT ACGCCCCCTA TTGACGTCAA

601 TGACGGTAAA TGGCCCGCCT GGCATTATGC CCAGTACATG ACCTTATGGG

651 ACTTTCCTAC TTGGCAGTAC ATCTACGTAT TAGTCATCGC TATTACCATG

701 GTGATGCGGT TTTGGCAGTA CATCAATGGG CGTGGATAGC GGTTTGACTC

751 ACGGGGATTT CCAAGTCTCC ACCCCATTGA CGTCAATGGG AGTTTGTTTT

801 GGCACCAAAA TCAACGGGAC TTTCCAAAAT GTCGTAACAA CTCCGCCCCA

851 TTGACGCAAA TGGGCGGTAG GCGTGTACGG TGGGAGGTCT ATATAAGCAG

901 AGCTCGTTTA GTGAACCGTC AGATCGCCTG GAGACGCCAT CCACGCTGTT

951 TTGACCTCCA TAGAAGACAC CGGGACCGAT CCAGCCTCCG CGGCCGGGAA

FIG.6A

1001 CGGTGCATTG GAACGCGGAT TCCCCGTGCC AAGAGTGACG TAAGTACCGC

1051 CTATAGAGTC TATAGGCCCA CCCCCTTGGC TTCTTATGCA TGCTATACTG

1101 TTTTTGGCTT GGGGTCTATA CACCCCCGCT TCCTCATGTT ATAGGTGATG

1151 GTATAGCTTA GCCTATAGGT GTGGGTTATT GACCATTATT GACCACTCCC

1201 CTATTGGTGA CGATACTTTC CATTACTAAT CCATAACATG GCTCTTTGCC

1251 ACAACTCTCT TTATTGGCTA TATGCCAATA CACTGTCCTT CAGAGACTGA

1301 CACGGACTCT GTATTTTTAC AGGATGGGGT CTCATTTATT ATTTACAAAT

1351 TCACATATAC AACACCACCG TCCCCAGTGC CCGCAGTTTT TATTAAACAT

1401 AACGTGGGAT CTCCACGCGA ATCTCGGGTA CGTGTTCCGG ACATGGGCTC

1451 TTCTCCGGTA GCGGCGGAGC TTCTACATCC GAGCCCTGCT CCCATGCCTC

1501 CAGCGACTCA TGGTCGCTCG GCAGCTCCTT GCTCCTAACA GTGGAGGCCA

1551 GACTTAGGCA CAGCACGATG CCCACCACCA CCAGTGTGCC GCACAAGGCC

1601 GTGGCGGTAG GGTATGTGTC TGAAAATGAG CTCGGGGAGC GGGCTTGCAC

1651 CGCTGACGCA TTTGGAAGAC TTAAGGCAGC GGCAGAAGAA GATGCAGGCA

1701 GCTGAGTTGT TGTGTTCTGA TAAGAGTCAG AGGTAACTCC CGTTGCGGTG

1751 CTGTTAACGG TGGAGGGCAG TGTAGTCTGA GCAGTACTCG TTGCTGCCGC

1801 GCGCGCCACC AGACATAATA GCTGACAGAC TAACAGACTG TTCCTTTCCA

1851 TGGGTCTTTT CTGCAGTCAC CGTCCTTAG ATCTGCTGTG CCTTCTAGTT

1901 GCCAGCCATC TGTTGTTTGC CCCTCCCCCG TGCCTTCCTT GACCCTGGAA

1951 GGTGCCACTC CCACTGTCCT TTCCTAATAA AATGAGGAAA TTGCATCGCA

FIG.6B

2001 TTGTCTGAGT AGGTGTCATT CTATTCTGGG GGGTGGGGTG GGGCAGCACA

2051 GCAAGGGGGA GGATTGGGAA GACAATAGCA GGCATGCTGG GGATGCGGTG

2101 GGCTCTATGG GTACCCAGGT GCTGAAGAAT TGACCCGGTT CCTCCTGGGC

2151 CAGAAAGAAG CAGGCACATC CCCTTCTCTG TGACACACCC TGTCCACGCC

2201 CCTGGTTCTT AGTTCCAGCC CCACTCATAG GACACTCATA GCTCAGGAGG

2251 GCTCCGCCTT CAATCCCACC CGCTAAAGTA CTTGGAGCGG TCTCTCCCTC

2301 CCTCATCAGC CCACCAAACC AAACCTAGCC TCCAAGAGTG GGAAGAAATT

2351 AAAGCAAGAT AGGCTATTAA GTGCAGAGGG AGAGAAAATG CCTCCAACAT

2401 GTGAGGAAGT AATGAGAGAA ATCATAGAAT TTCTTCCGCT TCCTCGCTCA

2451 CTGACTCGCT GCGCTCGGTC GTTCGGCTGC GGCGAGCGGT ATCAGCTCAC

2501 TCAAAGGCGG TAATACGGTT ATCCACAGAA TCAGGGGATA ACGCAGGAAA

2551 GAACATGTGA GCAAAAGGCC AGCAAAAGGC CAGGAACCGT AAAAAGGCCG

2601 CGTTGCTGGC GTTTTTCCAT AGGCTCCGCC CCCCTGACGA GCATCACAAA

2651 AATCGACGCT CAAGTCAGAG GTGGCGAAAC CCGACAGGAC TATAAAGATA

2701 CCAGGCGTTT CCCCCTGGAA GCTCCCTCGT GCGCTCTCCT GTTCCGACCC

2751 TGCCGCTTAC CGGATACCTG TCCGCCTTTC TCCCTTCGGG AAGCGTGGCG

2801 CTTTCTCAAT GCTCACGCTG TAGGTATCTC AGTTCGGTGT AGGTCGTTCG

2851 CTCCAAGCTG GGCTGTGTGC ACGAACCCCC CGTTCAGCCC GACCGCTGCG

2901 CCTTATCCGG TAACTATCGT CTTGAGTCCA ACCCGGTAAG ACACGACTTA

2951 TCGCCACTGG CAGCAGCCAC TGGTAACAGG ATTAGCAGAG CGAGGTATGT

FIG.6C

3001 AGGCGGTGCT ACAGAGTTCT TGAAGTGGTG GCCTAACTAC GGCTACACTA

3051 GAAGGACAGT ATTTGGTATC TGCGCTCTGC TGAAGCCAGT TACCTTCGGA

3101 AAAAGAGTTG GTAGCTCTTG ATCCGGCAAA CAAACCACCG CTGGTAGCGG

3151 TGGTTTTTTT GTTTGCAAGC AGCAGATTAC GCGCAGAAAA AAAGGATCTC

3201 AAGAAGATCC TTTGATCTTT TCTACGGGGT CTGACGCTCA GTGGAACGAA

3251 AACTCACGTT AAGGGATTTT GGTCATGAGA TTATCAAAAA GGATCTTCAC

3301 CTAGATCCTT TTAAATTAAA AATGAAGTTT TAAATCAATC TAAAGTATAT

3351 ATGAGTAAAC TTGGTCTGAC AGTTACCAAT GCTTAATCAG TGAGGCACCT

3401 ATCTCAGCGA TCTGTCTATT TCGTTCATCC ATAGTTGCCT GACTCCCCGT

3451 CGTGTAGATA ACTACGATAC GGGAGGGCTT ACCATCTGGC CCCAGTGCTG

3501 CAATGATACC GCGAGACCCA CGCTCACCGG CTCCAGATTT ATCAGCAATA

3551 AACCAGCCAG CCGGAAGGGC CGAGCGCAGA AGTGGTCCTG CAACTTTATC

3601 CGCCTCCATC CAGTCTATTA ATTGTTGCCG GGAAGCTAGA GTAAGTAGTT

3651 CGCCAGTTAA TAGTTTGCGC AACGTTGTTG CCATTGCTAC AGGCATCGTG

3701 GTGTCACGCT CGTCGTTTGG TATGGCTTCA TTCAGCTCCG GTTCCCAACG

3751 ATCAAGGCGA GTTACATGAT CCCCCATGTT GTGCAAAAAA GCGGTTAGCT

3801 CCTTCGGTCC TCCGATCGTT GTCAGAAGTA AGTTGGCCGC AGTGTTATCA

3851 CTCATGGTTA TGGCAGCACT GCATAATTCT CTTACTGTCA TGCCATCCGT

3901 AAGATGCTTT TCTGTGACTG GTGAGTACTC AACCAAGTCA TTCTGAGAAT

3951 AGTGTATGCG GCGACCGAGT TGCTCTTGCC CGGCGTCAAT ACGGGATAAT

FIG.6D

4001 ACCGCGCCAC ATAGCAGAAC TTTAAAAGTG CTCATCATTG GAAAACGTTC

4051 TTCGGGGCGA AAACTCTCAA GGATCTTACC GCTGTTGAGA TCCAGTTCGA

4101 TGTAACCCAC TCGTGCACCC AACTGATCTT CAGCATCTTT TACTTTCACC

4151 AGCGTTTCTG GGTGAGCAAA AACAGGAAGG CAAAATGCCG CAAAAAAGGG

4201 AATAAGGGCG ACACGGAAAT GTTGAATACT CATACTCTTC CTTTTTCAAT

4251 ATTATTGAAG CATTTATCAG GGTTATTGTC TCATGAGCGG ATACATATTT

4301 GAATGTATTT AGAAAAATAA ACAAATAGGG GTTCCGCGCA CATTTCCCCG

4351 AAAAGTGCCA CCTGACGTCT AAGAAACCAT TATTATCATG ACATTAACCT

4401 ATAAAAATAG GCGTATCACG AGGCCCTTTC GTC (SEQ ID NO: 12)

FIG.6E

1 TCGCGCGTTT CGGTGATGAC GGTGAAAACC TCTGACACAT GCAGCTCCCG

51 GAGACGGTCA CAGCTTGTCT GTAAGCGGAT GCCGGGAGCA GACAAGCCCG

101 TCAGGGCGCG TCAGCGGGTG TTGGCGGGTG TCGGGGCTGG CTTAACTATG

151 CGGCATCAGA GCAGATTGTA CTGAGAGTGC ACCATATGCG GTGTGAAATA

201 CCGCACAGAT GCGTAAGGAG AAAATACCGC ATCAGATTGG CTATTGGCCA

251 TTGCATACGT TGTATCCATA TCATAATATG TACATTTATA TTGGCTCATG

301 TCCAACATTA CCGCCATGTT GACATTGATT ATTGACTAGT TATTAATAGT

351 AATCAATTAC GGGGTCATTA GTTCATAGCC CATATATGGA GTTCCGCGTT

401 ACATAACTTA CGGTAAATGG CCCGCCTGGC TGACCGCCCA ACGACCCCCG

451 CCCATTGACG TCAATAATGA CGTATGTTCC CATAGTAACG CCAATAGGGA

501 CTTTCCATTG ACGTCAATGG GTGGAGTATT TACGGTAAAC TGCCCACTTG

551 GCAGTACATC AAGTGTATCA TATGCCAAGT ACGCCCCCTA TTGACGTCAA

601 TGACGGTAAA TGGCCCGCCT GGCATTATGC CCAGTACATG ACCTTATGGG

651 ACTTTCCTAC TTGGCAGTAC ATCTACGTAT TAGTCATCGC TATTACCATG

701 GTGATGCGGT TTTGGCAGTA CATCAATGGG CGTGGATAGC GGTTTGACTC

751 ACGGGGATTT CCAAGTCTCC ACCCCATTGA CGTCAATGGG AGTTTGTTTT

801 GGCACCAAAA TCAACGGGAC TTTCCAAAAT GTCGTAACAA CTCCGCCCCA

851 TTGACGCAAA TGGGCGGTAG GCGTGTACGG TGGGAGGTCT ATATAAGCAG

901 AGCTCGTTTA GTGAACCGTC AGATCGCCTG GAGACGCCAT CCACGCTGTT

951 TTGACCTCCA TAGAAGACAC CGGGACCGAT CCAGCCTCCG CGGCCGGGAA

FIG.7A

1001 CGGTGCATTG GAACGCGGAT TCCCCGTGCC AAGAGTGACG TAAGTACCGC

1051 CTATAGAGTC TATAGGCCCA CCCCCTTGGC TTCTTATGCA TGCTATACTG

1101 TTTTTGGCTT GGGGTCTATA CACCCCCGCT TCCTCATGTT ATAGGTGATG

1151 GTATAGCTTA GCCTATAGGT GTGGGTTATT GACCATTATT GACCACTCCC

1201 CTATTGGTGA CGATACTTTC CATTACTAAT CCATAACATG GCTCTTTGCC

1251 ACAACTCTCT TTATTGGCTA TATGCCAATA CACTGTCCTT CAGAGACTGA

1301 CACGGACTCT GTATTTTTAC AGGATGGGGT CTCATTTATT ATTTACAAAT

1351 TCACATATAC AACACCACCG TCCCCAGTGC CCGCAGTTTT TATTAAACAT

1401 AACGTGGGAT CTCCACGCGA ATCTCGGGTA CGTGTTCCGG ACATGGGCTC

1451 TTCTCCGGTA GCGGCGGAGC TTCTACATCC GAGCCCTGCT CCCATGCCTC

1501 CAGCGACTCA TGGTCGCTCG GCAGCTCCTT GCTCCTAACA GTGGAGGCCA

1551 GACTTAGGCA CAGCACGATG CCCACCACCA CCAGTGTGCC GCACAAGGCC

1601 GTGGCGGTAG GGTATGTGTC TGAAAATGAG CTCGGGGAGC GGGCTTGCAC

1651 CGCTGACGCA TTTGGAAGAC TTAAGGCAGC GGCAGAAGAA GATGCAGGCA

1701 GCTGAGTTGT TGTGTTCTGA TAAGAGTCAG AGGTAACTCC CGTTGCGGTG

1751 CTGTTAACGG TGGAGGGCAG TGTAGTCTGA GCAGTACTCG TTGCTGCCGC

1801 GCGCGCCACC AGACATAATA GCTGACAGAC TAACAGACTG TTCCTTTCCA

1851 TGGGTCTTTT CTGCAGTCAC CGTCCTTAG ATCTGCTGTG CCTTCTAGTT

1901 GCCAGCCATC TGTTGTTTGC CCCTCCCCCG TGCCTTCCTT GACCCTGGAA

1951 GGTGCCACTC CCACTGTCCT TTCCTAATAA AATGAGGAAA TTGCATCGCA

2001 TTGTCTGAGT AGGTGTCATT CTATTCTGGG GGGTGGGGTG GGGCAGCACA

FIG.7B

2051 GCAAGGGGGA GGATTGGGAA GACAATAGCA GGCATGCTGG GGATGCGGTG
2101 GGCTCTATGG GTACCCAGGT GCTGAAGAAT TGACCCGGTT CCTCCTGGGC
2151 CAGAAAGAAG CAGGCACATC CCCTTCTCTG TGACACACCC TGTCCACGCC
2201 CCTGGTTCTT AGTTCCAGCC CCACTCATAG GACACTCATA GCTCAGGAGG
2251 GCTCCGCCTT CAATCCCACC CGCTAAAGTA CTTGGAGCGG TCTCTCCCTC
2301 CCTCATCAGC CCACCAAACC AAACCTAGCC TCCAAGAGTG GGAAGAAATT
2351 AAAGCAAGAT AGGCTATTAA GTGCAGAGGG AGAGAAAATG CCTCCAACAT
2401 GTGAGGAAGT AATGAGAGAA ATCATAGAAT TTCTTCCGCT TCCTCGCTCA
2451 CTGACTCGCT GCGCTCGGTC GTTCGGCTGC GGCGAGCGGT ATCAGCTCAC
2501 TCAAAGGCGG TAATACGGTT ATCCACAGAA TCAGGGGATA ACGCAGGAAA
2551 GAACATGTGA GCAAAAGGCC AGCAAAAGGC CAGGAACCGT AAAAAGGCCG
2601 CGTTGCTGGC GTTTTTCCAT AGGCTCCGCC CCCCTGACGA GCATCACAAA
2651 AATCGACGCT CAAGTCAGAG GTGGCGAAAC CCGACAGGAC TATAAAGATA
2701 CCAGGCGTTT CCCCCTGGAA GCTCCCTCGT GCGCTCTCCT GTTCCGACCC
2751 TGCCGCTTAC CGGATACCTG TCCGCCTTTC TCCCTTCGGG AAGCGTGGCG
2801 CTTTCTCAAT GCTCACGCTG TAGGTATCTC AGTTCGGTGT AGGTCGTTCG
2851 CTCCAAGCTG GGCTGTGTGC ACGAACCCCC CGTTCAGCCC GACCGCTGCG
2901 CCTTATCCGG TAACTATCGT CTTGAGTCCA ACCCGGTAAG ACACGACTTA
2951 TCGCCACTGG CAGCAGCCAC TGGTAACAGG ATTAGCAGAG CGAGGTATGT
3001 AGGCGGTGCT ACAGAGTTCT TGAAGTGGTG GCCTAACTAC GGCTACACTA
3051 GAAGGACAGT ATTTGGTATC TGCGCTCTGC TGAAGCCAGT TACCTTCGGA

FIG.7C

3101 AAAAGAGTTG GTAGCTCTTG ATCCGGCAAA CAAACCACCG CTGGTAGCGG

3151 TGGTTTTTTT GTTTGCAAGC AGCAGATTAC GCGCAGAAAA AAAGGATCTC

3201 AAGAAGATCC TTTGATCTTT TCTACGGGGT CTGACGCTCA GTGGAACGAA

3251 AACTCACGTT AAGGGATTTT GGTCATGAGA TTATCAAAAA GGATCTTCAC

3301 CTAGATCCTT TTAAATTAAA AATGAAGTTT TAAATCAATC TAAAGTATAT

3351 ATGAGTAAAC TTGGTCTGAC AGTTACCAAT GCTTAATCAG TGAGGCACCT

3401 ATCTCAGCGA TCTGTCTATT TCGTTCATCC ATAGTTGCCT GACTCCGGGG

3451 GGGGGGGGCG CTGAGGTCTG CCTCGTGAAG AAGGTGTTGC TGACTCATAC

3501 CAGGCCTGAA TCGCCCCATC ATCCAGCCAG AAAGTGAGGG AGCCACGGTT

3551 GATGAGAGCT TTGTTGTAGG TGGACCAGTT GGTGATTTTG AACTTTTGCT

3601 TTGCCACGGA ACGGTCTGCG TTGTCGGGAA GATGCGTGAT CTGATCCTTC

3651 AACTCAGCAA AAGTTCGATT TATTCAACAA AGCCGCCGTC CCGTCAAGTC

3701 AGCGTAATGC TCTGCCAGTG TTACAACCAA TTAACCAATT CTGATTAGAA

3751 AAACTCATCG AGCATCAAAT GAAACTGCAA TTTATTCATA TCAGGATTAT

3801 CAATACCATA TTTTTGAAAA AGCCGTTTCT GTAATGAAGG AGAAAACTCA

3851 CCGAGGCAGT TCCATAGGAT GGCAAGATCC TGGTATCGGT CTGCGATTCC

3901 GACTCGTCCA ACATCAATAC AACCTATTAA TTTCCCCTCG TCAAAAATAA

3951 GGTTATCAAG TGAGAAATCA CCATGAGTGA CGACTGAATC CGGTGAGAAT

4001 GGCAAAAGCT TATGCATTTC TTTCCAGACT TGTTCAACAG GCCAGCCATT

4051 ACGCTCGTCA TCAAAATCAC TCGCATCAAC CAAACCGTTA TTCATTCGTG

4101 ATTGCGCCTG AGCGAGACGA AATACGCGAT CGCTGTTAAA AGGACAATTA

FIG.7D

4151 CAAACAGGAA TCGAATGCAA CCGGCGCAGG AACACTGCCA GCGCATCAAC

4201 AATATTTTCA CCTGAATCAG GATATTCTTC TAATACCTGG AATGCTGTTT

4251 TCCCGGGGAT CGCAGTGGTG AGTAACCATG CATCATCAGG AGTACGGATA

4301 AAATGCTTGA TGGTCGGAAG AGGCATAAAT TCCGTCAGCC AGTTTAGTCT

4351 GACCATCTCA TCTGTAACAT CATTGGCAAC GCTACCTTTG CCATGTTTCA

4401 GAAACAACTC TGGCGCATCG GGCTTCCCAT ACAATCGATA GATTGTCGCA

4451 CCTGATTGCC CGACATTATC GCGAGCCCAT TTATACCCAT ATAAATCAGC

4501 ATCCATGTTG GAATTTAATC GCGGCCTCGA GCAAGACGTT TCCCGTTGAA

4551 TATGGCTCAT AACACCCCTT GTATTACTGT TTATGTAAGC AGACAGTTTT

4601 ATTGTTCATG ATGATATATT TTTATCTTGT GCAATGTAAC ATCAGAGATT

4651 TTGAGACACA ACGTGGCTTT CCCCCCCCCC CCATTATTGA AGCATTTATC

4701 AGGGTTATTG TCTCATGAGC GGATACATAT TTGAATGTAT TTAGAAAAAT

4751 AAACAAATAG GGGTTCCGCG CACATTTCCC CGAAAAGTGC CACCTGACGT

4801 CTAAGAAACC ATTATTATCA TGACATTAAC CTATAAAAAT AGGCGTATCA

4851 CGAGGCCCTT TCGTC (SEQ ID NO:14)

FIG.7E

1 ATTGGCTATT GGCCATTGCA TACGTTGTAT CCATATCATA ATATGTACAT

51 TTATATTGGC TCATGTCCAA CATTACCGCC ATGTTGACAT TGATTATTGA

101 CTAGTTATTA ATAGTAATCA ATTACGGGGT CATTAGTTCA TAGCCCATAT

151 ATGGAGTTCC GCGTTACATA ACTTACGGTA AATGGCCCGC CTGGCTGACC

201 GCCCAACGAC CCCCGCCCAT TGACGTCAAT AATGACGTAT GTTCCCATAG

251 TAACGCCAAT AGGGACTTTC CATTGACGTC AATGGGTGGA GTATTTACGG

301 TAAACTGCCC ACTTGGCAGT ACATCAAGTG TATCATATGC CAAGTACGCC

351 CCCTATTGAC GTCAATGACG GTAAATGGCC CGCCTGGCAT TATGCCCAGT

401 ACATGACCTT ATGGGACTTT CCTACTTGGC AGTACATCTA CGTATTAGTC

451 ATCGCTATTA CCATGGTGAT GCGGTTTTGG CAGTACATCA ATGGGCGTGG

501 ATAGCGGTTT GACTCACGGG GATTTCCAAG TCTCCACCCC ATTGACGTCA

551 ATGGGAGTTT GTTTTGGCAC CAAAATCAAC GGGACTTTCC AAAATGTCGT

601 AACAACTCCG CCCCATTGAC GCAAATGGGC GGTAGGCGTG TACGGTGGGA

651 GGTCTATATA AGCAGAGCTC GTTTAGTGAA CCGTCAGATC GCCTGGAGAC

701 GCCATCCACG CTGTTTTGAC CTCCATAGAA GACACCGGGA CCGATCCAGC

751 CTCCGCGGCC GGGAACGGTG CATTGGAACG CGGATTCCCC GTGCCAAGAG

801 TGACGTAAGT ACCGCCTATA GAGTCTATAG GCCCACCCCC TTGGCTTCTT

851 ATGCATGCTA TACTGTTTTT GGCTTGGGGT CTATACACCC CCGCTTCCTC

901 ATGTTATAGG TGATGGTATA GCTTAGCCTA TAGGTGTGGG TTATTGACCA

951 TTATTGACCA CTCCCCTATT GGTGACGATA CTTTCCATTA CTAATCCATA

1001 ACATGGCTCT TTGCCACAAC TCTCTTTATT GGCTATATGC CAATACACTG

FIG.8A

1051 TCCTTCAGAG ACTGACACGG ACTCTGTATT TTTACAGCAT GGGGTCTCAT

1101 TTATTATTTA CAAATTCACA TATACAACAC CACCGTCCCC AGTGCCCGCA

1151 GTTTTTATTA AACATAACGT GGGATCTCCA CGCGAATCTC GGGTACGTGT

1201 TCCGGACATG GGCTCTTCTC CGGTAGCGGC GGAGCTTCTA CATCCGAGCC

1251 CTGCTCCCAT GCCTCCAGCG ACTCATGGTC GCTCGGCAGC TCCTTGCTCC

1301 TAACAGTGGA GGCCAGACTT AGGCACAGCA CGATGCCCAC CACCACCAGT

1351 GTGCCGCACA AGGCCGTGGC GGTAGGGTAT GTGTCTGAAA ATGAGCTCGG

1401 GGAGCGGGCT TGCACCGCTG ACGCATTTGG AAGACTTAAG GCAGCGGCAG

1451 AAGAAGATGC AGGCAGCTGA GTTGTTGTGT TCTGATAAGA GTCAGAGGTA

1501 ACTCCCGTTG CGGTGCTGTT AACGGTGGAG GGCAGTGTAG TCTGAGCAGT

1551 ACTCGTTGCT GCCGCGCGCG CCACCAGACA TAATAGCTGA CAGACTAACA

1601 GACTGTTCCT TTCCATGGGT CTTTTCTGCA GTCACCGTCC TTAGATCTG

1651 CTGTGCCTTC TAGTTGCCAG CCATCTGTTG TTTGCCCCTC CCCCGTGCCT

1701 TCCTTGACCC TGGAAGGTGC CACTCCCACT GTCCTTTCCT AATAAAATGA

1751 GGAAATTGCA TCGCATTGTC TGAGTAGGTG TCATTCTATT CTGGGGGGTG

1801 GGGTGGGGCA GCACAGCAAG GGGGAGGATT GGGAAGACAA TAGCAGGCAT

1851 GCTGGGGATG CGGTGGGCTC TATGGGTACC CAGGTGCTGA AGAATTGACC

1901 CGGTTCCTCC TGGGCCAGAA AGAAGCAGGC ACATCCCCTT CTCTGTGACA

1951 CACCCTGTCC ACGCCCCTGG TTCTTAGTTC CAGCCCCACT CATAGGACAC

2001 TCATAGCTCA GGAGGGCTCC GCCTTCAATC CCACCCGCTA AAGTACTTGG

2051 AGCGGTCTCT CCCTCCCTCA TCAGCCCACC AAACCAAACC TAGCCTCCAA

2101 GAGTGGGAAG AAATTAAAGC AAGATAGGCT ATTAAGTGCA GAGGGAGAGA

2151 AAATGCCTCC AACATGTGAG GAAGTAATGA GAGAAATCAT AGAATTC

FIG.8B

1 GATATTGG CTATTGGCCA

251 TTGCATACGT TGTATCCATA TCATAATATG TACATTTATA TTGGCTCATG

301 TCCAACATTA CCGCCATGTT GACATTGATT ATTGACTAGT TATTAATAGT

351 AATCAATTAC GGGGTCATTA GTTCATAGCC CATATATGGA GTTCCGCGTT

401 ACATAACTTA CGGTAAATGG CCCGCCTGGC TGACCGCCCA ACGACCCCCG

451 CCCATTGACG TCAATAATGA CGTATGTTCC CATAGTAACG CCAATAGGGA

501 CTTTCCATTG ACGTCAATGG GTGGAGTATT TACGGTAAAC TGCCCACTTG

551 GCAGTACATC AAGTGTATCA TATGCCAAGT ACGCCCCCTA TTGACGTCAA

601 TGACGGTAAA TGGCCCGCCT GGCATTATGC CCAGTACATG ACCTTATGGG

651 ACTTTCCTAC TTGGCAGTAC ATCTACGTAT TAGTCATCGC TATTACCATG

701 GTGATGCGGT TTTGGCAGTA CATCAATGGG CGTGGATAGC GGTTTGACTC

751 ACGGGGATTT CCAAGTCTCC ACCCCATTGA CGTCAATGGG AGTTTGTTTT

801 GGCACCAAAA TCAACGGGAC TTTCCAAAAT GTCGTAACAA CTCCGCCCCA

851 TTGACGCAAA TGGGCGGTAG GCGTGTACGG TGGGAGGTCT ATATAAGCAG

901 AGCTCGTTTA GTGAACCGTC AGATCGCCTG GAGACGCCAT CCACGCTGTT

951 TTGACCTCCA TAGAAGACAC CGGGACCGAT CCAGCCTCCG CGGCCGGGAA

1001 CGGTGCATTG GAACGCGGAT TCCCCGTGCC AAGAGTGACG TAAGTACCGC

1051 CTATAGAGTC TATAGGCCCA CCCCCTTGGC TTCTTATGCA TGCTATACTG

1101 TTTTTGGCTT GGGGTCTATA CACCCCCGCT TCCTCATGTT ATAGGTGATG

1151 GTATAGCTTA GCCTATAGGT GTGGGTTATT GACCATTATT GACCACTCCC

1201 CTATTGGTGA CGATACTTTC CATTACTAAT CCATAACATG GCTCTTTGCC

FIG.11A

1251 ACAACTCTCT TTATTGGCTA TATGCCAATA CACTGTCCTT CAGAGACTGA

1301 CACGGACTCT GTATTTTTAC AGGATGGGGT CTCATTTATT ATTTACAAAT

1351 TCACATATAC AACACCACCG TCCCCAGTGC CCGCAGTTTT TATTAAACAT

1401 AACGTGGGAT CTCCACGCGA ATCTCGGGTA CGTGTTCCGG ACATGGGCTC

1451 TTCTCCGGTA GCGGCGGAGC TTCTACATCC GAGCCCTGCT CCCATGCCTC

1501 CAGCGACTCA TGGTCGCTCG GCAGCTCCTT GCTCCTAACA GTGGAGGCCA

1551 GACTTAGGCA CAGCACGATG CCCACCACCA CCAGTGTGCC GCACAAGGCC

1601 GTGGCGGTAG GGTATGTGTC TGAAAATGAG CTCGGGGAGC GGGCTTGCAC

1651 CGCTGACGCA TTTGGAAGAC TTAAGGCAGC GGCAGAAGAA GATGCAGGCA

1701 GCTGAGTTGT TGTGTTCTGA TAAGAGTCAG AGGTAACTCC CGTTGCGGTG

1751 CTGTTAACGG TGGAGGGCAG TGTAGTCTGA GCAGTACTCG TTGCTGCCGC

1801 GCGCGCCACC AGACATAATA GCTGACAGAC TAACAGACTG TTCCTTTCCA

1851 TGGGTCTTTT CTGCAGTCAC CGTCCTTAG ATCTGCTGTG CCTTCTAGTT

1901 GCCAGCCATC TGTTGTTTGC CCCTCCCCCG TGCCTTCCTT GACCCTGGAA

1951 GGTGCCACTC CCACTGTCCT TTCCTAATAA AATGAGGAAA TTGCATCGCA

2001 TTGTCTGAGT AGGTGTCATT CTATTCTGGG GGGTGGGGTG GGGCAGCACA

2051 GCAAGGGGGA GGATTGGGAA GACAATAGCA GGCATGCTGG GGATGCGGTG

2101 GGCTCTATGG GTAC GGCCGCAGCGGCC GTACCCAGGT GCTGAAGAAT

TGACCCGGTT CCTCGACCCGT AAAAAGGCCG

2601 CGTTGCTGGC GTTTTTCCAT AGGCTCCGCC CCCCTGACGA GCATCACAAA

2651 AATCGACGCT CAAGTCAGAG GTGGCGAAAC CCGACAGGAC TATAAAGATA

FIG.11B

2701 CCAGGCGTTT CCCCCTGGAA GCTCCCTCGT GCGCTCTCCT GTTCCGACCC

2751 TGCCGCTTAC CGGATACCTG TCCGCCTTTC TCCCTTCGGG AAGCGTGGCG

2801 CTTTCTCAAT GCTCACGCTG TAGGTATCTC AGTTCGGTGT AGGTCGTTCG

2851 CTCCAAGCTG GGCTGTGTGC ACGAACCCCC CGTTCAGCCC GACCGCTGCG

2901 CCTTATCCGG TAACTATCGT CTTGAGTCCA ACCCGGTAAG ACACGACTTA

2951 TCGCCACTGG CAGCAGCCAC TGGTAACAGG ATTAGCAGAG CGAGGTATGT

3001 AGGCGGTGCT ACAGAGTTCT TGAAGTGGTG GCCTAACTAC GGCTACACTA

3051 GAAGGACAGT ATTTGGTATC TGCGCTCTGC TGAAGCCAGT TACCTTCGGA

3101 AAAAGAGTTG GTAGCTCTTG ATCCGGCAAA CAAACCACCG CTGGTAGCGG

3151 TGGTTTTTTT GTTTGCAAGC AGCAGATTAC GCGCAGAAAA AAAGGATCTC

3201 AAGAAGATCC TTTGATCTTT TCTACGTGATCC CGTAATGC TCTGCCAGTG

TTACAACCAA TTAACCAATT CTGATTAGAA

3751 AAACTCATCG AGCATCAAAT GAAACTGCAA TTTATTCATA TCAGGATTAT

3801 CAATACCATA TTTTTGAAAA AGCCGTTTCT GTAATGAAGG AGAAAACTCA

3851 CCGAGGCAGT TCCATAGGAT GGCAAGATCC TGGTATCGGT CTGCGATTCC

3901 GACTCGTCCA ACATCAATAC AACCTATTAA TTTCCCCTCG TCAAAAATAA

3951 GGTTATCAAG TGAGAAATCA CCATGAGTGA CGACTGAATC CGGTGAGAAT

4001 GGCAAAAGCT TATGCATTTC TTTCCAGACT TGTTCAACAG GCCAGCCATT

4051 ACGCTCGTCA TCAAAATCAC TCGCATCAAC CAAACCGTTA TTCATTCGTG

4101 ATTGCGCCTG AGCGAGACGA AATACGCGAT CGCTGTTAAA AGGACAATTA

4151 CAAACAGGAA TCGAATGCAA CCGGCGCAGG AACACTGCCA GCGCATCAAC

FIG.11C

4201 AATATTTTCA CCTGAATCAG GATATTCTTC TAATACCTGG AATGCTGTTT

4251 TCCCGGGGAT CGCAGTGGTG AGTAACCATG CATCATCAGG AGTACGGATA

4301 AAATGCTTGA TGGTCGGAAG AGGCATAAAT TCCGTCAGCC AGTTTAGTCT

4351 GACCATCTCA TCTGTAACAT CATTGGCAAC GCTACCTTTG CCATGTTTCA

4401 GAAACAACTC TGGCGCATCG GGCTTCCCAT ACAATCGATA GATTGTCGCA

4451 CCTGATTGCC CGACATTATC GCGAGCCCAT TTATACCCAT ATAAATCAGC

4501 ATCCATGTTG GAATTTAATC GCGGCCTCGA GCAAGACGTT TCCCGTTGAA

4551 TATGGCTCAT AACACCCCTT GTATTACTGT TTATGTAAGC AGACAGTTTT

4601 ATTGTTCATG ATGATATATT TTTATCTTGT GCAATGTAAC ATCAGAGATT

4651 TTGAGACACA ACGTGGCTTT CC (SEQ ID NO:100)

FIG.11D

COORDINATE IN VIVO GENE EXPRESSION

CROSS-RELATED TO OTHER APPLICATIONS

This application is a continuation of U.S. application Ser. No. 08/702,502, filed Mar. 3, 1997, now abandoned, which is the §371 U.S. national phase prosecution of PCT international application serial no. PCT/US95/02633, filed Mar. 3, 1995, which is a continuation-in-part of U.S. application Ser. No. 08/207,525, filed Mar. 7, 1994, now abandoned.

BACKGROUND OF THE INVENTION

1. Field of the Invention

A method for coordinate expression in a single cell, in vivo, of exogenous genes via introduction into the tissue of a vertebrate of polycistronic polynucleotide constructs is described. The method results in production of immune responses against the products produced as a result of expression of the exogenous genes. The method and polynucleotide constructs of this invention may be used in a vertebrate to generate immune responses against antigenic epitopes expressed by a single cell. The coordinate expression results in improved expression of gene products which may be otherwise poorly expressed. It also results in improved cellular immune responses due to provision of T-cell stimulatory signals by the same cell expressing T-cell antigens. Polynucleotide constructs encoding human immunodeficiency virus (HIV) antigens exemplify one embodiment of the method.

2. Background of the Invention

A major challenge to the development of vaccines against viruses, particularly viruses with a high rate of mutation such as HIV, against which elicitation of neutralizing and protective immune responses is desirable, is the diversity of the viral envelope proteins among different viral isolates or strains. Because cytotoxic T-lymphocytes (CTLs) in both mice and humans are capable of recognizing epitopes derived from conserved internal viral proteins and may be important in the immune response against viruses, efforts have been directed towards the development of CTL vaccines that elicit heterologous protection against different viral strains.

$CD8^+$ CTLs kill virally-infected cells when their T cell receptors recognize viral peptides associated with MHC class I molecules. These peptides are derived from endogenously synthesized viral proteins. Thus, by recognition of epitopes from conserved viral proteins, CTLs may provide cross-strain protection. Peptides capable of associating with MHC class I for CTL recognition originate from proteins that are present in or pass through the cytoplasm or endoplasmic reticulum. Exogenous proteins which enter the endosomal processing pathway (as in the case of antigens presented by MHC class II molecules) are not usually effective in generating $CD8^+$ CTL responses.

Efforts to generate CTL responses have used replicating vectors to produce the protein antigen within the cell or have introduced peptides into the cytosol. These approaches have limitations that may limit their utility as vaccines. Retroviral vectors have restrictions on the size and structure of polypeptides that can be expressed as fusion proteins while maintaining the ability of the recombinant virus to replicate. Further, the effectiveness of vectors such as vaccinia for subsequent immunizations may be compromised by immune responses against the vectors themselves. Also, viral vectors and modified pathogens have inherent risks that may hinder their use in humans [R. R. Redfield et al., New Engl. J. Med. 316, 673 (1987); L. Mascola et al., Arch. Intern. Med. 149, 1569 (1989)]. Furthermore, the selection of peptide epitopes to be presented is dependent upon the structure of an individual's MHC antigens; thus, peptide vaccines may have limited effectiveness due to the diversity of MHC haplotypes in outbred populations.

Benvenisty, N., and Reshef, L. [PNAS 83, 9551–9555, (1986)] showed that $CaCl_2$-precipitated DNA introduced into mice intraperitoneally (i.p.), intravenously (i.v.) or intramuscularly (i.m.) could be expressed. Intramuscular injection of DNA expression vectors in mice results in the uptake of DNA by the muscle cells and expression of the protein encoded by the DNA [J. A. Wolff et al., Science 247, 1465 (1990); G. Ascadi et al., Nature 352, 815 (1991)]. The plasmids were maintained episomally and did not replicate. Subsequently, persistent expression has been observed after i.m. injection in skeletal muscle of rats, fish and primates, and cardiac muscle of rats. The technique of using nucleic acids as therapeutic agents was reported in WO90/11092 (4 Oct. 1990), in which naked polynucleotides were used to vaccinate vertebrates.

It is not necessary for the success of the method that immunization be intramuscular. Thus, Tang et al., [Nature, 356, 152–154 (1992)] disclosed that introduction of gold microprojectiles coated with DNA encoding bovine growth hormone (BGH) into the skin of mice resulted in production of anti-BGH antibodies in the mice. Furth et al., [Anal. Biochem. 205, 365–368, (1992)] showed that a jet injector could be used to transfect skin, muscle, fat, and mammary tissues of living animals. Methods for introducing nucleic acids was recently reviewed by Friedman, T., [Science, 244, 1275–1281 (1989)]. Robinson et al., [Abstracts of Papers Presented at the 1992 meeting on Modern Approaches to New Vaccines, Including Prevention of AIDS, Cold Spring Harbor, p92] reported that i.m., i.p., and i.v. administration of avian influenza DNA into chickens provided protection against lethal challenge. However, Robinson et al. did not disclose which avian influenza virus genes were used. In addition, only H7 specific immune responses were alleged; the induction of cross-strain protection was not discussed. Intravenous injection of a DNA:cationic liposome complex in mice was shown by Zhu et al., [Science 261:209–211 (9 Jul. 1993); see also WO93/24640, 9 Dec. 1993] to result in systemic expression of a cloned transgene. Recently, Ulmer et al., [Science 259:1745–1749, (1993)] reported on the heterologous protection against influenza virus infection by injection of DNA encoding influenza virus proteins.

The need for specific therapeutic and prophylactic agents capable of eliciting desired immune responses against pathogens and tumor antigens is achieved by the instant invention. Of particular importance in this therapeutic approach is the ability to induce T-cell immune responses which can prevent infections or disease caused by virus strains which are heterologous to the strain from which the antigen gene was obtained. This is of significance with HIV, since HIV mutates rapidly, and because many virulent isolates have been identified [see, for example, LaRosa et al., Science 249:932–935 (1990), identifying 245 separate HIV isolates].

In response to this diversity, researchers have attempted to generate CTLs by peptide immunization. Thus, Takahashi et al., [Science 255:333–336 (1992)] reported on the induction of broadly cross-reactive cytotoxic T cells recognizing an HIV envelope (gp160) determinant. They recognized the difficulty in achieving a truly cross-reactive CTL response and suggested that there is a dichotomy between the priming or restimulation of T cells, which is very stringent, and the elicitation of effector function, including cytotoxicity, from already stimulated CTLs.

Wang et al., [P.N.A.S. USA 90:4156–4160 (May, 1993)] reported on elicitation of immune responses in mice against HIV by intramuscular inoculation with a cloned, genomic (unspliced) HIV gene. The level of immune response achieved was low, and the system utilized portions of the mouse mammary tumor virus (MMTV) long terminal repeat (LTR) promoter and portions of the simian virus 40 (SV40) promoter and terminator. SV40 is known to transform cells, possibly through integration into host cellular DNA. Therefore, unlike the system described herein, the system described by Wang et al. may be inappropriate for administration to humans. In addition, the DNA construct of Wang et al. contains an essentially genomic piece of HIV encoding contiguous Tat/REV-gp160-Tat/REV coding sequences (FIG. 1). As is described in detail below, this is a suboptimal system for obtaining high-level expression of the gp160. One drawback is that the expression of Tat has been recognized to play a contributory role in the progression of Kaposi's Sarcoma, [Y. N. Vaishav and F. W. Wong-Staal, An. Rev. Biochem. (1991)].

WO 93/17706 describes a method for vaccinating an animal against a virus, wherein carrier particles were coated with a gene construct and the coated particles are accelerated into cells of an animal. In regard to HIV, essentially the entire genome, minus the long terminal repeats, was proposed to be used. That method may represent a substantial risk for recipients. Constructs of HIV should, in general, contain less than about 50% of the HIV genome to ensure safety of the vaccine. Thus, a number of problems remain if a useful human HIV vaccine is to emerge from the gene-delivery technology.

The instant invention uses known methods for introducing polynucleotides into living tissue to induce expression of proteins. This invention provides a immunogen for introducing HIV and other proteins into the antigen processing pathway to efficiently generate HIV-specific CTLs and antibodies. The pharmaceutical is effective as a vaccine to induce both cellular and humoral anti-HIV and HIV neutralizing immune responses. The instant invention addresses some of the problems by providing polynucleotide immunogens which, when introduced into an animal, direct the efficient expression of HIV proteins and epitopes without the attendant risks associated with those methods. The immune responses generated are effective at recognizing HIV, at inhibiting replication of HIV, at identifying and killing cells infected with HIV, and are cross-reactive against many HIV strains. Therefore, this invention provides a useful immunogen against HIV. The invention also provides polynucleotide constructs which enable the co-expression, in vivo, of more than one gene-product in a single cell. This is demonstrated with an HIV gene expression system in which the expression of a first gene is dependent on the co-expression in the same cell of a second gene product. By virtue of the success of achieving this co-expression in vivo, it is now predictable that this type of polynucleotide construct may be applied to co-expression in vivo of many combinations of gene products, including but not limited to viral antigens other than HIV related antigens, carcinoma-associated antigens, and immunomodulatory or immunostimulatory gene products.

SUMMARY OF THE INVENTION

Nucleic acids, including DNA constructs and RNA transcripts, capable of inducing coordinate expression of two to three cistrons upon direct introduction into animal tissues, are presented. In one embodiment, coordinate expression of two cistrons encoding HIV proteins and elicitation of HIV specific immune responses against more than one gene products is demonstrated. Cytotoxic T lymphocytes (CTLs) specific for viral antigens which respond to different strains of human immunodeficiency virus (HIV), and antibodies which are generally strain-specific are generated. The generation of such CTLs in vivo usually requires endogenous expression of the antigen, as in the case of virus infection. To generate a viral antigen for presentation to the immune system, without the limitations of direct peptide delivery or the use of viral vectors, polynucleotides encoding HIV proteins are directly introduced into tissues of vertebrates in vivo, the polynucleotides are taken up by cells within the tissue, and the encoded proteins produced and processed for presentation to the immune system. In mice, this resulted in the generation of HIV-specific CTLs and antibodies. Similar results are achieved in primates. These results are achieved with bi- or tri-cistronic nucleic acid polynucleotides encoding and co-expressing HIV gene products, immunostimulatory gene products including but not limited to GM-CSF, interleukins, interferon and B7 proteins, which act as T-cell costimulatory elements. The methods and polynucleotides of this invention are generally applicable to co-ordinate expression in vivo of any two or three genes. Thus, various embodiments of this invention include coordinate expression in vivo of viral antigens and immunostimulatory gene products as well as coordinate expression of tumor antigens and immunostimulatory genes.

BRIEF DESCRIPTION OF THE DRAWINGS

FIG. 6. V1J Sequence.

FIG. 7. V1Jneo Sequence.

FIG. 8. CMVintABGH Sequence.

FIG. 11. Sequence of the Vector V1R.

DETAILED DESCRIPTION OF THE INVENTION

Figure 1:
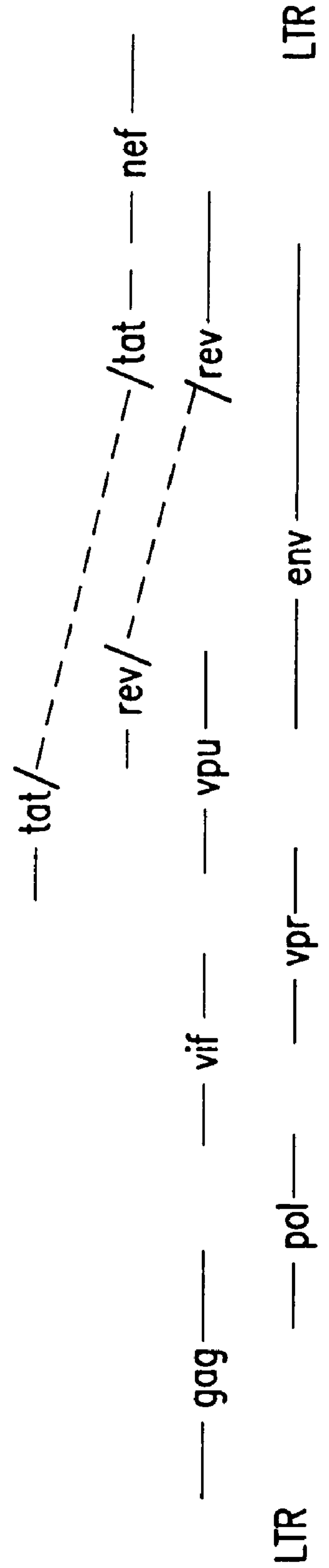
FIG. 1. A schematic representation of the HIV genome.

Nucleic acids, including DNA constructs and RNA transcripts, capable of inducing coordinate expression of two to three cistrons upon direct introduction into animal tissues, are presented. In one embodiment, coordinate expression of two cistrons encoding HIV proteins and elicitation of HIV specific immune responses against more than one gene products is demonstrated. Cytotoxic T lymphocytes (CTLs) specific for viral antigens which respond to different strains of human immunodeficiency virus (HIV), and antibodies which are generally strain-specific are generated. The generation of such CTLs in vivo usually requires endogenous expression of the antigen, as in the case of virus infection. To generate a viral antigen for presentation to the immune system, without the limitations of direct peptide delivery or the use of viral vectors, polynucleotides encoding HIV proteins are directly introduced into tissues of vertebrates in vivo, the polynucleotides are taken up by cells within the tissue, and the encoded proteins produced and processed for presentation to the immune system. In mice, this resulted in the generation of HIV-specific CTLs and antibodies. Similar results are achieved in primates. These results are achieved with bi- or tri-cistronic nucleic acid polynucleotides encoding and co-expressing HIV gene products, immunostimulatory gene products including but not limited to GM-CSF, interleukins, interferon and B7 proteins, which act as T-cell costimulatory elements. The methods and polynucleotides of this invention are generally applicable to co-ordinate expression in vivo of any two or three genes. Thus, various embodiments of this invention include coordinate expression in vivo of viral antigens and immunostimulatory gene products as well as coordinate expression of tumor antigens and immunostimulatory genes.

This invention provides polynucleotides which, when directly introduced into a vertebrate in vivo, including mammals such as primates and humans, induces the expression of encoded proteins within the animal.

As used herein, a polynucleotide is a nucleic acid which contains essential regulatory elements such that upon introduction into a living vertebrate cell, is able to direct the cellular machinery to produce translation products encoded by the genes comprising the polynucleotide.

In one embodiment of the invention, the polynucleotide is a polydeoxyribonucleic acid comprising HIV genes operatively linked to a transcriptional promoter. In another embodiment of the invention, the polynucleotide vaccine comprises polyribonucleic acid encoding HIV genes which are amenable to translation by the eukaryotic cellular machinery (ribosomes, tRNAs, and other translation factors). Where the protein encoded by the polynucleotide is one which does not normally occur in that animal except in pathological conditions, (i.e. an heterologous protein) such as proteins associated with human immunodeficiency virus, (HIV), the etiologic agent of acquired immune deficiency syndrome, (AIDS), the animals' immune system is activated to launch a protective immune response. Because these exogenous proteins are produced by the animals' own tissues, the expressed proteins are processed by the major histocompatibility system, MHC, in a fashion analogous to when an actual infection with the related organism, HIV, occurs. The result, as shown in this disclosure, is induction of immune responses against the cognate pathogen.

Accordingly, the instant inventors have prepared nucleic acids which, when introduced into the biological system induce the expression of HIV proteins and epitopes. The induced antibody response is both specific for the expressed HIV protein, and neutralizes HIV. In addition, cytotoxic T-lymphocytes which specifically recognize and destroy HIV infected cells are induced. The instant inventors have also developed polynucleotides whereby simian immunodeficiency virus (SIV) genes are efficiently expressed upon introduction in vivo. This achievement is significant because the only animal model closely mimicking the human disease, AIDS, is the subhuman primate model utilizing SIV. Thus, efficacy of the instant immunogens as vaccines can be shown by analogy to the effects obtained in vivo utilizing HIV and SIV polynucleotide immunogens.

There are many embodiments of the instant invention which those skilled in the art can appreciate from the specifics taught herein. Thus, different transcriptional promoters, terminators, carrier vectors or specific gene sequences may be used successfully based on the successful invention disclosed herein.

The instant invention provides a method for using a polynucleotide which, upon introduction into mammalian tissue, induces the co-expression in a single cell, in vivo, of two or more different, discrete gene products. The method is exemplified by using an HIV model which demonstrates the co-expression of more than one gene product in a single cell upon introduction of the polynucleotide into mammalian tissue in vivo. The model is stringent because certain HIV genes contain a sequence known as the REV responsive element (RRE). These genes are not efficiently expressed unless another HIV gene, known as REV, is also present within the cell expressing the RRE-containing HIV gene. This phenomenon is described as REV dependence.

Pavlakis and Felber, WO 93/20212 have described a method of eliminating sequences which may induce transcript instability, which may also achieve some REV independence of certain HIV genes. That method may not be generally applicable to all such genes, is time-consuming and may require multiple gene modifications. Furthermore, the level of expression and immunogenicity of such genes may be compromised by elimination of the REV dependence.

The instant invention provides a different solution which does not require multiple manipulations of REV dependent HIV genes to obtain REV-independence. In addition, the instant invention is applicable to expression of REV independent genes as well as to expression of REV dependent genes. The REV-dependent expression system described herein, is useful in its own right and is also useful as a stringent system for demonstrating the co-expression in a single cell in vivo of more than a single desired gene-product. Thus, in any circumstance in which it is beneficial to achieve the co-expression, within a given cell in vivo, of more than a single gene product, the methods and polynucleotide constructs described herein may be employed.

One situation, exemplified herein, is the co-expression of an immunogenic epitope and a member of the family of T-cell recognition elements known as B7. Recently, Steven Edgington [*Biotechnology* 11:117–1119, 1993] reviewed the coordinate roles of B7 and the major histocompatibility complex (MHC) presentation of epitopes on the surface of antigen presenting cells in activating $CD8^+$ CTLs for the elimination of tumors. Once a MHC molecule on the surface of an antigen presenting cell (APC) presents an epitope to a T-cell receptor (TCR), B7 expressed on the surface of the same APC acts as a second signal by binding to CTLA-4 or CD28. The result is rapid division of $CD4^+$ helper T-cells which signal $CD8^+$ T-cells to proliferate and kill the APC. Thus, our demonstration herein of efficient expression and production of immune responses against an HIV REV dependent gene containing an RRE by coordinately expressing a gene for REV, conclusively proves that more than one gene can be coordinately expressed by introducing a polynucleotide encoding two and even three cistrons (defined as a stretch of nucleic acid that carries the information for a polypeptide chain).

Because many of the applications of the instant invention apply to anti-viral vaccination, the polynucleotides are frequently referred to as a polynucleotide vaccine (PNV). This is not to say that additional utilities of these polynucleotides, in immune stimulation and in anti-tumor therapeutics, is to be ignored or considered to be outside the scope of the invention.

In one embodiment of this invention, a gene encoding an HIV gene product is incorporated in an expression vector. The vector contains a transcriptional promoter recognized by an eukaryotic RNA polymerase, and a transcriptional terminator at the end of the HIV gene coding sequence. In a preferred embodiment, the promoter is the cytomegalovirus promoter with the intron A sequence (CMV-intA), although those skilled in the art will recognize that any of a number of other known promoters such as the strong immunoglobulin, or other eukaryotic gene promoters may be used. A preferred transcriptional terminator is the bovine growth hormone terminator. The combination of CMVintA-BGH terminator (FIG. 8, SEQ. ID:13:) is particularly preferred. In addition, to assist in preparation of the polynucleotides in prokaryotic cells, an antibiotic resistance marker is also preferably included in the expression vector under transcriptional control of a prokaryotic promoter so that expression of the antibiotic does not occur in eukaryotic cells. Ampicillin resistance genes, neomycin resistance genes or any other pharmaceutically acceptable antibiotic resistance marker may be used. In a preferred embodiment of this invention, the antibiotic resistance gene encodes a gene product for neomycin resistance. Further, to aid in the high level production of the polynucleotide by fermentation in prokaryotic organisms, it is advantageous for the vector to contain a prokaryotic origin of replication and be of high copy number. Any of a number of commercially available prokaryotic cloning vectors provide these benefits. In a preferred embodiment of this invention, these functionalities are provided by the commercially available vectors known as pUC. It is desirable, however, to remove non-essential DNA sequences. Thus, the lacZ and lacI coding sequences of pUC are removed in one embodiment of the invention. It is also desirable that the vectors not be able to replicate in eukaryotic cells. This minimizes the risk of integration of polynucleotide vaccine sequences into the recipients' genome.

In another embodiment, the expression vector pnRSV is used, wherein the Rous Sarcoma virus (RSV) long terminal repeat (LTR) is used as the promoter. In yet another embodiment, V 1, a mutated pBR322 vector into which the CMV promoter and the BGH transcriptional terminator were cloned is used. In a particularly preferred embodiment of this invention, the elements of V1 and pUC19 have been combined to produce an expression vector named V1J (SEQ. ID: 12:). Into V1J or another desirable expression vector is cloned an HIV gene, such as gp120, gp41, gp160, gag, pol, env, or any other HIV gene which can induce anti-HIV immune responses (antibody and/or CTLs). Exclusion of functional reverse transcriptase and integrase functions encoded by the HIV genome is desirable to minimize the risk of integration of the polynucleotide vaccine encoded sequences into the recipients' genome. In another embodiment, the ampicillin resistance gene is removed from V1J and replaced with a neomycin resistance gene, to generate V1J-neo (SEQ.ID:14:), into which any of a number of different HIV genes have been cloned for use according to this invention. In yet another embodiment, the vector is V1Jns, which is the same as V1Jneo except that a unique SfiI restriction site has been engineered into the single KpnI site at position 2114 of V1J-neo. The incidence of SfiI sites in human genomic DNA is very low (approximately 1 site per 100,000 bases). Thus, this vector allows careful monitoring for expression vector integration into host DNA, simply by SfiI digestion of extracted genomic DNA. In a further refinement, the vector is V1R. In this vector, as much non-essential DNA as possible was "trimmed" from the vector to produce a highly compact vector. This vector is a derivative of V1Jns and is shown in FIG. 11, (SEQ.ID.: 100:). This vector allows larger inserts to be used, with less concern that undesirable sequences are encoded and optimizes uptake by cells when the construct encoding specific influenza virus genes is introduced into surrounding tissue. In FIG. 11, the portions of V1Jneo (FIG. 7) that are deleted are shown as a gap, and inserted sequence is in bold text, but the numbering of V1Jneo is unchanged. The foregoing vector modification and development procedures may be accomplished according to methods known by those skilled in the art. The particular products described however, though obtained by conventional means, are especially useful for the particular purpose to which they are adapted.

One embodiment of this invention incorporates genes encoding HIV gp160, gp120, gag and other gene products from such well known laboratory adapted strains of HIV as SF2, IIIB or MN, for which a great deal of data has been generated, for example, such as showing that chimpanzees can be protected from a lethal challenge of HIV IIIB virus by first administering HIV IIIb V3 loop specific monoclonal antibody [Emini et al., Nature 355: 728–730 1992], or by vaccination with recombinant gp120 but not gp160 [Berman et al., Nature 345: 822–825, 1990]. Those skilled in the art will recognize that the use of genes from HIV-2 strains having analogous function to the genes from HIV-1 would be expected to generate immune responses analogous to those described herein for HIV-1 constructs. The cloning and manipulation methods for obtaining these genes are well known to those skilled in the art.

There has recently been recognition that elicitation of immune responses against laboratory adapted strains of HIV may not be adequate to provide neutralization of primary, field isolates of HIV, [see for example Cohen, J., Science 262: 980–981, 1993]. Thus, in another embodiment of this invention, genes from virulent, primary field isolates of HIV are incorporated in the polynucleotide immunogen. This is accomplished by preparing cDNA copies of the viral genes and then subcloning the individual genes into the polynucleotide immunogen. Sequences for many genes of many HIV strains are now publicly available on GENBANK and such primary, filed isolates of HIV are available from the National Institute of Allergy and Infectious Diseases (NIAID) which has contracted with Quality Biological, Inc., [7581 Lindbergh Drive, Gaithersburg, Md. 20879] to make these strains available. Such strains are also now available from the World Health Organization (WHO) [Network for HIV Isolation and Characterization, Vaccine Development Unit, Office of Research, Global Program on AIDS, CH-1211 Geneva 27, Switzerland]. From this work those skilled in the art will recognize that one of the utilities of the instant invention is to provide a system for in vivo as well as in vitro testing and analysis so that a correlation of HIV sequence diversity with serology of HIV neutralization, as well as other parameters can be made. The isolation and cloning of these various genes may be accomplished according to methods known to those skilled in the art. Thus this invention further provides a method for systematic identification of HIV strains and sequences for vaccine production. Incorporation of genes from primary isolates of HIV strains provides an immunogen which induces immune responses against clinical isolates of the virus and thus meets a need as yet unmet in the field. Furthermore, as the virulent isolates change, the immunogen may be modified to reflect new sequences as necessary.

To keep the terminology consistent, the following convention is followed herein for describing polynucleotide immunogen constructs:

"Vector name-HIV strain-gene-additional elements". Thus, a construct wherein the gp160 gene of the MN strain is cloned into the expression vector V1Jneo, the name it is given herein is: "V1Jneo-MN-gp160". The additional elements that are added to the construct are described in further detail below. Naturally, as the etiologic strain of the virus changes, the precise gene which is optimal for incorporation in the pharmaceutical may be changed. However, as is demonstrated below, because cytotoxic lymphocyte responses are induced which are capable of protecting against heterologous strains, the strain variability is less critical in the immunogen and vaccines of this invention, as compared with the whole virus or subunit polypeptide based vaccines. In addition, because the pharmaceutical is easily manipulated to insert a new gene, this is an adjustment which is easily made by the standard techniques of molecular biology.

To provide a complete description of the instant invention, the following background on HIV is provided. The human immunodeficiency virus has a ribonucleic acid (RNA) genome, the structure of which is represented in FIG. 1. This RNA genome must be reverse transcribed according to methods known in the art in order to produce a cDNA copy for cloning and manipulation according to the methods taught herein. At each end of the genome is a long terminal repeat which acts as a promoter. Between these termini, the genome encodes, in various reading frames, gag-pol-env as the major gene products: gag is the group specific antigen; pol is the reverse transcriptase, or polymerase; also encoded by this region, in an alternate reading frame, is the viral protease which is responsible for post-translational processing, for example, of gp160 into gp120 and gp41; env is the envelope protein; vif is the virion infectivity factor; REV is the regulator of virion protein expression; neg is the negative regulatory factor; vpu is the virion productivity factor "u"; tat is the trans-activator of transcription; vpr is the viral protein r. The function of each of these elements has been described (see AIDS 89, A Practical Synopsis of the V International Conference, Jun. 4–9, 1989, Montreal, A Philadelphia Sciences Group Publication, from which FIG. 1 was adapted).

In one embodiment of this invention, a gene encoding an HIV or SIV protein is directly linked to a transcriptional promoter. The env gene encodes a large, membrane bound protein, gp160, which is post-translationally modified to gp41 and gp120. The gp120 gene may be placed under the control of the cytomegalovirus promoter for expression. However, gp120 is not membrane bound and therefore, upon expression, it may be secreted from the cell. As HIV tends to remain dormant in infected cells, it is desirable that immune responses directed at cell-bound HIV epitopes also be generated. This goal is accomplished herein by expression in vivo of the cell-membrane associated epitope, gp160, to prime the immune system. However, expression of gp160 is repressed in the absence of REV due to non-export from the nucleus of non-spliced genes. For an understanding of this system, the life cycle of HIV must be described in further detail.

In the life cycle of HIV, upon infection of a host cell, HIV RNA genome is reverse-transcribed into a proviral DNA which integrates into host genomic DNA as a single transcriptional unit. The LTR provides the promoter which transcribes HIV genes from the 5' to 3' direction (gag, pol, env), to form an unspliced transcript of the entire genome. The unspliced transcript functions as the mRNA from which gag and pol are translated, while limited splicing must occur for translation of env encoded genes. For the regulatory gene product REV to be expressed, more than one splicing event must occur because in the genomic setting, REV and env, as is shown in FIG. 1, overlap. In order for transcription of env to occur, REV transcription must stop, and vice versa. In addition, the presence of REV is required for export of unspliced RNA from the nucleus. For REV to function in this manner, however, a REV responsive element (RRE) must be present on the transcript [Malim et al., Nature 338:254–257 (1989)].

In the polynucleotide vaccine of this invention, the obligatory splicing of certain HIV genes is eliminated by providing fully spliced genes (i.e.: the provision of a complete open reading frame for the desired gene product without the need for switches in the reading frame or elimination of noncoding regions; those of ordinary skill in the art would recognize that when splicing a particular gene, there is some latitude in the precise sequence that results; however so long as a functional coding sequence is obtained, this is acceptable). Thus, in one embodiment, the entire coding sequence for gp160 is spliced, and the sequence of REV is spliced, such that no intermittent expression of each gene product is required. Furthermore, the features of REV regulated expression are exploited to optimize expression of HIV encoded REV-dependent, immunogenic gene products.

For REV to function as an exporter of transcripts from the nucleus to be translated in the cytoplasm, REV requires, in addition to the presence of a REV responsive element (RRE) on the transcript to be exported, at least one splice donor site on the 5' side of the gene containing the RRE [Lu et al., P.N.A.S. USA 87:7598–7602, (October 1990); Chang and Sharp, Cell 59:789–795 (Dec. 1, 1989)]. The instant inventors conceived polynucleotides providing the REV coding sequence in a location on the same expression vector as the gene to be expressed such that co-expression of REV and the REV responsive gene occur without the need for any splicing. Thus, in a preferred embodiment of this invention, HIV genes are placed immediately downstream from a transcriptional promoter, such as the CMV promoter, and the spliced REV coding sequence is placed at a location 3' to (also referred to as downstream from) the first coding sequence. Naturally, the order of these genes could be changed. However, it may be preferable to have the immunogenic HIV cistron abut directly to the transcriptional promoter to ensure that all transcripts produced encode the entire cistron.

One method for achieving co-expression of genes relies on co-transfection of cells in culture with different vectors expressing different genes. For a REV dependent gene, the REV gene product could be provided in this manner in trans. However, this is suboptimal for the purposes of this invention, although not outside the scope of the instant invention, because of the low probability that co-transfection of a given cell would occur in vivo so as to achieve the necessary availability of REV for vigorous expression of REV dependent immunogenic HIV gene products. Another method is to provide several promoters on a given vector, each promoter controlling expression of a separate gene. This amounts to providing REV gene product in cis. This solution may be employed according to the instant invention. In such an embodiment, it would be preferable for the various promoters and the genes they control to run in opposite directions. However, because of the known competitive interference between promoters in this type of multiple gene vector, this embodiment is also considered sub-optimal.

Ghattas et al., [Mol. and Cell. Biol. 11, No. 12:5848–5859 (Dec. 1991)], Kaufaman et al. [Nuc. Acids Res. 19, No. 16:4485–4490 (1991)], and Davies [J. Virol. 66, No. 4:1924–1932 (April 1992)] have described an internal ribosome entry site (IRES) in the encephalomyocarditis virus (EMCV) leader. They reported that a system in which an upstream promoter could be used to initiate transcription of a dicistronic mRNA provides good expression of both the 5' and 3' open reading frames when an IRES is located between the two genes. Chen et al. (J. Viral., 67: 2142–2145, 1993] have reported a system in which the 5 nontranslated region (NTR) from swine vesicular disease virus (SVDV) was used to construct a bicistronic virus for the coexpression of two genes from one transcript from an infectious viral vector.

Figure 2:
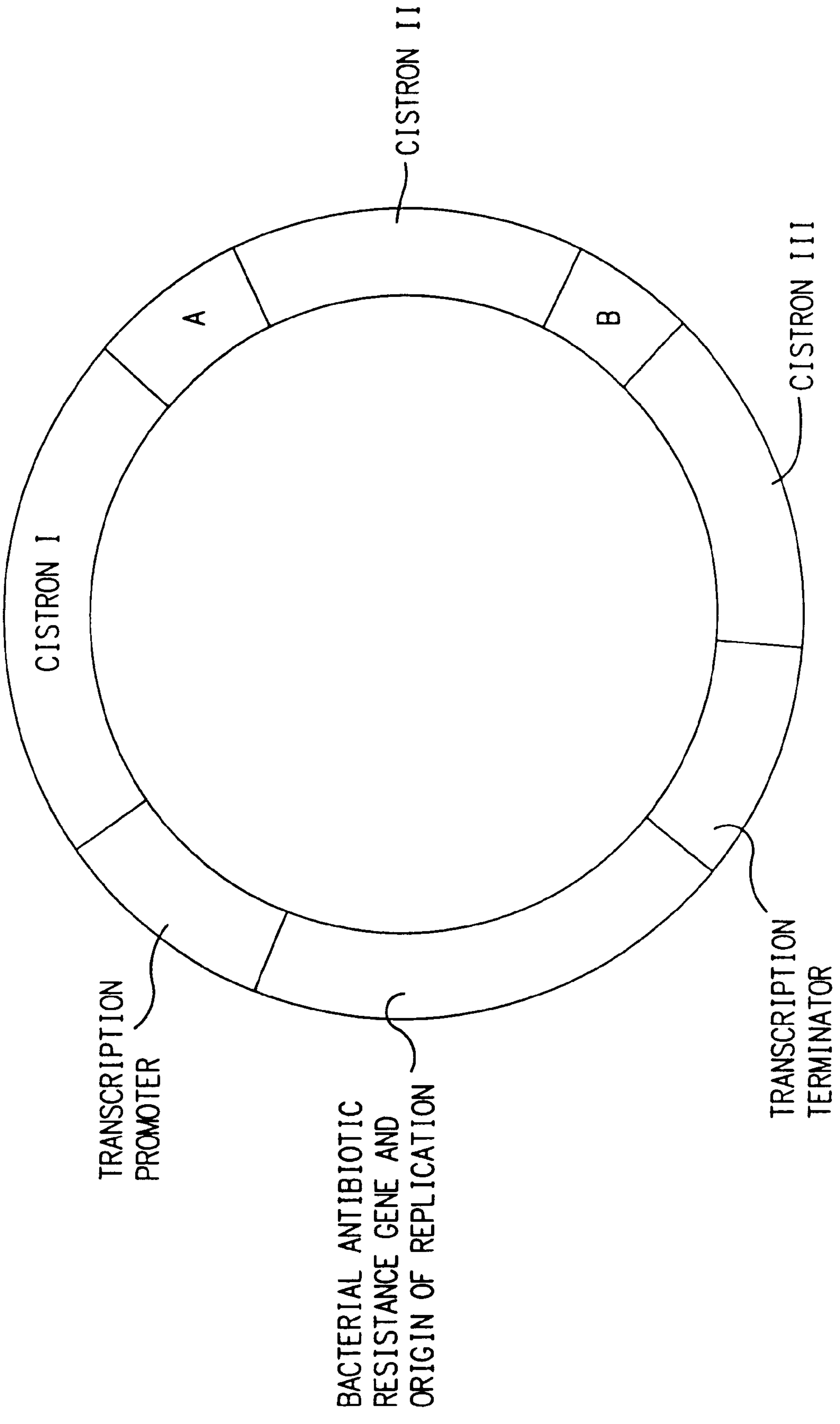
FIG. 2. A schematic representation of a polynucleotide construct of this invention capable of inducing the co-ordinate expression in vivo in a single cell of up to three gene products encoded by each of three cistrons (I, II, and III). The segments A and B represent control sequences including transcription termination signals and promoters or internal ribosome entry sites (IRES).
Figure 3:
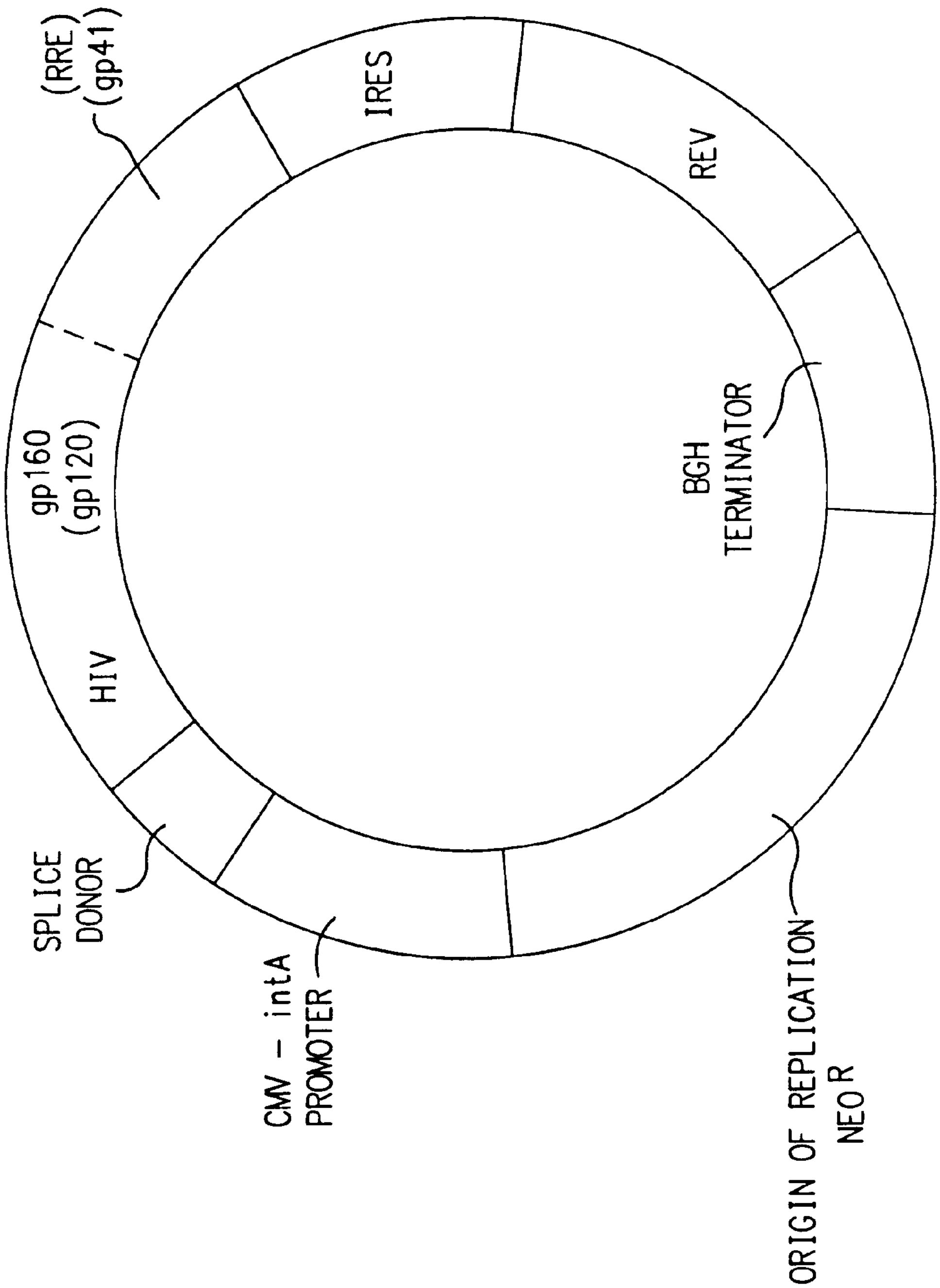
FIG. 3. Detailed schematic of an HIV env polynucleotide immunogen construct comprising the CMV-intA transcription promoter, a 5'-splice donor, HIV gp160 (showing gp120, gp41, and the REV-responsive element, RRE), an internal ribosome entry site (IRES), the REV cistron, the BGH transcription terminator, and the neomycin resistance marker which is driven by a prokaryotic transcription promoter.

The instant inventors have discovered that a nucleic acid construct which incorporates coordinated expression of an HIV gene containing a REV responsive element (RRE), an internal ribosome entry site (IRES) and a REV coding sequence results in efficient expression of both REV and the REV dependent gene product. This embodiment of the invention is better understood with reference to FIGS. 2 and 3. FIG. 2 shows a generalized embodiment while, FIG. 3, shows a specific embodiment of this invention which, according to the nomenclature system described above, is V1Jns-gp160 (RRE)-IRES-REV. The strain of HIV from which the immunogenic HIV gene is derived is irrelevant for the illustrative purposes of this discussion, and indeed, the expression of any REV dependent gene product is predictably efficient, as is the elicitation of immune responses against both REV and the REV dependent gene product, based on the instant patent disclosure. According to the embodiment shown in FIG. 3, the vector is V1Jns, described above. Thus, the promoter (CMVintA) and terminator (BGH) are provided for by the vector, along with a prokaryotic origin of replication, to facilitate large scale production of the HIV polynucleotide vaccine through fermentation of bacteria transformed with the construct, according to methods well known in the art. This construct does not replicate in eukaryotic tissue, due to the absence of an eukaryotic origin of replication. A splice donor site from the naturally occurring rev/tat splice donor is provided (rev/tat SD) immediately preceding the HIV gene. The gag/pol/env coding sequence contains or is followed by a REV responsive element (RRE) which, upon formation of the nascent transcript, provides the necessary signals for REV binding to and export of the REV dependent mRNA from the nucleus. Next, there are sequences provided for reinitiation of translation at the internal ribosome entry site (IRES) so that the downstream REV coding sequence is efficiently translated. In this manner, REV gene product is provided in cis, on the same polynucleotide as a REV dependent gene product.

In further refinements to the instant invention, a third cistron may be included in the PNV. The genes encoding such immunostimulatory proteins as the B7-antigen presenting cell-surface protein, the human granulocyte/monocyte colony stimulatory factor (GM-CSF) gene, and cytokine genes such as interleukin and interferon, the use of tissue-specific transcriptional promoters and enhancers, are all contemplated. The provision of B7 or GM-CSF gene in cis, either by insertion of an IRES after REV and before the B7 gene, by provision of a second promoter on the same vector construct as the dicistronic REV-dependent HIV gene, IRES-REV construct, or in trans using a separate construct are all envisioned by extension of the foregoing teachings regarding REV and REV dependent genes. The generalized immuno-stimulatory effect of these gene products may be sufficient even if provided in trans to enhance immune responses against the HIV gene products encoded by the immunogen of this invention. It is preferable, particularly for B7, that the same cell presenting HIV epitopes in the cleft of MHC-I molecules also present B7. This co-presentation of both the antigenic epitope and B7 "closes" the switch necessary for T-cell activation. Cytokines, particularly L-12, which modifies whether a predominant humoral or cellular immune response is mounted [see Afonso et al., *Science* 263:235–237, 1994], either is provided intravenously at the same time that PNV is introduced, or is included as a third cistron in the PNV, thereby assuring localized production of the interleukin. The genes for these immunostimulatory and immunoregulatory proteins, including GM-CSF (see Shaw and Kamen, *Cell* 46:659–667, 1986), interleukin-12 (see Wolf, S., et al., *J. Immunol.* 146:3074–3081, 1991) and B7, (see Gordon et al., *J. Immunol.* 143:2714–2722, 1989; for clones and sequences of newer members of the B7 family of proteins, see also Azuma, M., et al., *Nature* 366:76–79, 1993; and Freeman, G., et al., *Science* 262:909–911, 1993) are known and easily cloned and incorporated in PNV's according to this invention using methods known to the skilled practitioner. Preferably, the genes used for these purposes are the human genes so that immune responses against these proteins are minimized, allowing the expressed proteins to carry out their immunomodulatory and immunostimulatory functions. Where HIV genes have been rendered REV-independent, the REV cistron may be eliminated completely and a second cistron encoding a B7 gene family member and a third cistron encoding yet another gene-product such as IL-12, may be constructed.

The use of tissue-specific promoters or enhancers, for example the muscle creatine kinase (MCK) enhancer element, is desirable whenever it is desirable to limit expression of the polynucleotide to a particular tissue type. For example, myocytes are terminally differentiated cells which do not divide. Integration of foreign DNA into chromosomes appears to require both cell division and protein synthesis. Thus, limiting protein expression to non-dividing cells such as myocytes is preferable. However, use of the CMV promoter is adequate for achieving expression in many tissues into which the PNV is introduced.

In the various embodiments of this invention which are described below, the basic paradigm described above is used. Deviations, additions or subtractions from this basic construction design serve to hi-light the various aspects of this invention.

This patent disclosure exemplifies bi- or tri-cistronic HIV polynucleotide immunogens as polynucleotide vaccines, PNVs, to generate humoral immunity as well as cross-strain cellular antiviral immunity. The system is useful, however, for any two or three cistrons, whether or not related to HIV, when co-expression of the encoded gene products in a single cell in vivo is required. However, the dual humoral and cellular immune responses generated according to this invention are particularly significant to inhibiting HIV infection, given the propensity of HIV to mutate within the infected population, as well as in infected individuals. In order to formulate an effective protective vaccine for HIV it is desirable to generate both a multivalent antibody response for example to gp160 (env is approximately 80% conserved across various HIV-1, lade B strains, which are the prevalent strains in US human populations), the principal neutralization target on HIV, as well as cytotoxic T cells reactive to the conserved portions of gp160 and, internal viral proteins encoded by gag. We have made an HIV vaccine comprising gp160 genes selected from common laboratory strains; from predominant, primary viral isolates found within the infected population; from mutated gp160s designed to unmask cross-strain, neutralizing antibody epitopes; from other representative HIV genes such as the gag gene (≧95% conserved across HIV isolates); and from SIV, which provides an animal model for testing the HIV PNV wherein non-human primates can be immunized and challenged to test viral load and progression to disease.

Virtually all HIV seropositive patients who have not advanced towards an immunodeficient state harbor anti-gag CTLs while about 60% of these patients show cross-strain, gp160-specific CTLs. The amount of HIV specific CTLs found in infected individuals that have progressed on to the disease state known as AIDS, however, is much lower, demonstrating the significance of our findings that we can induce cross-strain CTL responses. Because HIV late gene expression is REV dependent our gp160 and gag vaccination vectors are designed to also produce REV (~90% conserved), to facilitate the REV-dependent gene expression. An additional benefit of this invention is that anti-REV immune responses are also generated. This gives further advantage to our vaccine because REV is made in large quantities very early following infection of a cell, and hours in advance of synthesis of the late gene products, thereby providing an earlier opportunity for intervention by vaccine-induced T-cell responses including CTLs and T-helper cells.

In a further embodiment of this invention, a cocktail vaccine is prepared in which different HIV REV-dependent gene constructs are mixed together to generate anti-REV CTL responses in addition to antibodies and CTL against the immunogenic HIV REV-dependent gene products. According to this embodiment, one polynucleotide encoding gp160, followed by REV, followed by B7, in a tri-cistronic construct having one promoter and two IRES sequences, is mixed with another polynucleotide encoding a gag gene product, REV, and B7 or another immunomodulatory or immunostimulatory gene product such as IL-12 or GM-CSF. In this fashion, with a single or several injections of polynucleotide, immune responses against several HIV related immunogens can be raised. Likewise, one polynucleotide comprising a REV independent gene product, such as those described in WO 93/20212, B7, and another immunomodulatory or immunostimulatory gene, such as IL-12 or GM-CSF, are mixed with another REV-dependent, or REV-independent bi- or tri-cistronic expression construct. Furthermore, multiple bi- or tri-cistronic constructs encoding HIV or other antigens could be prepared and mixed to produce a multivalent combination polynucleotide vaccine.

Immune responses induced by our env, REV, and gag polynucleotide vaccine constructs are demonstrated in mice, rabbits, and primates. Monitoring antibody production to env in mice allows confirmation that a given construct is suitably immunogenic, i.e., a high proportion of vaccinated animals show an antibody response. Mice also provide the most facile animal model suitable for testing CTL induction by our constructs and are therefore used to evaluate whether a particular construct is able to generate such activity. However, mouse cell lines have been observed to not support efficient REV or tat functions. This observation was made in the context of HIV LTR driven expression of late genes and a limited amount of data indicates that heterologous promoters allow REV function in mouse cells. Rabbits and monkeys (African Green, rhesus, chimpanzees) provide additional species including primates for antibody evaluation in larger, non-rodent animals. These species are also preferred to mice for antisera neutralization assays due to high levels of endogenous neutralizing activities against retroviruses observed in mouse sera.

These data demonstrate that sufficient immunogenicity is engendered by our vaccines to achieve protection in experiments in a chimpanzee/$HIV_{IIIB}$ challenge model. The currently emerging and increasingly accepted definition of protection in the scientific community is moving away from so-called "sterilizing immunity", which indicates complete protection from HIV infection, to prevention of disease. A number of correlates of this goal include reduced blood viral titer, as measured either by HIV reverse transcriptase activity, by infectivity of samples of serum, by ELISA assay of p24 or other HIV antigen concentration in blood, increased $CD4^+$ T-cell concentration, and by extended survival rates [see, for example, Cohen, J., *Science* 262:1820–1821, 1993, for a discussion of the evolving definition of anti-HIV vaccine efficacy]. The immunogens of the instant invention also generate neutralizing immune responses against infectious (clinical, primary field) isolates of HIV.

Immunology

A. Antibody Responses to env.

1. gp160 and gp120. An ELISA assay is used to determine whether vaccine vectors expressing either secreted gp 120 or membrane-bound gp160 are efficacious for production of env-specific antibodies. Initial in vitro characterization of env expression by our vaccination vectors is provided by immunoblot analysis of gp160 transfected cell lysates. These data confirm and quantitate gp160 expression using anti-gp41 and anti-gp120 monoclonal antibodies to visualize transfectant cell gp160 expression. In one embodiment of this invention, gp160 is preferred to gp120 for the following reasons: (1) an initial gp120 vector gave inconsistent immunogenicity in mice and was very poorly or non-responsive in African Green Monkeys; (2) gp160 contributes additional neutralizing antibody as well as CTL epitopes by providing the addition of approximately 190 amino acid residues due to the inclusion of gp41; (3) gp160 expression is more similar to viral env with respect to tetramer assembly and overall conformation; and (4) we find that, like the success of membrane-bound, influenza HA constructs for producing neutralizing antibody responses in mice, ferrets, and non-human primates [see Ulmer et al., Science 259:1745–1749, 1993; Montgomery, D., et al., *DNA and Cell Biol.* 12:777–783, 1993] anti-gp160 antibody generation is superior to anti-gp120 antibody generation. Selection of which type of env, or whether a cocktail of env subfragments, is preferred is determined by the experiments outlined below.

2. Presence and Breadth of Neutralizing Activity. ELISA positive antisera from rabbits and monkeys is tested and shown to neutralize both homologous and heterologous HIV strains.

3. V3 vs. non-V3 Neutralizing Antibodies. A major goal for env PNVs is to generate broadly neutralizing antibodies. It has now been shown that antibodies directed against V3 loops are very strain specific, and the serology of this response has been used to define strains.

a. Non-V3 neutralizing antibodies appear to primarily recognize discontinuous, structural epitopes within gp120 which are responsible for CD4 binding. Antibodies to this domain are polyclonal and more broadly cross-neutralizing probably due to restraints on mutations imposed by the need for the virus to bind its cellular ligand. An in vitro assay is used to test for blocking gp120 binding to CD4 immobilized on 96 well plates by sera from immunized animals. A second in vitro assay detects direct antibody binding to synthetic peptides representing selected V3 domains immobilized on plastic. These assays are compatible for antisera from any of the animal types used in our studies and define the types of neutralizing antibodies our vaccines have generated as well as provide an in vitro correlate to virus neutralization.

b. gp41 harbors at least one major neutralization determinant, corresponding to the highly conserved linear epitope recognized by the broadly neutralizing 2F5 monoclonal antibody (commercially available from Viral Testing Systems Corp., Texas Commerce Tower, 600 Travis Street, Suite 4750, Houston, Tex. 77002–3005(USA), or Waldheim Pharmazeutika GmbH, Boltzmangasse 11, A-1091 Wien, Austria), as well as other potential sites including the well-conserved "fusion peptide" domain located at the N-terminus of gp41. Besides the detection of antibodies directed against gp41 by immunoblot as described above, an in vitro assay test is used for antibodies which bind to synthetic peptides representing these domains immobilized on plastic.

4. Maturation of the Antibody Response. In HIV seropositive patients, the neutralizing antibody responses progress from chiefly anti-V3 to include more broadly neutralizing antibodies comprising the structural gp120 domain epitopes described above (#3), including gp41 epitopes. These types of antibody responses are monitored over the course of both time and subsequent vaccinations.

B. T Cell Reactivities Against env, REV, net and gag.

1. Generation of CTL Responses. Viral proteins which are synthesized within cells give rise to MHC I-restricted CTL responses. Each of these proteins elicit CTL in seropositive patients. Our vaccines also are able to elicit CTL in mice. The immunogenetics of mouse strains are conducive to such studies, as demonstrated with influenza NP, [see Ulmer et al., Science 259:1745–1749, 1993]. Several epitopes have been defined for the HIV proteins env, REV, nef and gag in Balb/c mice, thus facilitating in vitro CTL culture and cytotoxicity assays. Additionally, it is advantageous to use syngenic tumor lines, such as the murine mastocytoma P815, transfected with these genes to provide targets for CTL as well as for in vitro antigen specific restimulation. Methods for defining immunogens capable of eliciting MHC class I-restricted cytotoxic T lymphocytes are known [see Calin-Laurens, et al., *Vaccine* 11(9):974–978, 1993; see particularly Eriksson, et al., *Vaccine* 11(8):859–865, 1993, wherein T-cell activating epitopes on the HIV gp120 were mapped in primates and several regions, including gp120 amino acids 142–192, 296–343, 367400, and 410–453 were each found to induce lymphoproliferation; furthermore, discrete regions 248–269 and 270–295 were lymphoproliferative. A peptide encompassing amino acids 152–176 was also found to induce HIV neutralizing antibodies], and these methods may be used to identify immunogenic epitopes for inclusion in the PNV of this invention. Alternatively, the entire gene encoding gp160, gp120, protease, or gag could be used. For additional review on this subject, see for example, Shirai et al., *J. Immunol* 148:1657–1667, 1992; Choppin et al., *J. Immunol* 147:569–574, 1991; Choppin et al., *J. Immunol* 147:575–583, 1991; Berzofsky et al., *J. Clin. Invest.* 98:876–884, 1991. As used herein, T-cell effector function is associated with mature T-cell phenotype, for example, cytotoxicity, cytokine secretion for B-cell activation, and/or recruitment or stimulation of macrophages and neutrophils.

2. Measurement of $T_H$ Activities. Spleen cell cultures derived from vaccinated animals are tested for recall to specific antigens by addition of either recombinant protein or peptide epitopes. Activation of T cells by such antigens, presented by accompanying splenic antigen presenting cells, APCs, is monitored by proliferation of these cultures or by cytokine production. The pattern of cytokine production also allows classification of TH response as type 1 or type 2. Because dominant $T_H2$ responses appear to correlate with the exclusion of cellular immunity in immunocompromised seropositive patients, it is possible to define the type of response engendered by a given PNV in patients, permitting manipulation of the resulting immune responses.

3. Delayed Type Hypersensitivity (DTH). DTH to viral antigen after i.d. injection is indicative of cellular, primarily MHC II-restricted, immunity. Because of the commercial availability of recombinant HIV proteins and synthetic peptides for known epitopes, DTH responses are easily determined in vaccinated vertebrates using these reagents, thus providing an additional in vivo correlate for inducing cellular immunity.

Protection

Based upon the above immunologic studies, it is predictable that our vaccines are effective in vertebrates against challenge by virulent HIV. These studies are accomplished in an $HIV_{IIIB}$/chimpanzee challenge model after sufficient vaccination of these animals with a PNV construct, or a cocktail of PNV constructs comprised of $gp160_{IIIB}$, $gag_{IIIB}$, $nef_{IIIB}$ and $REV_{IIIB}$. The IIIB strain is useful in this regard as the chimpanzee titer of lethal doses of this strain has been established. However, the same studies are envisioned using any strain of HIV and the epitopes specific to or heterologous to the given strain. A second vaccination/challenge model, in addition to chimpanzees, is the scid-hu PBL mouse. This model allows testing of the human lymphocyte immune system and our vaccine with subsequent HIV challenge in a mouse host. This system is advantageous as it is easily adapted to use with any HIV strain and it provides evidence of protection against multiple strains of primary field isolates of HIV. A third challenge model utilizes hybrid HIV/SIV viruses (SHIV), some of which have been shown to infect rhesus monkeys and lead to immunodeficiency disease resulting in death [see Li, J., et al., *J. AIDS* 5:639–646, 1992]. Vaccination of rhesus with our polynucleotide vaccine constructs is protective against subsequent challenge with lethal doses of SHIV.

PNV Construct Summary

HIV and other genes are preferably ligated into an expression vector which has been specifically optimized for polynucleotide vaccinations. According to this invention disclosure, methods for producing several such vectors are enabled. Essentially, all extraneous DNA is removed, leaving the essential elements of transcriptional promoter, immunogenic epitopes, and additional cistrons encoding immunoenhancing or immunomodulatory genes, with their own promoters or IRES, transcriptional terminator, bacterial origin of replication and antibiotic resistance gene, as previously described (see FIG. 2). Those skilled in the art will appreciate that introduction of RNA which has been transcribed in vitro to produce the multi-cistronic mRNAs encoded by the DNA counterparts of this invention naturally forms an integral part of this invention. For this purpose, it is desirable to use as the transcriptional promoter such powerful RNA polymerase promoters as the T7 or SP6 promoters, and performing run-on transcription with a linearized DNA template. These methods are well known in the art.

Expression of HIV late genes such as env and gag is REV-dependent and requires that the REV response element (RRE) be present on the viral gene transcript. A secreted form of gp120 can be generated in the absence of REV by substitution of the gp120 leader peptide with a heterologous leader such as from tPA (tissue-type plasminogen activator), and preferably by a leader peptide such as is found in highly expressed mammalian proteins such as immunoglobulin leader peptides. We have inserted a tPA-gp120 chimeric gene into V1Jns which efficiently expresses secreted gp120 in transfected cells (RD, a human rhabdomyosarcoma line). We have also developed an IRES-based (IRES=internal ribosomal entry site) dicistronic V1Jns vector containing both gp160 (which harbors the RRE) and REV which efficiently expresses gp160 in transfected cell lines (293, a human embryonic kidney cell line; and RD). Monocistronic gp160 does not produce any protein upon transfection without the addition of a REV expression vector. Dicistronic gp160/REV produces similar amounts of gp160 as co-transfected gp160 and REV monocistronic vectors. From these studies, it is predictable that dicistronic vectors more efficiently express gp160 following introduction in vivo intramuscularly relative to a mixture of gp160 and REV vectors because the dicistron insures the proximity of gp160 construct and REV within structurally extended, multi-nucleated muscle cells. This dicistronic strategy also supports expression of gag after the inclusion of the RRE within the transcript region of the vector. It also supports the expression of unrelated genes in a bi- or tri-cistronic PNV, such as co-expression of HIV immunogenic epitopes, influenza virus immunogenic epitopes, cancer-related antigens, and immunomodulatory genes such as interleukin, B7 and GM-CSF.

Representative Construct Components Include (But are not Restricted to) (See FIG. 2, Cistrons I, III and III):

1. tPA-$gp120_{MN}$;
2. gp $160_{IIIB}$/IRES/$REV_{IIIB}$;
3. gp $160_{IIB}$;
4. $REV_{IIIB}$;
5. tat/REV/gp160 (a genomic IIIB clone which weakly expresses gp160);
6. REV/gp160;
7. $gp160_{MN}$;
8. gp160 from clinically relevant primary HIV isolates;
9. nef, using the gene from clinically relevant strains;
10. $gag_{IIIB}$: for anti-gag CTL;
11. tPA-$gp120_{IIIB}$: for chimp studies;
12. gp160 with structural mutations: V3 loop substitutions from clinically relevant strains of HIV; several mutations on several constructs such as variable loop removal, Asn mutations to remove steric carbohydrate obstacles to structural, neutralizing antibody epitopes; and CD4 binding site knockout mutants;
13. gp41: to specifically elicit anti-gp41 neutralizing antibodies, particularly the 2F5 monoclonal antibody epitope, located directly anterior to the transmembrane domain, which is broadly conserved across many strains. This peptide is difficult to express in the absence of gp120 and requires several strategies, e.g., a recent report found that the 2F5 epitope spliced into an influenza HA loop tip could elicit HIV neutralizing antibodies; alternatively, provision of appropriate leader sequences, as in the tPA signal peptide leader sequence, allows expression of this gene product;

14. gag: similar to construct from #5 above, using the gene from clinically relevant strains;
15. rev: for gp160 and gag dicistronics;
16. B7 coding sequences;
17. GM-CSF sequences;
18. Interleukin sequences, particularly encoding IL-12;
19. Tumor associated antigens;
20. Genes encoding antigens expressed by pathogens other than HIV, such as, but not limited to, influenza virus nucleoprotein, hemagglutinin, matrix, neuraminidase, and other antigenic proteins; herpes simplex virus genes; human papillomavirus genes; tuberculosis antigens; hepatitis A, B, or C virus antigens; and combinations of these and other antigens to form at least dicistronic constructs which may be combined with multiple other polycistronic constructs to provide a cocktail composition capable of raising immune responses against all of the represented pathogens or tumor antigens.

In the HIV env constructs, those of ordinary skill in the art will recognize the desirability of expressing nucleic acids encoding various env V3 loop amino acid sequences. As an example, any or all of the following amino acid sequences, or portions thereof, may be encoded by HIV polynucleotide immunogens of this invention:

GP160 V3 Loop Sequence Summary for PNV Constructs

North American/European Consensus, SEQ.ID:1:
CysThrArgProAsnAsnAsnThrArgLysSerIleHisIleGlyPro GlyArgAlaPheTyrThrThrGlyGluIleIleGlyAspIleArg GlnAlaHisCys MN, SEQ.ID:2:
CysThrArgProAsnTyrAsnLysArgLysArgIleHisIleGlyPro GlyArgAlaPheTyrThrThrLysAsnIleIleGlyThrIleArg GlnAlaHisCys IIIB (HXB2R), SEQ.ID:3:
CysThrArgProAsnAsnAsnThrArgLysArgIleArgIleGlnArg GlyProGlyArgAlaPheValThrIleGlyLysIleGlyAsnMetArg GlnAlaHisCys 116-v, SEQ.ID:4:
CysThrArgProAsnAsnAsnThrArgLysGlyIleHisIleGlyPro GlyArgAlaPheTyrThrThrGlyLysIleIleGlyAsnIleArgGln AlaHisCys 452-p, SEQ.ID:5:
CysThrArgProSerAsnAsnAsnThrArgLysSerIleHisIleGly ProGlyLysAlaPheTyrAlaThrGlyAlaIleIleGlyAspIleArg GlnAlaHisCys 146-v, SEQ.ID:6:
CysThrArgProAsnAsnAsnThrArgArgSerIleHisIleAlaPro GlyArgAlaPheTyrAlaThrGlyAspIleIleGlyAspIleArg GlnAlaHisCys The protective efficacy of polynucleotide HIV immunogens against subsequent viral challenge is demonstrated by immunization with the non-replicating plasmid DNA of this invention. This is advantageous since no infectious agent is involved, no assembly of virus particles is required, and determinant selection is permitted. Furthermore, because the sequence of gag and protease and several of the other viral gene products is conserved among various strains of HIV, protection against subsequent challenge by a virulent strain of HIV that is homologous to, as well as strains heterologous to the strain from which the cloned gene is obtained, is enabled.

The i.m. injection of a DNA expression vector encoding gp 160 results in the generation of significant protective immunity against subsequent viral challenge. In particular, gp160-specific antibodies and primary CTLs are produced. Immune responses directed against conserved proteins can be effective despite the antigenic shift and drift of the variable envelope proteins. Because each of the HIV gene products exhibit some degree of conservation, and because CTLs are generated in response to intracellular expression and MHC processing, it is predictable that many virus genes give rise to responses analogous to that achieved for gp160. Thus, many of these genes have been cloned, as shown by the cloned and sequenced junctions in the expression vector (see below) such that these constructs are immunogenic agents in available form.

The invention offers a means to induce cross-strain protective immunity without the need for self-replicating agents or adjuvants. In addition, immunization with the instant polynucleotides offers a number of other advantages. First, this approach to vaccination should be applicable to tumors as well as infectious agents, since the $CD8^+$ CTL response is important for both pathophysiological processes [K. Tanaka et al., Annu. Rev. Immunol. 6, 359 (1988)]. Therefore, eliciting an immune response against a protein crucial to the transformation process may be an effective means of cancer protection or immunotherapy. Second, the generation of high titer antibodies against expressed proteins after injection of viral protein and human growth hormone DNA, [see for example D.-c. Tang et al., Nature 356, 152, 1992], indicates this is a facile and highly effective means of making antibody-based vaccines, either separately or in combination with cytotoxic T-lymphocyte vaccines targeted towards conserved antigens.

The ease of producing and purifying DNA constructs compares favorably with traditional protein purification, facilitating the generation of combination vaccines. Thus, multiple constructs, for example encoding gp160, gp120, gp41, or any other HIV gene may be prepared, mixed and co-administered. Finally, because protein expression is maintained following DNA injection [H. Lin et al., Circulation 82, 2217 (1990); R. N. Kitsis et al., Proc. Natl. Acad. Sci. (USA) 88, 4138 (1991); E. Hansen et al., FEBS Lett. 290, 73 (1991); S. Jiao et al., Hum. Gene Therapy 3, 21 (1992); J. A. Wolff et al., Human Mol. Genet. 1, 363 (1992)], the persistence of B- and T-cell memory may be enhanced [D. Gray and P. Matzinger, J. Exp. Med. 174, 969 (1991); S. Oehen et al., ibid. 176, 1273 (1992)], thereby engendering long-lived humoral and cell-mediated immunity.

The standard techniques of molecular biology for preparing and purifying DNA constructs enable the preparation of the DNA immunogens of this invention. While standard techniques of molecular biology are therefore sufficient for the production of the products of this invention, the specific constructs disclosed herein provide polynucleotide immunogens which surprisingly produce cross-strain and primary HIV isolate neutralization, a result heretofore unattainable with standard inactivated whole virus or subunit protein vaccines.

The amount of expressible DNA or transcribed RNA to be introduced into a vaccine recipient will depend on the strength of the transcriptional and translational promoters used and on the immunogenicity of the expressed gene product. In general, an immunologically or prophylactically effective dose of about 1 ng to 100 mg, and preferably about 10 $\mu$g to 300 $\mu$g is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided. Following vaccination with HIV polynucleotide immunogen, boosting with HIV protein immunogens such as gp160, gp120, and gag gene products is also contemplated. Parenteral administration, such as intravenous, intramuscular, subcutaneous or other means of administration of interleukin-12 protein, concurrently with or subsequent to parenteral introduction of the PNV of this invention also advantageous.

The polynucleotide may be naked, that is, unassociated with any proteins, adjuvants or other agents which impact on the recipients' immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used to advantage. These agents are generally referred to herein as transfection facilitating reagents and pharmaceutically acceptable carriers. Techniques for coating microprojectiles coated with polynucleotide are known in the art and are also useful in connection with this invention.

Accordingly, one embodiment of this invention is a polynucleotide which, upon introduction into mammalian tissue, induces the co-expression in a single cell, in vivo, of two or three different, discrete gene products, comprising:

a first transcriptional promoter which operates efficiently in eukaryotic cells upstream from and in transcriptional control of a first cistron;

a second cistron downstream from the first cistron, under transcriptional control either of the first transcriptional promoter, or under control of a second transcriptional promoter;

optionally, a third cistron downstream from the second cistron, under transcriptional control either of the first transcriptional promoter, under control of a second transcriptional promoter, or under control of a third transcriptional promoter;

a transcriptional terminator following each of the first, second and third cistron, unless followed by another citron lacking its own transcriptional promoter.

In another embodiment, the invention is a polynucleotide which comprises contiguous nucleic acid sequences which cannot replicate in eukaryotic cells but which are capable of being expressed to produce a gene product upon introduction of the polynucleotide into eukaryotic tissues in vivo. The encoded gene product preferably either acts as an immunostimulant or as an antigen capable of generating an immune response. Thus, the nucleic acid sequences in this embodiment encode a spliced REV gene, a human immunodeficiency virus (HIV) immunogenic epitope, and optionally, a cytokine or a T-cell costimulatory element, such as a member of the B7 family of proteins.

In another embodiment, the invention is a method for co-expression in a single cell, in vivo, of two or three different, discrete gene products, which comprises introducing between about 0.1 $\mu$g and 100 mg of a polynucleotide of this invention into the tissue of the vertebrate.

In another embodiment, the invention is a method for using a REV dependent HIV gene to induce immune responses in vivo which comprises:

a) isolating the REV dependent HIV gene;

b) linking the isolated gene to regulatory sequences such that the gene is expressible by virtue of being operatively linked to control sequences which, when introduced into a living tissue, direct the transcription initiation and subsequent translation of the gene;

c) introducing the expressible gene into a living tissue;

d) introducing a gene encoding HIV REV either in trans or in cis to the HIV REV dependent gene; and e) optionally, boosting with additional expressible HIV gene.

A further embodiment of this invention amounts to a method of inducing an antigen presenting cell to stimulate cytotoxic T-cell proliferation specific to HIV antigens. This involves exposing cells of a vertebrate in vivo to a polynucleotide which consists of an antigenic HIV epitope, REV if the antigenic HIV epitope depends on REV for efficient expression, and B7 encoding sequences.

The following examples are provided to further define the invention, without limiting the invention to the specifics of the examples.

Materials descriptions

Vectors pF411 and pF412: These vectors were subcloned from vector pSP62 which was constructed in R. Gallo's lab. pSP62 is an available reagent from Biotech Research Laboratories, Inc. pSP62 has a 12.5 kb XbaI fragment of the HXB2 genome subcloned from lambda HXB2. SalI and Xba I digestion of pSP62 yields to HXB2 fragments: 5'-XbaI/SalI, 6.5 kb and 3'-SalI/XbaI, 6 kb. These inserts were subcloned into pUC 18 at SmaI and SalI sites yielding pF411 (5'-XbaI/SalI) and pF412 (3'-XbaI/SalI). pF411 contains gag/pol and pF412 contains tat/rev/env/nef.

Repligen Reagents:

recombinant rev (IIIB), #RP1024-10 rec. gp120 (IIIB), #RP1001-10 anti-rev monoclonal antibody, #RP1029-10 anti-gp120 mAB, #1C1, #RP1010-10

AIDS Research and Reference Reagent Program:

anti-gp41 mAB hybridoma, Chessie 8, #526

EXAMPLE 1

Vectors for Vaccine Production

A) V1: The expression vector V1 was constructed from pCMVIE-AKI-DHFR [Y. Whang et al., J. Virol. 61, 1796 (1987)]. The AKI and DHFR genes were removed by cutting the vector with EcoR I and self-ligating. This vector does not contain intron A in the CMV promoter, so it was added as a PCR fragment that had a deleted internal Sac I site [at 1855 as numbered in B. S. Chapman et al., Nuc. Acids Res. 19, 3979 (1991)]. The template used for the PCR reactions was pCMVintA-Lux, made by ligating the Hind III and Nhe I fragment from pCMV6a120 [see B. S. Chapman et al., ibid.,] which includes hCMV-IE1 enhancer/promoter and intron A, into the Hind III and Xba I sites of pBL3 to generate pCMVIntBL. The 1881 base pair luciferase gene fragment (Hind III-Sma I Klenow filled-in) from RSV-Lux [J. R. de Wet et al., Mol. Cell Biol. 7, 725, 1987] was cloned into the Sal I site of pCMVIntBL, which was Klenow filled-in and phosphatase treated.

The primers that spanned intron A are:

5' primer, SEQ. ID:7:
5'-CTATATAAGCAGAG CTCGTTTAG-3'; The 3' primer, SEQ ID:8:
5'-GTAGCAAAGATCTAAGGACGGTGA CTGCAG-3'.

The primers used to remove the Sac I site are:
sense primer, SEQ ID:9:
5-GTATGTGTCTGAAAATGAGC GTGGAGATTGGGCTCGCAC-3' and the antisense primer, SEQ ID:10:,
5'-GTGCGAGCCCAATCTCC ACGCTCATTTTCAGACACA TAC-3'.

The PCR fragment was cut with Sac I and Bgl II and inserted into the vector which had been cut with the same enzymes.

B) V1J Expression Vector, SEQ. ID:12:

Our purpose in creating V 1J was to remove the promoter and transcription termination elements from our vector, V1, in order to place them within a more defined context, create a more compact vector, and to improve plasmid purification yields.

V1J is derived from vectors V1, (see Example 1) and pUC18, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes (SEQ ID:13:), was purified from an agarose electrophoresis gel. The ends of this DNA fragment were then "blunted" using the T4 DNA polymerase enzyme in order to facilitate its ligation to another "blunt-ended" DNA fragment.

pUC18 was chosen to provide the "backbone" of the expression vector. It is known to produce high yields of plasmid, is well-characterized by sequence and function, and is of minimum size. We removed the entire lac operon from this vector, which was unnecessary for our purposes and may be detrimental to plasmid yields and heterologous gene expression, by partial digestion with the HaeII restriction enzyme. The remaining plasmid was purified from an agarose electrophoresis gel, blunt-ended with the T4 DNA polymerase, treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in *E. coli* and was designated V1J (SEQ. ID:12:). This vector's structure was verified by sequence analysis of the junction regions and was subsequently demonstrated to give comparable or higher expression of heterologous genes compared with V1.

C) V1Jneo Expression Vector, SEQ. ID:14:

It was necessary to remove the $amp^r$ gene used for antibiotic selection of bacteria harboring V1J because ampicillin may not be used in large-scale fermenters. The $amp^r$ gene from the pUC backbone of V1J was removed by digestion with SspI and Eam11051 restriction enzymes. The remaining plasmid was purified by agarose gel electrophoresis, blunt-ended with T4 DNA polymerase, and then treated with calf intestinal alkaline phosphatase. The commercially available $kan^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the $kan^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. We arbitrarily selected V1Jneo#3, referred to as V1Jneo hereafter (SEQ. ID:14:), which contains the $kan^r$ gene in the same orientation as the $amp^r$ gene in V1J as the expression construct.

D) V1Jns Expression Vector:

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

E) pGEM-3-IRES: The encephalomyocarditis virus (EMCV) internal ribosomal entry site (IRES) allows efficient expression of two genes within a single mRNA transcript when it is juxtaposed between them. We have utilized this non-coding gene segment to create dicistronic expression vectors for polynucleotide vaccines. The EMCV IRES segment was subcloned as a 0.6 kb EcoRI/BssHII digestion fragment from the pCITE-1 plasmid (Novagen). This fragment was agarose gel-purified, blunt-ended using T4 DNA polymerase and subsequently ligated into pGEM-3 (Promega) which had been XbaI-digested, blunt-ended with T4 DNA polymerase, and phosphatased. Clones were obtained for each of the two possible orientations of this DNA within pGEM-3 and each junction site verified by DNA sequencing. The preferred orientation for subsequent construction of dicistronic vectors positioned the NcoI site within the IRES proximal to BamHI site within pGEM-3. This vector is referred to as pGEM-3-IRES.

F) pGEM-3-IRES*: A second IRES vector was prepared containing mutations in the IRES sequence (IRES*) conferred by a PCR oligomer which may optimize IRES-driven expression compared to wild type IRES. PCR amplification of IRES* was performed using pCITE-1 plasmid (Novagen) with the following sense and antisense oligomers: 5'-GGT ACA AGA TCT ACT ATA GGG AGA CCG GAA TTC CGC-3', SEQ. ID: 11:, and 5'-CCA CAT AGA TCT GTT CCA TGG TTG TGG CAA TAT TAT CAT CG-3', SEQ. ID:15:, respectively. The mutated residue, underlined in the antisense codon, eliminates an upstream ATG from the preferred ATG contained within the NcoI/Kozak sequence at the 3'-terminal end of the IRES G) pGEM-3-IRES/REV: $HIV_{IIIb}$ REV was PCR amplified from pCV-1 (catalogue #303, NIH AIDS Research and Reference Program) using synthetic oligomers. The sense and antisense oligomers were 5'-GGT ACA AGA TCT ACCATGGCA GGA AGA AGC GGA GAC AGC-3', SEQ. ID: 16:, and 5'-CCA CAT AGA TCT GAT ATC GCA CTATTC TTT AGC TCC TGA CTC C-3', SEQ. ID:17:, respectively. These oligomers provide BglII sites at either end of the translation open reading frame as well as an EcoRV site directly upstream from the BglII site at the 3'-terminal end of rev. After PCR, the REV gene was treated with NcoI (located within the Kozak sequence) and BglII restriction enzymes and ligated with pGEM-3-IRES which had been treated with NcoI and BamHI restriction enzymes. Each ligation junction as well as the entire 0.3 kb REV gene was confirmed by DNA sequencing.

H) V1Jns-tPA: In order to provide an heterologous leader peptide sequence to secreted and/or membrane proteins, V1 Jn was modified to include the human tissue-specific plasminogen activator (tPA) leader. Two synthetic complementary oligomers were annealed and then ligated into V1Jn which had been BglII digested. The sense and antisense oligomers were 5'-GATC ACCATGGAT GCA ATG AAG AGA GGG CTC TGC TGT GTG CTG CTG CTG TGT GGA GCA GTC TTC GTT TCG CCC AGC GA-3', SEQ.ID: 18:, and 5'-GAT CTC GCT GGG CGA AAC GAA GAC TGC TCC ACA CAG CAG CAG CAC ACA GCA GAG CCC TCT CTT CAT TGC ATC CAT GGT-3', SEQ. ID:19:. The Kozak sequence is underlined in the sense oligomer. These oligomers have overhanging bases compatible for ligation to BglII-cleaved sequences. After ligation the upstream BglII site is destroyed while the downstream BglII is retained for subsequent ligations. Both the junction sites as well as the entire tPA leader sequence were verified by DNA sequencing. Additionally, in order to conform with our consensus optimized vector V1Jns (=V1Jneo with an SfiI site), an SfiI restriction site was placed at the KpnI site within the BGH terminator region of V1Jn-tPA by blunting the KpnI site with T4 DNA polymerase followed by ligation with an SfiI linker (catalogue #1138, New England Biolabs). This modification was verified by restriction digestion and agarose gel electrophoresis.

I) V1Jns-$HIV_{IIIb}$ REV: REV was amplified by PCR as described above for pGEM-3-IRES/REV, digested with BglII restriction enzyme, and ligated into V1Jns which had been BglII- and calf intestinal alkaline phosphatase-treated. Ligation junctions were confirmed by DNA sequencing and expression of REV was verified by in vitro transfection of RD cells and immunoblot analysis (greater than 1 $\mu$g REV obtained per $10^6$ cells).

J) pGEM-3-RRE/IRES/REV: In order to make a cassette consisting of the REV response element (RRE) which is required to be on an RNA transcript in order for REV-dependent expression to occur, the RRE from HIV strain HXB2 was obtained by PCR using the following synthetic oligomers: sense oligomer, 5'-GGT ACA TGA TCA GAT ATC GCCC GGG C CGA GAT CTT CAG ACT TGG AGG AGG AG-3', SEQ.ID:20:; and antisense oligomer, 5'-CCA CAT TGA TCA G CTT GTG TAA TTG TTA ATT TCT CTG TCC-3', SEQ.ID:21:. These oligomers provide BclI restriction sites at either end of the insert as well as EcoRV and SrfI sites at the 5'-end of the insert. The RRE was blunt-end ligated into pGEM-3-/IRES/REV at the HincII restriction site which precedes IRES. The ligation products were verified by restriction enzyme mapping and by DNA sequencing across the ligation junctions.

EXAMPLE 2 gp120 Vaccines:

Expression of the REV-dependent env gene as gp120 was conducted as follows: gp120 was PCR-cloned from the MN strain of HIV with either the native leader peptide sequence (V1Jns-gp120), or as a fusion with the tissue-plasminogen activator (tPA) leader peptide replacing the native leader peptide (V1Jns-tPA-gp120). tPA-gp120 expression has been shown to be REV-independent [B. S. Chapman et al., Nuc. Acids Res. 19, 3979 (1991); it should be noted that other leader sequences would provide a similar function in rendering the gp120 gene REV independent]. This was accomplished by preparing the following gp120 constructs utilizing the above described vectors:

I. gp120 Vaccine Constructs:

A) V1Jns-tPA-$HIV_{MN}$ gp120: $HIV_{MN}$ gp120 gene (Medimmune) was PCR amplified using oligomers designed to remove the first 30 amino acids of the peptide leader sequence and to facilitate cloning into V1Jns-tPA creating a chimeric protein consisting of the tPA leader peptide followed by the remaining gp120 sequence following amino acid residue 30. This design allows for REV-independent gp120 expression and secretion of soluble gp120 from cells harboring this plasmid. The sense and antisense PCR oligomers used were 5'-CCC CGG ATC CTG ATC ACA GAA AAA TTG TGGGTC ACA GTC-3', SEQ. ID:22:, and 5'-C CCC AGG AATC CAC CTG TTA GCG CTT TTC TCT CTG CAC CAC TCT TCT C-3', SEQ. ID:23:. The translation stop codon is underlined. These oligomers contain BamHI restriction enzyme sites at either end of the translation open reading frame with a BclI site located 3' to the BamHI of the sense oligomer. The PCR product was sequentially digested with BclI followed by BamHI and ligated into V1Jns-tPA which had been BglII digested followed by calf intestinal alkaline phosphatase treatment. The resulting vector was sequenced to confirm inframe fusion between the tPA leader and gp 120 coding sequence, and gp120 expression and secretion was verified by immunoblot analysis of transfected RB cells. Thus, this vector encoding the tPA-$HIV_{MN}$-gp120 is useful for inclusion in a bi- or tri-cistronic construct expressing gag, B7 or other antigens.

B) V1-tPA-HIV 1N gp120: A slightly different version of the chimeric tPA-$HIV_{MN}$ gp120 vector described above was made using an earlier version of our basic vaccine expression vector, V1 (see Nucleic Acid Pharmaceuticals patent), which contained a somewhat different tPA peptide leader sequence from that described for V1Jns-tPA.

In either of the foregoing PNV constructs, provision of an IRES sequence after the translation stop codon, and downstream cloning of immunomodulatory genes such as B7, provides bi- or tri-cistronic polynucleotides useful according to the method of this invention. These PNV's efficiently express both gene products.

C) V1Jns-tPA-$HIV_{IIIB}$ gp120: This vector is analogous to I.A. except that the HIV IIIB strain was used for gp120 sequence. The sense and antisense PCR oligomers used were: 5'-GGT ACA TGA TCA CA GAA AAA TTG TGG GTC ACA GTC-3', SEQ.ID:24:, and 5'-CCA CAT TGA TCA GAT ATC TTA TCT TTT TTC TCT CTG CAC CAC TCT TC-3', SEQ.ID:25:, respectively. These oligomers provide BclI sites at either end of the insert as well as an EcoRV just upstream of the BclI site at the 3'-end. The 5'-terminal BclI site allows ligation into the BglII site of V1Jns-tPA to create a chimeric tPA-gp120 gene encoding the tPA leader sequence and gp120 without its native leader sequence. Ligation products were verified by restriction digestion and DNA sequencing.

II. In Vitro gp120 Vaccine Expression:

In vitro expression was tested in transfected human rhabdomyosarcoma (RD) cells for these constructs. Quantitation of secreted tPA-gp120 from transfected RD cells showed that V1Jns-tPA-gp120 vector produced secreted gp120.

Figure 12:
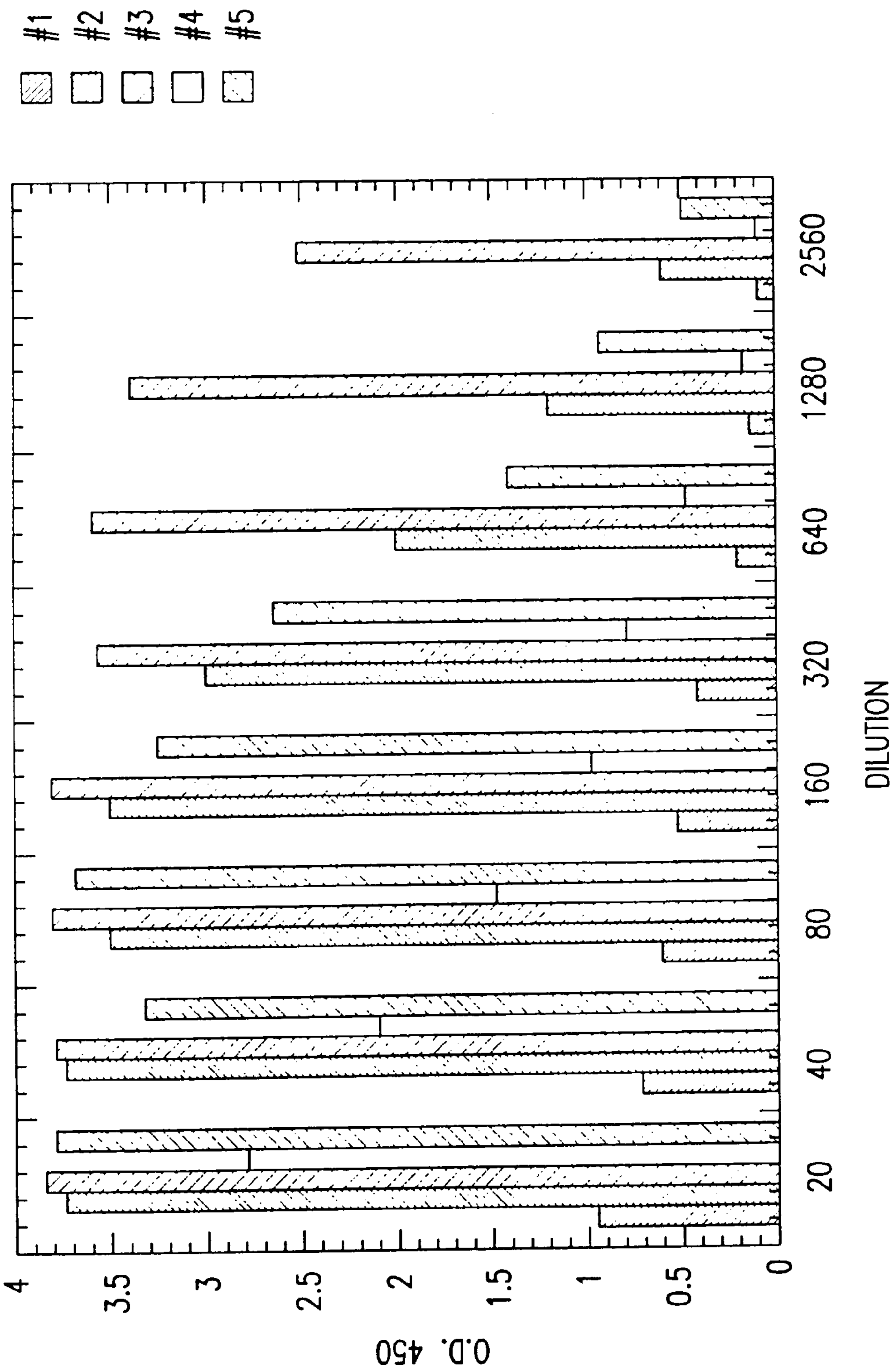
FIG. 12. Antibodies induced by V1Jns-tPA-gp120, 200 μg/mouse per round, 2 rounds.
Figure 13A:
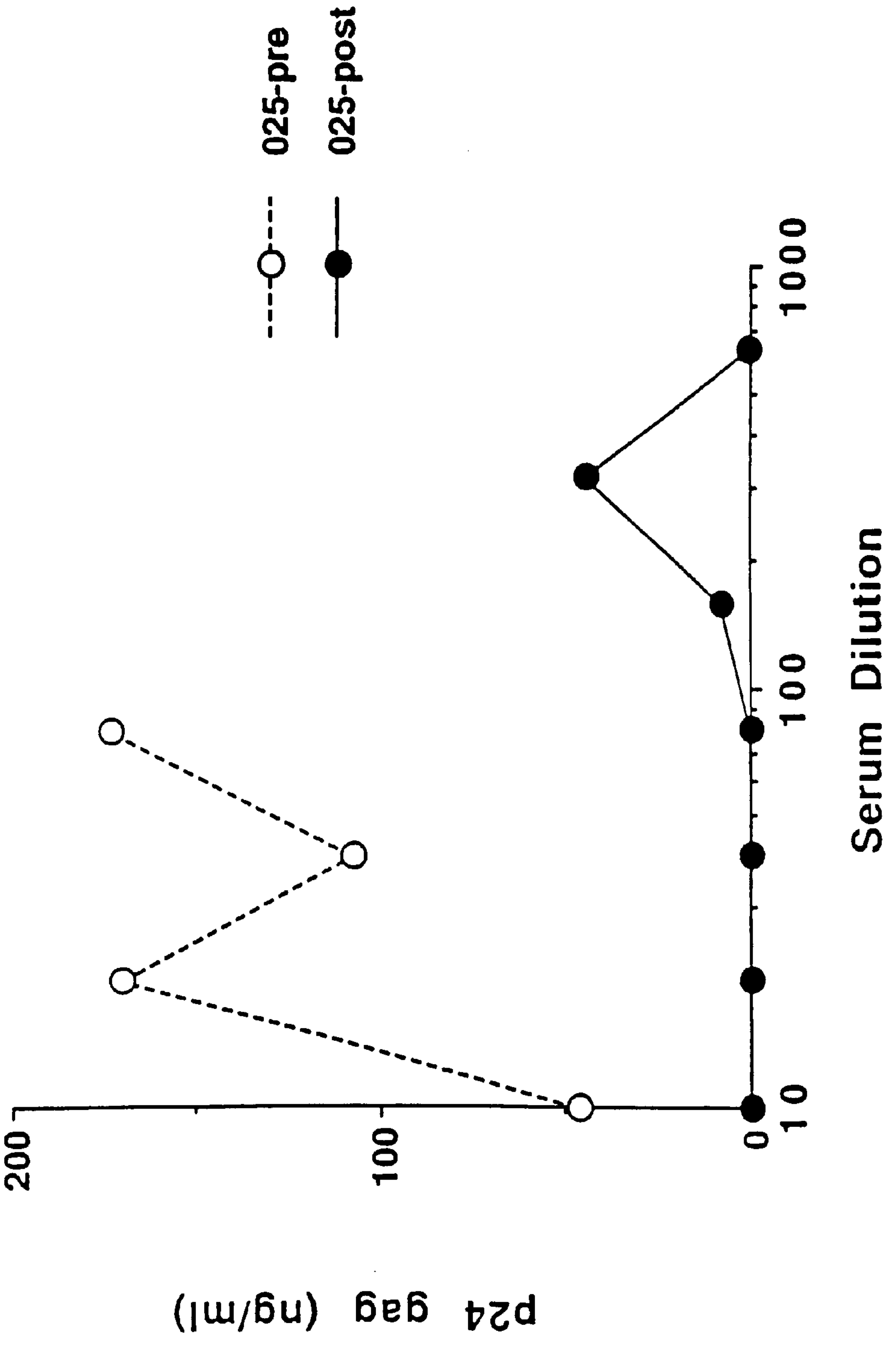
FIG. 13. Neutralization of HIV-1 (MN) virus by sera from V1Jns-tPA-gp120 (MN) DNA vaccinated African Green Monkeys. Panels a and B show the reduction in p24 gag protein production for C8166 cells infected with HIV-1 (MN) following exposure to the indicated dilutions of sera from V1Jns-tPA-gp120 DNA vaccinated monkeys. Data was obtained after 10 days in tissue culture following virus inoculation ($TCID_{50}$ per sample).
Figure 13B:
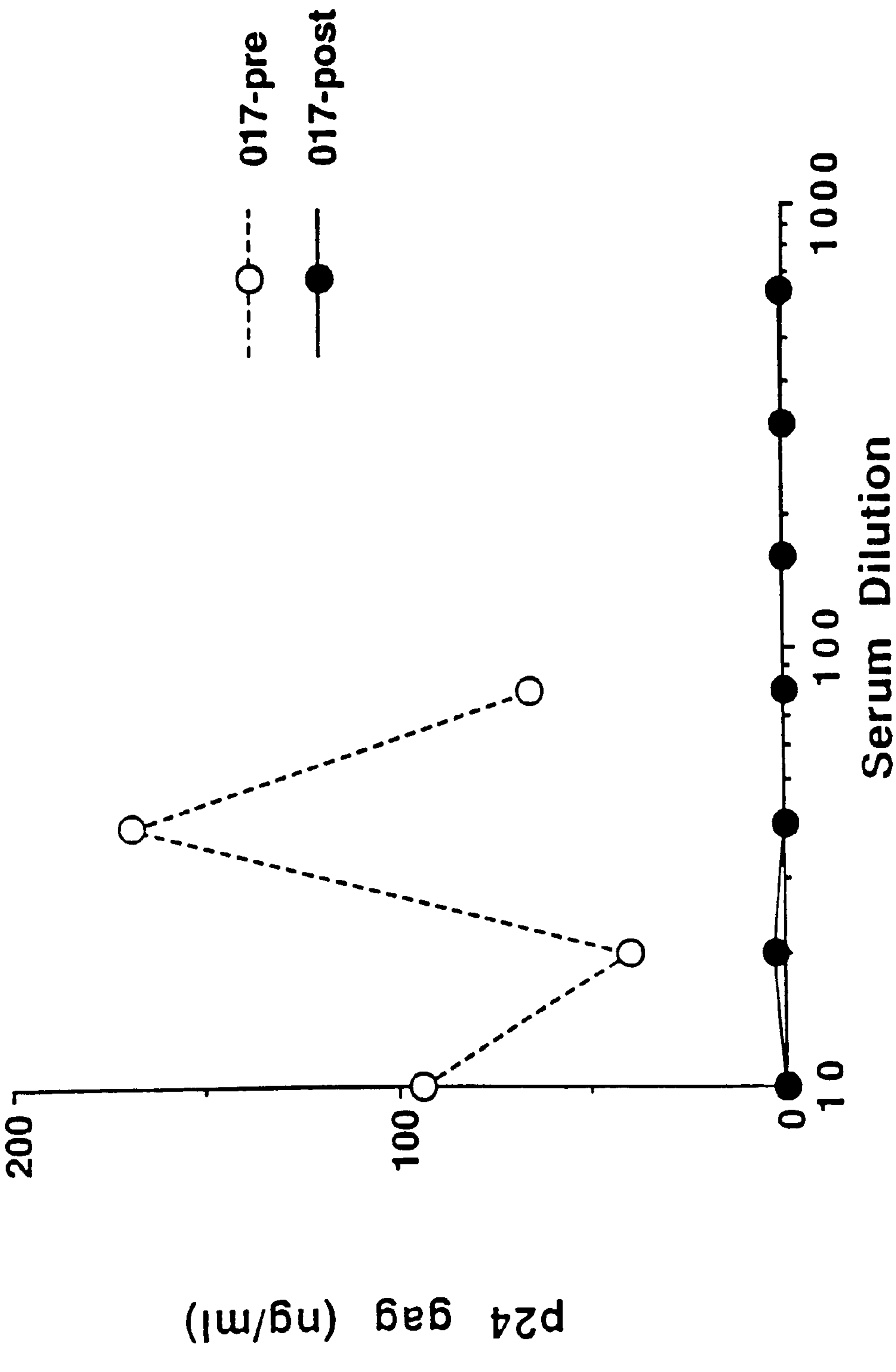
Figure 14:
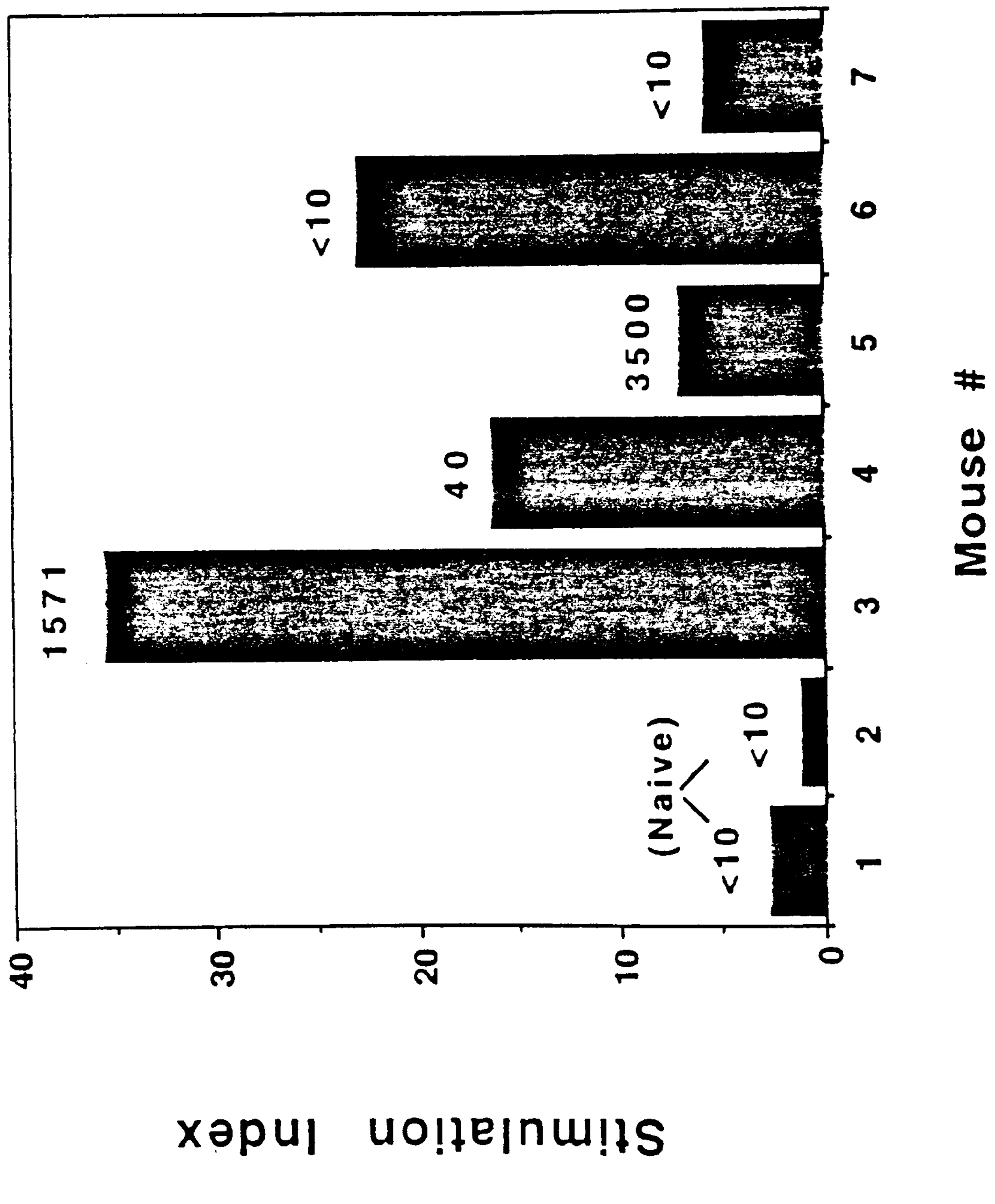
FIG. 14 T cells from V1Jns-tPA-gp120 vaccinated mice exhibiting long-term, antigen-specific T lymphocyte memory responses. Immunized mice received 1.6 mcg of vaccine DNA twice, six months prior to sacrifice. Splenic T cells were cultured in vitro with recombinant gp120 protein at 5 mcg/mL. Proliferation of gp120-specific T cells. A stimulation index (SI; incorporated $^3$H-thymidine for gp120 treated T cells:T cells that did not receive antigen).
Figure 15:
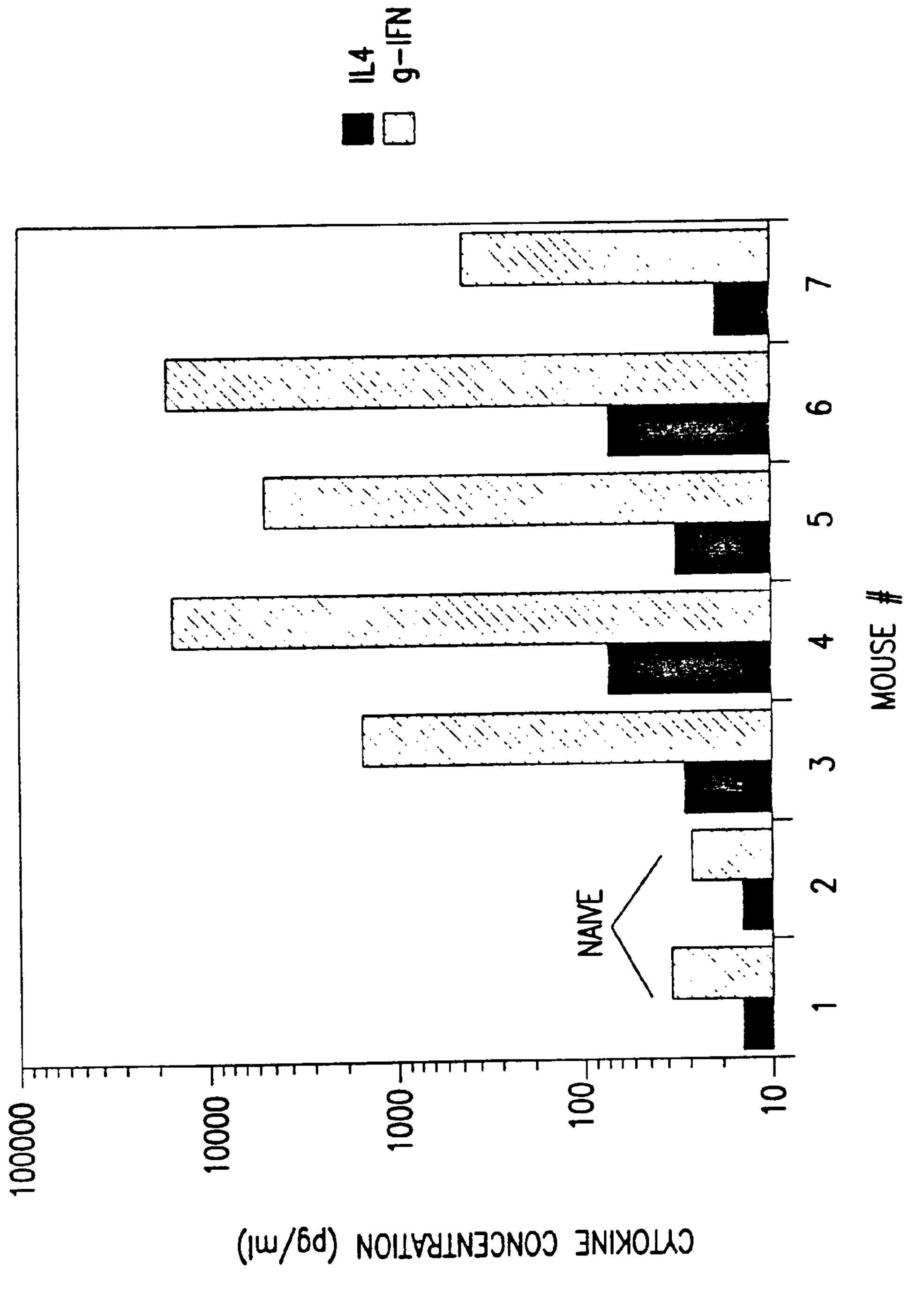
FIG. 15. Type 1 T helper ($T_H1$) lymphocyte cytokine secretion by T cells from V1Jns-tPA-gp120 DNA vaccinated mice. Cell culture supernatants from the samples shown in FIG. 13 were assayed from gamma-interferon and interleukin 4 (IL-4) secretion following treatment with rgp120. Immune mice secreted large amounts of gamma-interferon and very low amounts of IL-4 indicated that $T_H1$-like responses were induced by this vaccine. Control mice showed very low amounts of interferon secretion while the IL-4 levels indicated are background levels.
Figure 16:
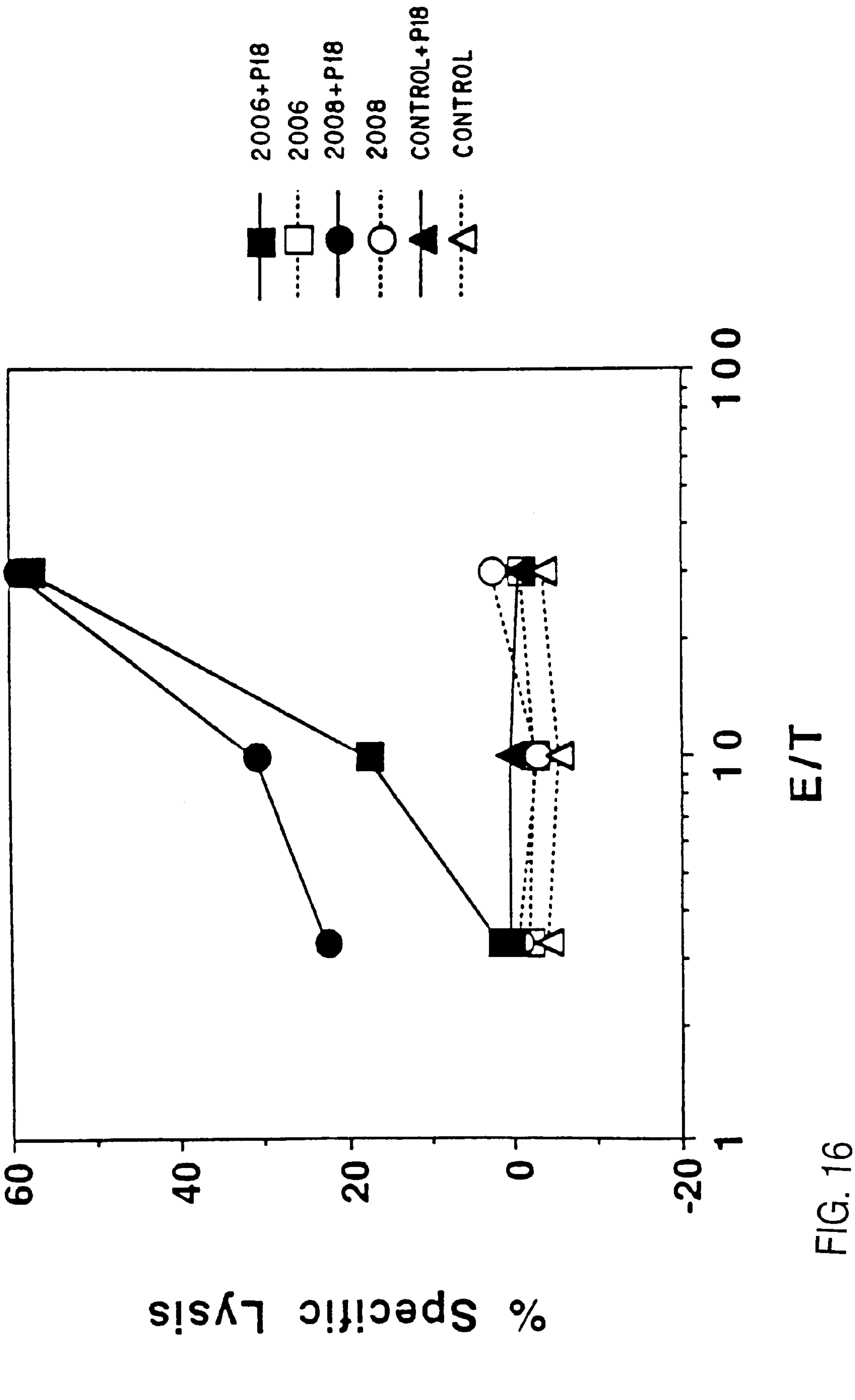
FIG. 16. Anti-gp120 cytotoxic T lymphocyte (CTL) activities in V1Jns-tPA-gp120 DNA vaccinated mice. Two mice (2006 and 2008) showed MHC I restricted CTL activities specific to a gp120 peptide (P18) following gp120 DNA vaccinations. No activities were observed for these mice in the absence of P18 or by a control mouse which had not been previously vaccinated.
Figure 17:
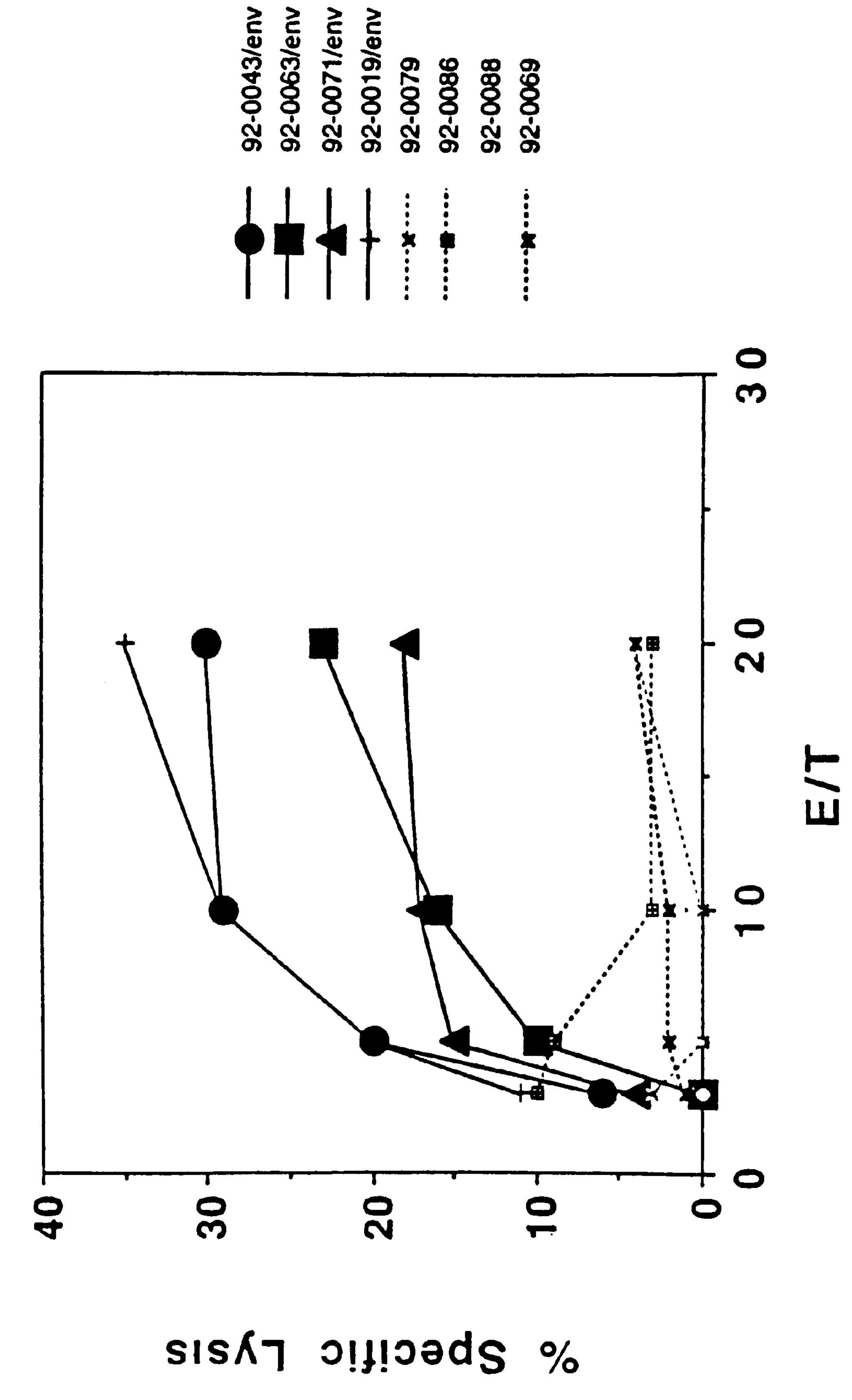
FIG. 17. Anti-gp160 CTL activities by rhesus monkeys vaccinated with V1Jns-gp160/IRES/rev and V1Jns-tPA-gp120 DNA vaccines. T lymphocyte cultures from all four monkeys receiving these vaccines showed MHC I restricted killing of autologous target cells that had been treated with vaccinia-gp160. No CTL activity was observed in four control rhesus that had been immunized with 'blank' DNA vaccine (V1Jns without a gene insert).

III. In vivo gp120 Vaccination:

See FIG. 12 (Mouse Data):

| Anti-gp120 ELISA Titers Elicited by Secreted gp120* | |
|---|---|
| Species | GMT (range) |
| mouse (post 2 rounds, 200 μg per round) | 5,310 ($1.8 \times 10^3$–$1.5 \times 10^4$) |
| rabbit (post 3 rounds, 2 mg per round) | 143 (75–212) |
| A.G. monkey (post 2 rounds, 2 mg per round) | 171 (<10–420) |

*Using V1Jns-tPA-gp120$_{IIIB}$ as the inoculation vector, intramuscularly.

V1Jns-tPA-gp120 PNV-induced Class II MHC-restricted T lymphocyte gp120 specific antigen reactivities. Balb/c mice which had been vaccinated two times with 200 μg V1Jns-tPA-gp120$_{MN}$ were sacrificed and their spleens extracted for in vitro determinations of helper T lymphocyte reactivities to recombinant gp120. T cell proliferation assays were performed with PBMC (peripheral blood mononuclear cells) using recombinant gp120$_{IIIB}$ (Repligen, catalogue #RP1016-20) at 5 μg/ml with $4\times10^5$ cells/ml. Basal levels of $^3$H-thymidine uptake by these cells were obtained by culturing the cells in media alone, while maximum proliferation was induced using ConA stimulation at 2 μg/ml. ConA-induced reactivities peak at ~3 days and were harvested at that time point with media control samples while antigen-treated samples were harvested at 5 days with an additional media control. Vaccinated mice responses were compared with naive, age-matched syngenic mice. ConA positive controls gave very high proliferation for both naive and immunized mice as expected. Very strong helper T cell memory responses were obtained by gp120 treatment in vaccinated mice while the naive mice did not respond (the threshold for specific reactivity is an stimulation index (SI) of >3–4; SI is calculated as the ratio of sample cpm/media cpm). SI's of 65 and 14 were obtained for the vaccinated mice which compares with anti-gp120 ELISA titers of 5643 and 11,900, respectively, for these mice. Interestingly, for these two mice the higher responder for antibody gave significantly lower T cell reactivity than the mouse having the lower antibody titer. This experiment demonstrates that the secreted gp120 vector efficiently activates helper T cells in vivo as well as generates strong antibody responses. In addition, each of these immune responses was determined using antigen which was heterologous compared to that encoded by the inoculation PNV (IIIB vs. MN):

Splenic T Cell Proliferation Responses to rgp120 Following Vaccination with V1Jns-tPA-gp120$_{MN}$

| | Avg. CPM (Stimulation Index) | | | |
|---|---|---|---|---|
| Mouse # (agp120 titer)[3] | Media[1] | ConA[1] | Media[2] | rgp120[2] |
| #1 (naive; <10) | 339 (1) | 185,358 (546) | 187 (1) | 574 (3) |
| #2 (naive; <10) | 237 (1) | 229,775 (969) | 283 (1) | 511 (1.8) |
| #3 (immune; 5643) | 317 (1) | 221,003 (697) | 354 (1) | 23,109 (65) |
| #4 (immune; 11,900) | 229 (1) | 243,427 (1063) | 235 (1) | 3384 (14) |

[1]Cells harvested on day 4 following 24 hr with $^3$H-thymidine. ConA was used at 2 μg/ml concentration.
[2]Cells harvested on day 5 following 24 hr with $^3$H-thymidine. Recombinant gp120$_{IIIB}$ was used at 5 μg/ml concentration.
[3]Anti-gp120$_{IIIB}$ reciprocal endpoint ELISA titers and proliferation assays performed following 2 rounds of 200 μg DNA/mouse (Balb/c).

The foregoing data clearly demonstrates efficient in vivo expression of relevant HIV antigens with a polynucleotide vaccine antigen and elicitation of specific immune responses to the expressed gene product. This construct is easily modified to form a bi-cistronic PNV of this invention by including, downstream from the gp120 translation stop codon, an second or third cistron encoding REV, B7, gag or other antigens unrelated to HIV, such as influenza nucleoprotein or hemagglutinin encoding genes.

EXAMPLE 3 gp 160 VACCINES

In addition to secreted gp120 constructs, we have prepared expression constructs for full-length, membrane-bound gp160. The rationales for a gp160 construct, in addition to gp120, are (1) more epitopes are available both for both CTL stimulation as well as neutralizing antibody production including gp41, against which a potent HIV neutralizing monoclonal antibody (2F5, see above) is directed; (2) a more native protein structure may be obtained relative to virus-produced gp160; and, (3) the success of membrane-bound influenza HA constructs for immunogenicity [Ulmer et al., Science 259:1745–1749, 1993; Montgomery, D., et al., *DNA and Cell Biol.*, 12:777–783, 1993].

gp160 retains substantial REV dependence even with a heterologous leader peptide sequence. Therefore, two strategies independent from that employed for gp120 expression were developed for preparing a gp160 expression vector: (1) subcloning into V1Jns a genomic HIV DNA fragment reported to be effective for heterologous gp160 expression containing tat, REV and gp 160 in entirety (V1Jns-tat/REV/env), [Wang et al., P.N.A.S. USA 90:4156–4160 (May, 1993); all of the data reported in that study were generated using bupivacaine injection about 24 hours prior to nucleic acid injection. As bupivicaine is known to cause muscle damage, this is a regiment that clearly could not be used to immunize humans], and (2) PCR-cloning a minimal gp160 ORF into a dicistronic vector before the EMCV internal ribosomal entry site (IRES) to efficiently reinitiate translation following gp160 translation for a second cistron encoding REV. This construct ensures effective simultaneous production of both gp160 and REV proteins (V1Jns-gp160/IRES/rev). Each of these vectors has been prepared in addition to the monocistronic vectors V1Jns-gp160 and V1Jns-REV. Because there is evidence, in the literature and from our own experiments (see below), that the env mRNA requires the tat/REV splice donor (SD) site for stability in heterologous expression systems, V1Jns-gp160 and V1Jns-gp160/IRES/REV were also prepared with this SD inserted upstream of the env ORF. These vaccine constructs were prepared as follows.

I. gp160 Vaccine Constructs:

Both gp160 expression vectors, V1Jns-gp160 and V1Jns-gp160/IRES/rev (see A and B below) were prepared with the tat/rev splice donor (SD) inserted immediately upstream of gp160 sequences at the PstI site within V1Jns (this is the solitary PstI site within both of these vectors). Synthetic complementary oligomers encoding the SD were designed to ligate into the PstI site retaining the original site at the 5'-end but destroying the PstI site at the 3'-end of the insert after ligation. The oligomer sequences used were: 5'-GTC ACC GTC CTC TAT CAA AGC AGT AAG TAG TAC ATG CA-3', SEQ.ID:26: and 5'-TGT ACT ACT TAC TGC TTT GAT AGA GGA CGG TGA CTG CA-3', SEQ.ID:27:. The resulting plasmids were verified by restriction digestion mapping and by DNA sequencing across the entire SD/PstI region.

A). V1Jns-$HIV_{IIIb}$gp160: $HIV_{IIIb}$ gp160 was cloned by PCR amplification from plasmid pF412 which contains the 3'-terminal half of the $HIV_{IIIb}$ genome derived from $HIV_{IIIb}$ clone HXB2. The PCR sense and antisense oligomers were 5'-GGT ACA TGA TCA ACCATGAGA GTG AAG GAG AAA TAT CAG C-3', SEQ. ID:28:, and 5'-CCA CAT TGA TCA GAT ATC CCC ATC TTA TAG CAA AAT CCT TTC C-3', SEQ. ID:29:, respectively. The Kozak sequence and translation stop codon are underlined. These oligomers provide BclI restriction enzyme sites outside of the translation open reading frame at both ends of the env gene. (BclI-digested sites are compatible for ligation with BglII-digested sites with subsequent loss of sensitivity to both restriction enzymes. BclI was chosen for PCR-cloning gp160 because this gene contains internal BglII and as well as BamHI sites). The antisense oligomer also inserts an EcoRV site just prior to the BclI site as described above for other PCR-derived genes. The amplified gp160 gene was agarose gel-purified, digested with BclI, and ligated to V1Jns which had been digested with BglII and treated with calf intestinal alkaline phosphatase. The cloned gene was about 2.6 kb in size and each junction of gp160 with V1Jns was confirmed by DNA sequencing.

B). V1Jns-$HIV_{IIIb}$ gp160/IRES/REV: pGEM-3-IRES/REV was digested with HinDII and SmaI restriction enzymes (contained within the pGEM-3 multi-linker region) to remove the entire IRES/REV sequence (–0.9 kb) and then ligated with V1Jns-$HIV_{IIIb}$gp160 which had been digested with EcoRV and phosphatased. This procedure yielded an 8.3 kb dicistronic V1Jns containing gp160 followed by IRES and REV which directs expression of both of these HIV gene products. All of the junction regions were verified by DNA sequencing.

C) V1Jns-tPA-$HIV_{IIIB}$ gp160: This vector is similar to Example 2(C) above, except that the full-length gp160, without the native leader sequence, was obtained by PCR. The sense oligomer was the same as used in I.C. and the antisense oligomer was 5'-CCA CAT TGA TCA GAT ATC CCC ATC TTA TAG CAA AAT CCT TTC C-3', SEQ.ID: 30:. These oligomers provide BclI sites at either end of the insert as well as an EcoRV just upstream of the BclI site at the 3'-end. The 5'-terminal BclI site allows ligation into the BglII site of V1Jns-tPA to create a chimeric tPA-gp160 gene encoding the tPA leader sequence and gp160 without its native leader sequence. Ligation products were verified by restriction digestion and DNA sequencing.

D) V1Jns-tat/rev/$env_{IIIB}$: This expression vector is patterned after one described by D. Rekosh et al. [Proc. Natl. Acad. Sci. USA, 85, 334 (1988)] employing a "genomic" segment of an HIV-1 IIIB clone (HXB2) encompassing unspliced tat, rev, and env in their entirety. V1Jns was digested with BglII followed by T4 DNA polymerase blunting and calf intestinal alkaline phosphatase treatment. A SalI/XhoI fragment of the IIIB genome contained within pF412 was obtained by restriction digestion and blunted with T4 DNA polymerase. Ligation products were verified by restriction digestion mapping and DNA sequencing.

E) V1Jns-rev/envIIIB: This vector is a variation of the one described in section D above except that the entire tat coding region in exon 1 is deleted up to the beginning of the REV open reading frame. V1Jns-$gp160_{IIIB}$ (see section A. above) was digested with PstI and KpnI restriction enzymes to remove the 5'-region of the gp160 gene. PCR amplification was used to obtain a DNA segment encoding the first REV exon up to the KpnI site in gp160 from the HXB2 genomic clone. The sense and antisense PCR oligomers were 5'-GGT ACA CTG CAG TCA CCG TCC T ATG GCA GGA AGA AGC GGA GAC-3', SEQ.ID:31: and 5'-CCA CAT CA GGT ACC CCA TAA TAG ACT GTG ACC-3', SEQ.ID:32: respectively. These oligomers provide PstI and KpnI restriction enzyme sites at the 5'- and 3'-termini of the DNA fragment, respectively. The resulting DNA was digested with PstI and KpnI, purified from an agarose electrophoretic gel, and ligated with V1Jns-gp160(PstI/KpnI). The resulting plasmid was verified by restriction enzyme digestion.

Figure 5A:
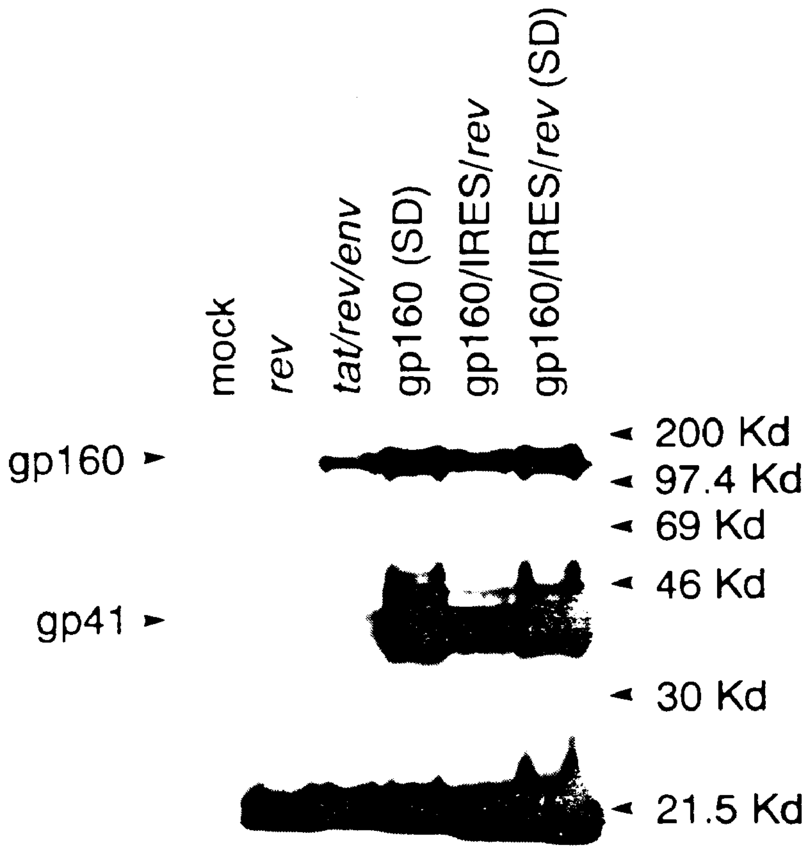
FIG. 5. Western blot analysis of gp160 expression induced by HIV polynucleotide immunogens. This result rigorously shows the coexpression in a single cell of more than one gene product from a single polynucleotide construct: A polynucleotide encoding gp160 alone (see panel B, fourth lane from the left) expresses no detectable gp160, but with REV added in trans (by cotransfection of a construct encoding only REV), there is good gp 160 expression (panel A, fourth lane from the left). A genomic tat/REV/env construct expresses only low levels of gp160, whether or not REV is provided in trans (panels A and B, third lane). However, a dicistronic gp160/IRES/REV construct heavily expresses gp160 (panels A and B, fifth lane from the left). The best expression, is obtained in a dicistronic construct encoding gp160/IRES/REV, with a splice donor (SD) provided 5' to the gp160 coding sequence (panels A and B, right hand lane). Because no additional expression is achieved when additional REV is provided in trans (panel A right hand lane), the system is not limited by the level of REV being expressed.
Figure 5B:
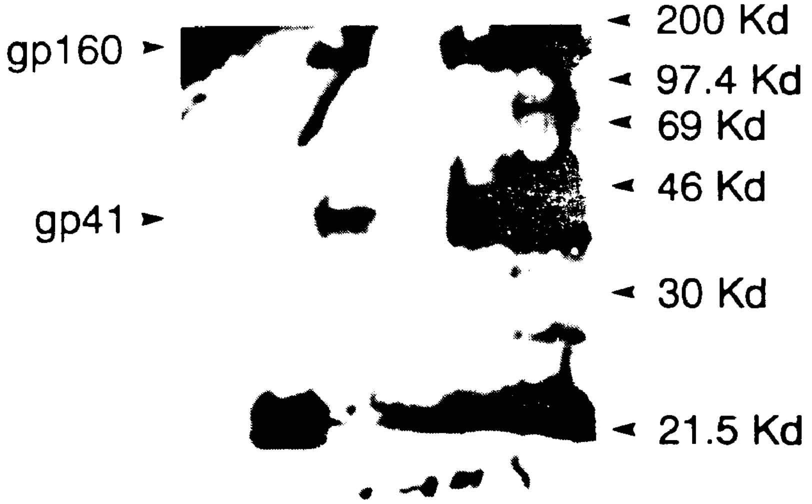

II. In Vitro Expression OF gp160 Vaccine:

RD and 293 cells were transiently transfected with gp160 and REV expression constructs. A Western blot analysis shown in FIG. 5 using an anti-gp41 monoclonal antibody (Chessie 8, NIH AIDS Research and Reference Program #526) showed that gp160 expression by V1Jns-gp160 (SD) required the addition of V1Jns-REV (this vector produces >1 $\mu$g REV/$10^6$ cells in transient transfections). V1Jns-gp160/IRES/REV efficiently expressed gp160 without additional REV added in trans, confirming function of the dicistron. Similar results were found with an anti-gp120 monoclonal antibody (1C1, Repligen, #RP1010-10) for immunoblot visualization. Proteolytic processing of gp160 to the mature gp120 and gp41 forms was observed for each vector. Addition of REV in trans to the dicistronic gp160/REV vector did not result in more gp160 expression indicating that REV expression is not limiting for gp 160 expression in this vector. Expression of gp 160 improved if the tat/REV SD was included within dicistronic gp160/REV construct indicating the importance of this site for optimal REV-dependent gp160 expression. We were also surprised to discover that dicistronic gp160/REV expressed more than ten-fold more gp 160 than the genomic tat/REV/env construct for transient transfections, again demonstrating the high efficiency of this vector for gp160 expression.

These vectors provide nucleic acid constructs for gp160 plasmid vaccinations with gp160 and REV genes either on separate plasmids or on the same plasmid. In the case of the tpa-gp160 construct, REV need not be provided in cis or in trans to achieve efficient gp160 expression, therefore allowing other genes to be incorporated in a dicistronic construct.

For the REV-dependent constructs, it is important to test whether effective gp160 expression following vaccination requires REV to be present on the same plasmid because very small quantities of DNA are taken up by muscle cells following intramuscular injection, and individual muscle cells (each having hundreds of nuclei) may not receive copies of different plasmids in proximal locations within the cell.

Figure 9:
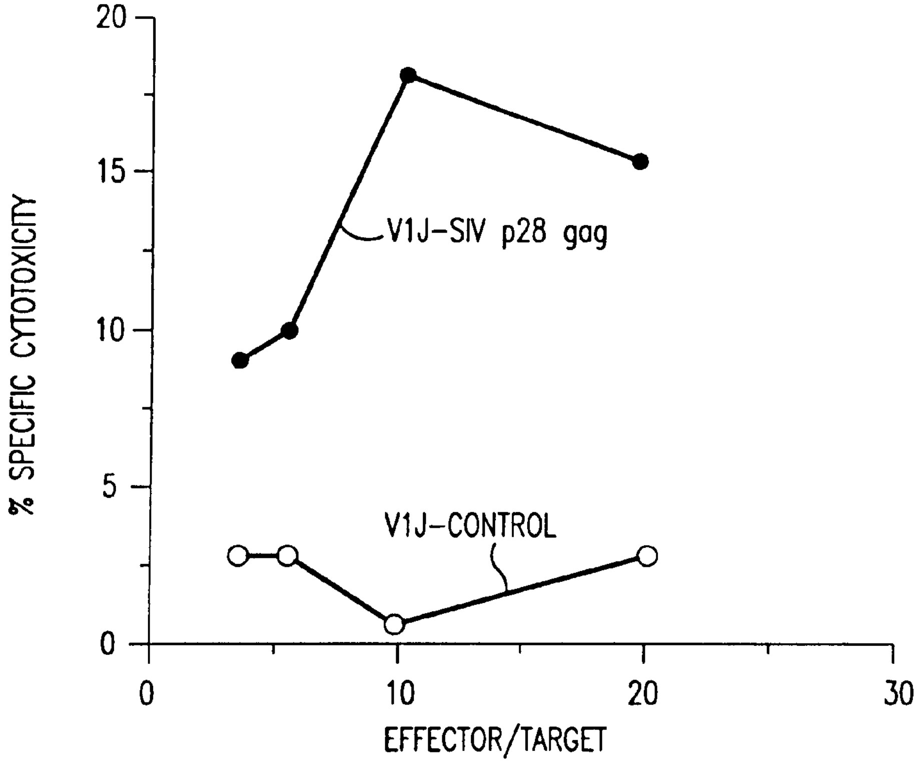
FIG. 9. Cytotoxic T lymphocytes generated in rhesus monkeys in response to V1J-SIV-p28 polynucleotide construct vaccination (REV independent). This SIV p28 is equivalent to p24 gag of HIV. Thus, CTLs specific to a group specific antigen are inducible using a gag encoding polynucleotide construct.
Figure 10:
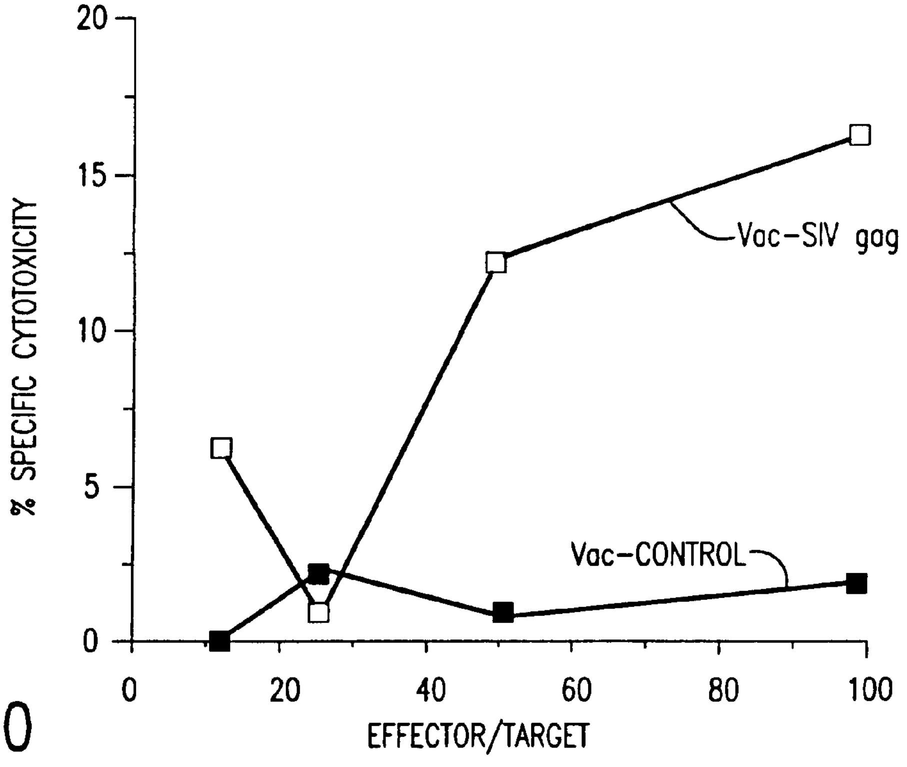
FIG. 10. Cytotoxic T lymphocytes generated in response to Vaccinia-SIVp28 nucleic acid vaccination. This demonstrates that similar CTLs are induced by a gag encoding polynucleotide (FIG. 9) as compared with a replicating antigen (vaccinia) expressing the same antigen [see Shen, L., et al., *Science* 252:440–443, 1991].

III. In vivo Vaccination with gp160 Vaccines:

Three different vector strategies were compared for their abilities to induce anti-gp120 antibody responses in nonhuman primates using PNVs encoding gp160: vaccination with (1) dicistronic gp160/REV using V1Jns-gp160$_{IIIB}$/IRES/REV (SD); (2) the genomic gp160 construct V1Jns/tat/rev/env$_{IIIB}$; and (3) a mixture of monocistronic vectors, V1Jns-gp160$_{IIIB}$ (SD) and V1Jns-REV. Vaccination doses of 2 mg/animal were used for up to three vaccination rounds which were delivered at one month intervals while simultaneously obtaining bleeds. Anti-gp120 ELISA titers using recombinant gp120 MB are shown for monkeys vaccinated with each of these vectors. Dicistronic gp160/REV elicited antibody responses in both rhesus and African Green monkeys while the genomic gp160 and mixed monocistronic vectors did not elicit detectable antibodies after two rounds of vaccination (i.e., one month following the second vaccination). All four monkeys which received dicistronic gp160/REV also showed specific anti-gp41 reactivities as measured by the BIAcore assay using recombinant gp41 (ABT) as the immobilized substrate (data not shown). The sera obtained from these monkeys also showed anti-V3$_{IIIB}$ ELISA reactivities with titers ranging from ~50–100. These results prove that in vivo expression induced by PNV for multiple cistrons is not analogous to results obtained by in vitro transfection methods in which gp160 expression was shown for all three vector strategies. Note especially that in vitro transfection resulted in equivalent expression by the mixed monocistronic gp160 and REV vectors as compared to dicistronic gp160/REV (see FIG. 5). These experiments prove that our dicistronic PNVs do deliver effective coordinate expression following in vivo vaccination while other methods of vaccination with multiple cistrons were unable to do so. See FIG. 9, showing two African Green Monkeys and two rhesus monkeys and one rabbit's immune responses.

Anti-gp120 ELISA Titers Elicited by gp160 PNVs in Non-Human Primates 2 mg DNA per round

| Vector/Species | | Titer post 2nd | Titer post 3rd |
|---|---|---|---|
| V1Jns-tat/rev/env$_{IIIB}$: | | | |
| African Green | (#1) | <20 | ND[1] |
| | (#2) | <20 | ND |
| | (#3) | <20 | ND |
| V1Jns-gp160$_{IIIB}$ + V1Jns-rev[2]: | | | |
| African Green | (#1) | <20 | ND |
| | (#2) | <20 | ND |
| | (#3) | <20 | ND |
| V1Jns-gp160$_{IIIB}$/IRES/rev: | | | |
| African Green | (#1) | 85 | 90 |
| | (#2) | 75 | 60 |
| Rhesus | (#1) | 165 | 175 |
| | (#2) | 290 | 260 |

[1]ND = not determined.

[2]This PNV represents an equimolar mixture of the two monocistronic vectors.

Anti-V3$_{IIIB}$ ELISA Titers Elicited by gp160/rev Dicistron* in Non-Human Primates. 2 mg DNA per round

| Species (animal #) | | Titer (post 3rd vaccination) |
|---|---|---|
| African Green | (#1) | 70 |
| | (#2) | 45 |
| Rhesus | (#1) | 55 |
| | (#2) | 100 |

*Using V1Jns-gp160$_{IIIB}$/IRES/rev as the inoculation vector.

EXAMPLE 4

SIV Vaccines

An SIV env construct, V1Jn-SIV gp152, was made by PCR-cloning from a genomic clone of the SIV$_{MAC251}$ virus isolate and confirmed by DNA sequencing of both junctions with the vector. This strain is homologous to the virus which is used at the New England Regional Primate Center (NRPC) for infectious SIV challenges to rhesus monkeys. A similar SIV gp152 construct is prepared in which the DNA encoding the leader peptide region uses alternative codons but which retains the native amino acid sequence. This reduces the REV-dependence of this construct and makes a more stable mRNA transcript. These vaccine constructs were prepared as follows.

I. SIV Vaccine Constructs:

A). V1J-SIV$_{MAC251}$ p28 gag: The central peptide of SIV gag, referred to as p28 gag, was chosen for a polynucleotide vaccine to test for CTL generation in nonhuman primates. This region of gag encodes a known CTL epitope for macaque monkeys which have the MHC Class I haplotype known as Mamu-A01. Thus, monkeys bearing this haplotype should demonstrate CTL reactivity this gag epitope after vaccination with the appropriate gag plasmid. While both SIV and HIV gag genes contain regulatory sequences which are REV dependent, p28 gag expression appears to be less REV-dependent so that at least some expression may be achieved in the absence of REV.

SIV p28 gag was cloned into expression vectors V1 using BglII restriction enzyme sites after PCR amplification from the plasmid p239SpSp5' (obtained from the NIH AIDS Research and Reference Program, catalogue #829) using custom synthetic oligodeoxyribonucleotides. This plasmid encodes the 5'-half of the SIV$_{MAC239}$ genome. SIV$_{MAC239}$ is a subsequent in vitro passage line of SIV$_{MAC251}$ which has undergone some mutations compared to the parental virus. However, the amino acid sequences between these viruses are identical for p28 gag. The PCR sense and antisense oligomers were 5'-GGT ACA AGA TCT ACC ATG GGA CCA GTA CAA CAA ATA GGT GGT AAC-3', SEQ. ID:33:, and 5'-CCA CAT AGA TCT TTA CAT TAA TCT AGC CTT CTG TCC C-3', SEQ. ID:34:. These oligos provide BglII restriction enzyme sites outside the translational open frames, a consensus Kozak translation initiation codon context (underlined) and translation stop codon (underlined). PCR-generated p28 gag was agarose gel-purified, digested with BglII and ligated into BglII-treated, phosphatased V1. This gene was subsequently subcloned into our optimized expression vector, V1J, using BglII restriction enzyme sites and designated as V1J-SIV p28 gag. The cloned gene was about 0.7 kb long. The junction sites of the V1J CMV promoter and 5'terminus of p28 gag were verified by DNA sequence analysis for each construct. In vitro expression of SIV p28 protein was compared for V1J and V1 constructs by Western blotting using plasma from an SIV-infected macaque monkey to detect gag protein. The V1J-SIV p28 gag construct consistently gave the most product at the appropriate molecular weight position. Similar and even improved results are obtained with the more optimized V1jneo, V1Jns and V1R vectors.

B). V1J-$SIV_{MAC251}$ nef: SIV nef was cloned after PCR amplification from the plasmid pBK28 which encodes the entire $SIV_{MAC251}$ genome (a gift from Dr. Vanessa Hirsch, NIAID, NIH, Rockville, Md.; now listed as catalogue #133, NIH AIDS Research and Reference Program). The PCR sense and antisense oligomers were 5'-GGT ACA ACC ATG GGT GGA GCT ATT TCC ATG AGG-3', SEQ. ID:35: and 5'-CCT AGG TTA GCC TTC TTC TAA CCT CTT CC-3', SEQ. ID:36:. The Kozak site and translation stop codon are underlined. The amplified nef gene was agarose gel-purified, blunt-ended using T4 DNA polymerase, phosphorylated at the 5'-terminus using T4 DNA kinase, and cloned into a blunted BglII restriction enzyme site of V1J which had been phosphatased using calf intestinal alkaline phosphatase. The cloned gene was about 0.76 kb long. The junction site of the V1J CMV promoter and 5'-terminus of nef was confirmed by DNA sequencing. In vitro expression was shown using Western blot analysis and an HIV nef antiserum (catalogue #331, NIH AIDS Research and Reference Program).

C). V1Jn-$SIV_{MAC251}$ gp152: SIV env, referred to as gp152, was cloned after PCR amplification from the plasmid pBK28 into V1Jneo (see Nucleic Acid Pharmaceuticals patent). The PCR sense and antisense oligomers were 5'-GGT ACA AGA TCT ACC ATG GGA TGT CTT GGG AAT CAG C-3', SEQ. ID:37: and 5'-CCA CAT AGA TCT GAT ATC GTA TGA GTC TAC TGG AAA TAA GAG G-3', SEQ.ID:38. The Kozak site and amber translation stop codon are underlined. The PCR product has BglII restriction enzyme sites outside the translation open reading frame at both ends with an additional EcoRV site immediately preceding the 3'-terminal BglII site but after the amber stop codon. This provides a convenient restriction enzyme site for subsequent cloning steps. The amplified gp152 gene was agarose gel-purified, BglII-digested and ligated with V1Jn which had been BglII-digested and phosphatased. The cloned gene was about 2.2 kb long. The junctions at each end of gp152 with V1Jn CMV promoter and BGH terminator regions were verified by DNA sequencing.

Figure 4:
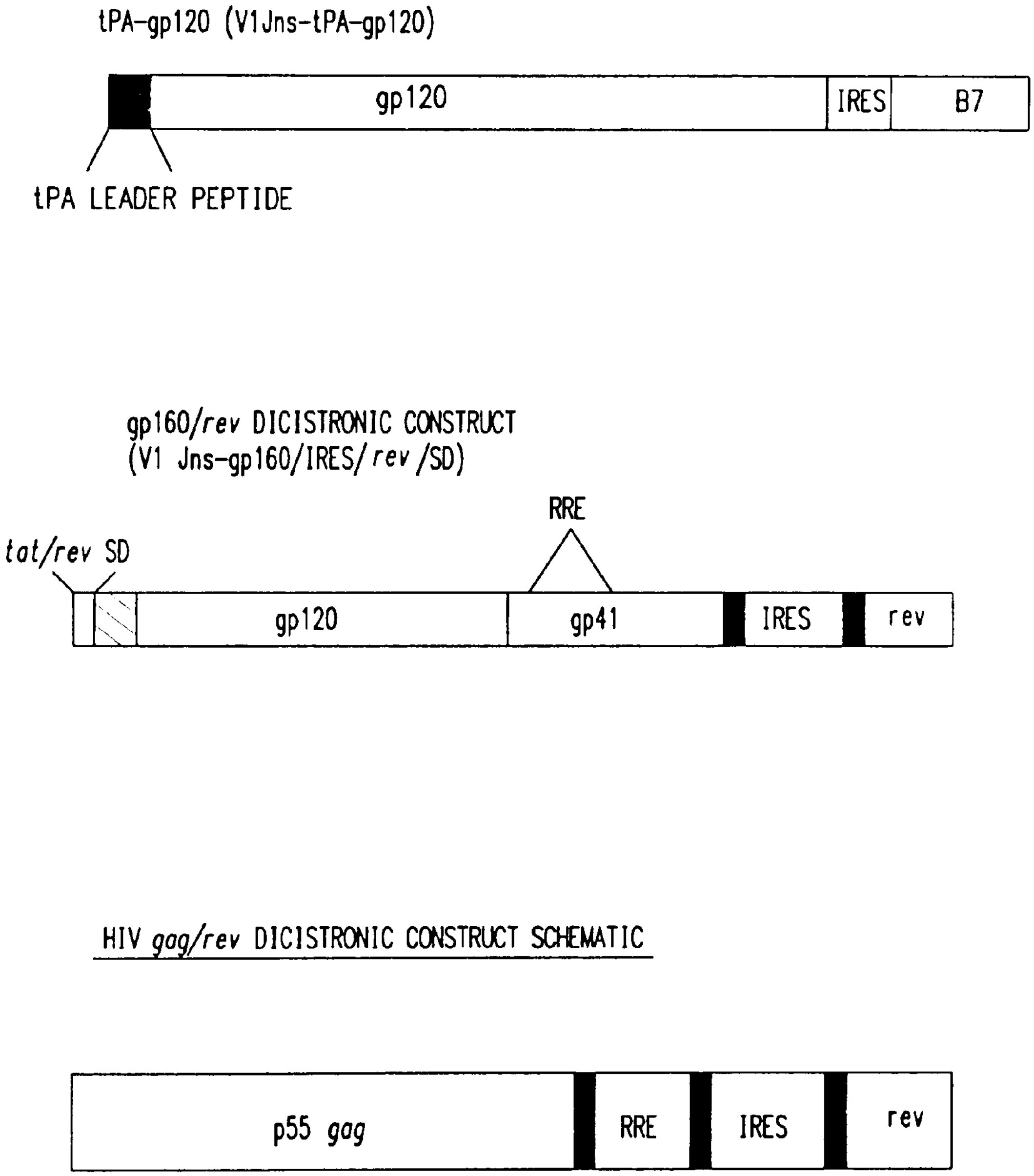
FIG. 4. Detailed schematic of dicistronic HIV env and gag polynucleotide immunogen constructs showing specific regulatory elements.

II. In Vivo Vaccination with SIV Vaccines:

Two SIV gene constructs have been used for vaccination of rhesus monkeys and have been shown to generate specific CTL responses in non-human primates (see. FIG. 4).

V1J-SIV p28 gag, which expresses the relatively REV-independent central peptide of gag, and V1J-SIV nef were i.m.-injected into Macaca mulatta monkeys at 3 mg/vaccination for three injection rounds spaced one month apart. The gag-specific CTL response of rhesus monkeys with the Mamu-A01 MHC I haplotype is restricted primarily to a single peptide epitope within p28 gag. Mamu-$A01^+$ monkeys receiving V1J-SIV p28 gag had gag-specific CTL activity beginning at one month after the second injection while Mamu-$A01^-$ monkeys receiving this DNA as well as monkeys receiving V1J control DNA did not show a CTL response. Both in vitro, gag peptide-restimulated CTL as well as primary CTL were detected after the second and third vaccination rounds, respectively. These CTL activity levels were comparable to those generated by vaccinia-gag inoculation. Subsequently, the CTL levels declined in responding animals. These animals are re-vaccinated to boost the initial CTL response. V1J-SIV nef-vaccinated animals have not shown a specific CTL response, although a more refined assay, such as the one used for gag CTL detection, (i.e., no dominant MHC I haplotype/nef peptide relationship has been defined for rhesus monkeys so that peptides of unknown effectiveness are used for stimulation, and there is no positive control), may provide a different result.

EXAMPLE 5

Other Vaccine Constructs

A. V1Jns-$HIV_{IIIB}$ gag/pol-RRE/IRES/REV: Dicistronic expression vectors encoding gag with or without the protease region of pol were made by PCR amplification of $HIV_{IIIB}$ gag-pol sequences with several variations. Inclusion of the protease (prt) segment of pol allows proteolytic processing of gag into various peptides (e.g., p17, p24, p15, etc.) which comprise the mature capsid particles while omission of this enzyme results in p55 synthesis in the form of immature capsid particles. More extensive sequences of pol were not included to avoid potential safety hazards that may be associated with the reverse transcriptase and integrase enzymatic activities of pol. For gag capsid particles, whether processed into the mature forms or not, to be extruded from cells myristoylation of the glycine amino acid at position two following the initial Met must occur. Mutagenesis of this glycine residue abrogates myristoylation and no gag particles are extruded from the cell. These modifications of gag allow us to determine whether either generation of anti-gag CTLs following vaccination with such gag vectors is affected by proteolytic processing and/or extrusion of capsid from cells. Some of the vectors listed below contain a splice donor (SD) site that is found upstream of the gag open reading frame. These vectors allow us to determine whether this SD is necessary for optimum rev-dependent expression of gag as was inclusion of the tat/rev SD for optimum gp160 expression.

1) V1Jns-$HIV_{IIIB}$ gag-prt/RRE/IRES/REV: A gag-prt encoding DNA segment was obtained by PCR amplification using the following sense and antisense oligomers: 5'-GGT ACA GGA TCC ACC ATG GGT GCG AGA GCG TCA GTA TTA AGC-3', SEQ.ID:39: and 5'-CCA CAT GGA TCC GC CCG GGC TTA CAT CTC TGT ACA AAT TTC TAC TAA TGC-3', SEQ.ID:40:, respectively. These oligomers provide BamHI restriction enzyme sites at either end of the segment, a Kozak initiation of translation sequence including an NcoI site, and an SrfI site immediately upstream of the BamHI site at the 3'-terminus. The SrfI site was used to clone the RRE/IRES/REV cassette from pGEM-3-RRE/IRES/REV, which was excised using the EcoRV restriction enzyme, immediately downstream of gag-prt. All ligation junctions were DNA sequence verified and the construct was further verified by restriction enzyme mapping.

2) V1 Jns-$HIV_{IIIB}$ gag-prt/RRE/IRES/REV(SD): This vector was prepared exactly as vector 1 above except that the PCR sense oligomer used was 5'-GGT ACA GGA TCC CCG CAC GGC AAG AGG CGA GGG-3', SEQ.ID:41:. This allows inclusion of the upstream SD site at the beginning of the gag sequence. This construct was verified by restriction enzyme mapping and DNA sequencing of the ligation junctions.

3) V1Jns-$HIV_{IIIB}$ gag-prt/RRE/IRES/REV(w/o myristoylation): This vector is prepared exactly as vector 1 above except that the PCR sense oligomer used was 5'-GGT ACA GGA TCC ACC ATG GCT GCG AGA GCG TCA GTA TCA AGC-3', SEQ.ID:42.

4) V1Jns-HIV$_{IIIB}$ gag/RRE/IRES/REV: This vector is prepared exactly as vector 1 above except that the PCR antisense oligomer used was 5'-CCA CAT GGA TCC GCC CGG GCC TTT ATT GTG ACG AGG GGT CGT TGC-3', SEQ.ID:43.

5) V1Jns-HIV$_{IIIB}$ gag/RRE/IRES/REV (SD): This vector is prepared exactly as vector 4 above except that the PCR sense oligomer used was 5'-GGT ACA GGA TCC CCG CAC GGC AAG AGG CGA GGG-3', SEQ.ID:44.

6) V1Jns-HIV$_{IIIB}$ gag/RRE/IRES/REV (w/o myristoylation): This vector is prepared exactly like vector 5 except that the PCR sense oligomer used was 5'-GGT ACA GGA TCC ACC ATG GCT GCG AGA GCG TCA GTA TTA AGC-3', SEQ.ID:45.

B. V1Jns-HIV nef: This vector uses a nef gene from a viral strain representative of those in the infected population using sense and antisense PCR oligomers analogous to those used for SIV nef.

C. pGEM-3-X-IRES-B7: (where X=any antigenic gene) As an example of a dicistronic vaccine construct which provides coordinate expression of a gene encoding an immunogen and a gene encoding an immunostimulatory protein, the murine B7 gene was PCR amplified from the B lymphoma cell line CH1 (obtained from the ATCC). B7 is a member of a family of proteins which provide essential costimulation T cell activation by antigen in the context of major histocompatibility complexes I and II. CH1 cells provide a good source of B7 mRNA because they have the phenotype of being constitutively activated and B7 is expressed primarily by activated antigen presenting cells such as B cells and macrophages. These cells were further stimulated in vitro using cAMP or IL-4 and mRNA prepared using standard guanidinium thiocyanate procedures. cDNA synthesis was performed using this mRNA using the GeneAmp RNA PCR kit (Perkin-Elmer Cetus) and a priming oligomer (5'-GTA CCT CAT GAG CCA CAT AAT ACC ATG-3', SEQ.ID:46:) specific for B7 located downstream of the B7 translational open reading frame. B7 was amplified by PCR using the following sense and antisense PCR oligomers: 5'-GGT ACA AGA TCT ACC ATG GCT TGC AAT TGT CAG TTG ATG C-3', SEQ.ID:47:, and 5'-CCA CAT AGA TCT CCA TGG GAA CTA AAG GAA GAC GGT CTG TTC-3', SEQ.ID:48:, respectively. These oligomers provide BglII restriction enzyme sites at the ends of the insert as well as a Kozak translation initiation sequence containing an NcoI restriction site and an additional NcoI site located immediately prior to the 3'-terminal BglII site. NcoI digestion yielded a fragment suitable for cloning into pGEM-3-IRES which had been digested with NcoI. The resulting vector, pGEM-3-IRES-B7, contains an IRES-B7 cassette which can easily be transferred to V1Jns-X, where X represents an antigen-encoding gene.

D. pGEM-3-X-IRES-GM-CSF: (where X=any antigenic gene) This vector contains a cassette analogous to that described in item C above except that the gene for the immunostimulatory cytokine, GM-CSF, is used rather than B7. GM-CSF is a macrophage differentiation and stimulation cytokine which has been shown to elicit potent antitumor T cell activities in vivo [G. Dranoff et al., Proc. Natl. Acad. Sci. USA, 90, 3539 (1993).

E. pGEM-3-X-IRES-IL-12: (where X=any antigenic gene) This vector contains a cassette analogous to that described in item C above except that the gene for the immunostimulatory cytokine, IL-12, is used rather than B7. IL-12 has been demonstrated to have an influential role in shifting immune responses towards cellular, T cell-dominated pathways as opposed to humoral responses [L. Alfonso et al., Science, 263, 235, 1994].

F. V1Jns-HIV$_x$ gp160/IRES/rev$_{IIIB}$ (SD): This vector is analogous to the one described in I.B. above except that gp160 genes derived from various clinical strains are used rather than gp160 derived from laboratory strain IIIB.

G. V1Jns-PR8/34/HA-IRES-SIV p28 gag

This construct provides an influenza hemagglutination gene (HA) in concert with the SIV p28 gag gene for coordinate expression via the IRES element. The PR8/34/HA gene was amplified by PCR using the following sense and antisense oligomers: 5'-GGT ACA AGA TCT ACC ATG AAG GCA AAC CTA CTG GTC CTG-3', SEQ.ID:49:, and 5'-CCA CAT AGA TCT GAT ATC CTA ATC TCA GAT GCA TAT TCT GCA CTG C-3', SEQ.ID:50:, respectively. The resulting DNA segment has BglII restriction enzyme sites at either end and an EcoRV site at the 3'-terminus. After BglII digestion this gene was cloned into V1Jns which had been digested with BglII followed by alkaline phosphatase treatment. SIV p28 gag was excised from V1J-SIV p28 gag by NcoI and BglII digestion. pGEM-IRES was digested with NcoI and BamHI for directional ligation with p28 gag/NcoI/BglII. The IRES-p28 gag cassette is removed by restriction digestion with SmaI and HindIII and ligated into the EcoRV site of V1Jns-A/PR8/HA. In vivo coordinate expression of these genes allows generation of potent antibody responses by PNV vaccination (HA), with requisite T cell help, which provides such help in a local environment to potentiate the CTL response of the second gene product (SIV p28 gag). This construct also demonstrates the ability to use the PNV and method of this invention to generate immune responses against multiple antigens whether or not related to HIV. Those skilled in the art will appreciate that this type of construct could be mixed with other, bi- or tri-cistronic constructs to produce a multivalent combination polynucleotide vaccine.

H. V1Jns-tPA-gp160$_{IIIB}$/IRES/SIV p28 gag: V1Jns-tPA-gp160$_{IIIB}$ was digested with EcoRV, treated with calf intestinal alkaline phosphatased, and ligated with IRES-SIV p28 gag which had been removed from pGEM-3-IRES-SIV p28 by restriction enzyme digestion using SmaI and HindII. In vivo coordinate expression of these genes allows coupling a protein which generates strong helper T cell responses (gp160) to one which provides Class I MHC-associated CTL epitopes (SIV p28 gag). This vaccine is designed for immunization of rhesus monkeys for generation of anti-env neutralizing antibodies and CTL as well as anti-SIV gag CTL. These monkeys are subsequently challenged with appropriate SHIV viral challenges [see J. Li et al., *J. A.I.D.S.* 5, 639–646 (1992)].

I. V1Jns-tPA-gp120$_{IIIB}$/IRES/SIV p28 gag: This vector is constructed exactly as V1Jns-tPA-gp160$_{IIIB}$/IRES/SIV p28 gag except that V1Jns-tPA-gp120$_{IIIB}$ is used in place of the gp160 gene. Vaccination and SHIV challenge are conducted as described above.

J. V1Jns-tPA-gp 120$_{IIIB}$/IRES/HIV gag/IRES/rev: This vector is similar to those described above except that a tricistron provides gag and rev expression in addition to gp120.

K. V1Jns-tPA-gp160$_{IIIB}$/IRES/HIV gag/IRES/rev: This vector is similar to those described above except that a tricistron provides gag and rev expression in addition to gp160.

EXAMPLE 6

Assay for HIV Cytotoxic T-Lymphocytes:

The methods described in this section illustrate the assay as used for vaccinated mice. An essentially similar assay can be used with primates except that autologous B cell lines must be established for use as target cells for each animal. This can be accomplished for humans using the Epstein-Barr virus and for rhesus monkey using the herpes B virus.

Peripheral blood mononuclear cells (PBMC) are derived from either freshly drawn blood or spleen using Ficoll-Hypaque centrifugation to separate erythrocytes from white blood cells. For mice, lymph nodes may be used as well. Effecter CTLs may be prepared from the PBMC either by in vitro culture in IL-2 (20 U/ml) and concanavalin A (2 μg/ml) for 6–12 days or by using specific antigen using an equal number of irradiated antigen presenting cells. Specific antigen can consist of either synthetic peptides (9–15 amino acids usually) that are known epitopes for CTL recognition for the MHC haplotype of the animals used, or vaccinia virus constructs engineered to express appropriate antigen. Target cells may be either syngenic or MHC haplotype-matched cell lines which have been treated to present appropriate antigen as described for in vitro stimulation of the CTLs. For Balb/c mice the P18 peptide (ArgIleHisIleGlyProGlyArgAlaPheTyrThrThrLysAsn, SEQ.ID:δ 1:, for HIV MN strain) can be used at 10 μM concentration to restimulate CTL in vitro using irradiated syngenic splenocytes and can be used to sensitize target cells during the cytotoxicity assay at 1–10 μM by incubation at 37° C. for about two hours prior to the assay. For these H-$2^d$ MHC haplotype mice, the murine mastocytoma cell line, P815, provides good target cells. Antigen-sensitized target cells are loaded with $Na^{51}CrO_4$, which is released from the interior of the target cells upon killing by CTL, by incubation of targets for 1–2 hours at 37° C. (0.2 mCi for ~$5\times10^6$ cells) followed by several washings of the target cells. CTL populations are mixed with target cells at varying ratios of effectors to targets such as 100:1, 50:1, 25:1, etc., pelleted together, and incubated 4–6 hours at 37° C. before harvest of the supernatants which are then assayed for release of radioactivity using a gamma counter. Cytotoxicity is calculated as a percentage of total releasable counts from the target cells (obtained using 0.2% Triton X-100 treatment) from which spontaneous release from target cells has been subtracted.

EXAMPLE 7

Assay for HIV Specific Antibodies:

ELISAs were designed to detect antibodies generated against HIV using either specific recombinant protein or synthetic peptides as substrate antigens. 96 well microtiter plates were coated at 4° C. overnight with recombinant antigen at 2 μg/ml in PBS (phosphate buffered saline) solution using 50 μl/well on a rocking platform. Antigens consisted of either recombinant protein (gp120, rev: Repligen Corp.; gp160, gp41: American Bio-Technologies, Inc.) or synthetic peptide (V3 peptide corresponding to virus isolate sequences from IIIB, etc.: American Bio-Technologies, Inc.; gp41 epitope for monoclonal antibody 2F5). Plates were rinsed four times using wash buffer (PBS/0.05% Tween 20) followed by addition of 200 μl/well of blocking buffer (1% Carnation milk solution in PBS/0.05% Tween-20) for 1 hr at room temperature with rocking. Pre-sera and immune sera were diluted in blocking buffer at the desired range of dilutions and 100 μl added per well. Plates were incubated for 1 hr at room temperature with rocking and then washed four times with wash buffer. Secondary antibodies conjugated with horse radish peroxidase, (anti-rhesus Ig, Southern Biotechnology Associates; anti-mouse and anti-rabbit Igs, Jackson Immuno Research) diluted 1:2000 in blocking buffer, were then added to each sample at 100 μl/well and incubated 1 hr at room temperature with rocking. Plates were washed 4 times with wash buffer and then developed by addition of 100 μl/well of an o-phenylenediamine (o-PD, Calbiochem) solution at 1 mg/ml in 100 mM citrate buffer at pH 4.5. Plates were read for absorbance at 450 nm both kinetically (first ten minutes of reaction) and at 10 and 30 minute endpoints (Thermo-max microplate reader, Molecular Devices).

EXAMPLE 8

Assay for HIV Neutralizing Antibodies:

In vitro neutralization of HIV isolates assays using sera derived from vaccinated animals was performed as follows. Test sera and pre-immune sera were heat inactivated at 56° C. for 60 min before use. A titrated amount of HIV-1 was added in 1:2 serial dilutions of test sera and incubated 60 min at room temperature before addition to $10^5$ MT-4 human lymphoid cells in 96 well microtiter plates. The virus/cell mixtures were incubated for 7 days at 37° C. and assayed for virus-mediated killing of cells by staining cultures with tetrazolium dye. Neutralization of virus is observed by prevention of virus-mediated cell death.

EXAMPLE 9

Protection of Chimpanzees upon Challenge with Virulent HIV-1:

The only animal HIV challenge model to date is with chimpanzees. While chimpanzees do not develop HIV-related immunodeficiency disease they can be infected with some HIV viral isolates. The most common strain used to date in this model is the IIIB strain (BH10) although challenge stocks for other isolates are being developed, e.g., for SF2. We envision vaccination of chimpanzees in an analogous manner to vaccination in other nonhuman primates using HIV env and gag-pol constructs derived from the HIV-1 IIIB strain (HXB2 clone) as described within this document to achieve anti-HIV humoral and cellular responses. While the BH10 challenge virus for chimpanzees is IIIB derived as are our vaccination construct genes, there is heterogeneity within this virus so that HXB2 is only one of at least three variations of IIIB present in the viral inoculum. Thus, the IIIB challenge experiment of HXB2 gene vaccinated monkeys is not completely homologous.

We are vaccinating chimpanzees 3–5 rounds with polynucleotide HIV gene vaccines with doses of 0.1–3 mg of plasmid/round. After characterization of vaccine-induced humoral and CTL anti-HIV responses these monkeys are challenged with 10 to 140 $CID_{50}$ (50% chimpanzee infectious dose) by an intravenous administration of HIV-$1_{IIIB}$ inoculum diluted 1:25 in physiologic saline just prior to use. Infection of chimpanzees is monitored by detection of HIV-1 virus specific DNA sequences using DNA derived from PBMC obtained from test chimpanzees. (see Example 10 for details). Vaccine-mediated protection can be described as a range of responses to challenge virus from complete sterilizing immunity (inability to detect virus post infection) to significant reductions and/or delay in viremia induced by the challenge stock. While sterilizing immunity is clearly the most preferred response to vaccination, reduced or delayed viremia may significantly influence onset of immunodeficiency disease in human vaccinees.

EXAMPLE 10

Isolation of Genes from Clinical HIV Isolates:

HIV viral genes were cloned from infected PBMC's which had been activated by ConA treatment. The preferred method for obtaining the viral genes was by PCR amplification from infected cellular genome using specific oligomers flanking the desired genes. A second method for obtaining viral genes was by purification of viral RNA from the supernatants of infected cells and preparing cDNA from this material with subsequent PCR. This method was very analogous to that described above for cloning of the murine B7 gene except for the PCR oligomers used and random hexamers used to make cDNA rather than specific priming oligomers.

Genomic DNA was purified from infected cell pellets by lysis in STE solution (10 mM NaCl, 10 mM EDTA, 10 mM Tris-HCl, pH 8.0) to which Proteinase K and SDS were added to 0.1 mg/ml and 0.5% final concentrations, respectively. This mixture was incubated overnight at 56° C. and extracted with 0.5 volumes of phenol:chloroform:isoamyl alcohol (25:24:1). The aqueous phase was then precipitated by addition of sodium acetate to 0.3 M final concentration and two volumes of cold ethanol. After pelleting the DNA from solution the DNA was resuspended in 0.1×TE solution (1×TE=10 mM Tris-HCl, pH 8.0, 1 mM EDTA). At this point SDS was added to 0.1% with 2 U of RNAse A with incubation for 30 minutes at 37° C. This solution was extracted with phenol/chloroform/isoaniyl alcohol and then precipitated with ethanol as before. DNA was suspended in 0.1×TE and quantitated by measuring its ultraviolet absorbance at 260 nm. Samples were stored at −20° C. until used for PCR.

PCR was performed using the Perkin-Elmer Cetus kit and procedure using the following sense and antisense oligomers for gp160: 5'-GA AAG AGC AGA AGA CAG TGG CAA TGA-3', SEQ.ID:52: and 5'-GGG CTT TGC TAA ATG GGT GGC AAG TGG CCC GGG C ATG TGG-3', SEQ.ID:53:, respectively. These oligomers add an SrfI site at the 3'-terminus of the resulting DNA fragment. PCR-derived segments are cloned into either the V1Jns or V1R vaccination vectors and V3 regions as well as ligation junction sites confirmed by DNA sequencing.

EXAMPLE 11

Sequences Across Vaccine Construct Junctions:

Genes were cloned according to Example 10. In each case, the junction sequences from the 5' promoter region (CMVintA) into the cloned gene was sequenced using the primer:

CMVinta primer 5'-CTA ACA GAC TGT TCC TTT CCA TG-3', SEQ. ID:54:, which generates the sequence of the coding sequence. This is contiguous with the terminator/coding sequence, the junction of which is also shown. This sequence was generated using the primer: BGH primer 5'-GGA GTG GCA CCT TCC AGG-3', SEQ. ID:55:, which generates the sequence of the non-coding strand. In every case, the sequence was checked against known sequences from GENBANK for cloned and sequenced genes from these or other HIV isolates. The position at which the junction occurs is demarcated by a "/", which does not represent any discontinuity in the sequence. The first "ATG" encountered in each sequence is the translation initiation codon for the respective cloned gene. Each sequence provided represents a complete, available, expressible DNA construct for the designated HIV gene. The nomenclature follows the convention: "Vector name-HIV strain-gene". The biological efficacy of each of these constructs is shown in the same manner as in the foregoing Examples:

Sequence Across the 5' Junctions of CMVintA and the HIV Genes and Across the 3' Junctions of the HIV Genes and the BGH Terminator Expression Constructs, Using Different HIV Strains and Proteins:

1. V1Jns-rev$_{IIIB}$:

```
SEQ.ID:56
5'-GGA GAC AGC GACGAA GAC CTC CTC AAG GCA GTC AGA CTC ATC AAG-3'
     rev....
```

(Sequence begins at the 5'-terminus within the PCR oligomer. See #7 below for complete rev 5'-terminus sequence)

```
SEQ.ID:57:
5'-GAT GGC TGG CAA CTA GAA GGC ACA GCA GAT CT/GAT ATC GCA CTA TTC TTT AGC TCC TGA CTC CAA TAT TGT-3'
       BGH                                      rev...
```

2. V1Jns-gp160$_{IIIB}$:

```
SEQ.ID:58:
5'-CTT AGA TC/A ACC ATG AGA GTG AAG GA GAA ATA TCA GCA CTT GTG
CMVinta              gp160

GAG ATG GGG GTG GAG ATG GGG CAC CAT GCT CCT TGG GAT GTT GAT GAT CTG TAG TGC TAC AGA AAA ATT GTG GGT-3'
```

-continued

```
SEQ.ID:59:
5'-CTG GCA ACT AGA AGG CAC AGC AGA TC/A GAT AGT GTC CCC ATC TTA TAG CAA AAT CCT TTC CAA GCC CTG TCT
     BGH                                    gp160

TAT TCT-3'
```

3. pGEM-3-IRES: [sequenced using SP6 (5'-GAT TTA GGT GAC ACT ATA G-3', SEQ.ID:60:) and T7 (5'-TAA TAC GAC TCA CTA TAG GG-3', SEQ.ID:61:) primers, Promega Biotech]

```
SEQ.ID:62:
5'-CAT GCC TGC AGG TCG ACT CTA/ AAT TCC G...
     pGEM-3 (SP6)            IRES

SEQ.ID:63:
5'-A CCC GGG GAT CCT CT/A GCG CGC TTG TCT CTT GTT
       pGEM-3 (T7)               IRES

CCA...
```

4. pGEM-3-IRES/rev$_{IIIB}$: [sequenced using T7 sequencing primer (Promega) for rev 3'-end, and] IRES 3'-oligomer (5'-GG GAC GTG GTT TTC C-3', SEQ.ID:64:) for IRES/rev junction]

```
SEQ.ID:65:
5'-TAT GGC CAC AAC C/AT GGC AGG AAG AAG CGG AGA CAG CGA CGA AGA CCT CCT CAA GGC AGT CAG ACT -3'
       IRES                 rev

SEQ.ID:66:
5'-CTC GAG CCA TGG GCC CCT/ AGA CTA TAG CGT GAT AAG AAA TCG AGG ACT GAG GTT ATA ACA TCC TCT AAG GTG GTT
      pGEM-3                 rev

ATA AAC TCC CGA AGG-3'
```

5. pGEM-3-RRE/IRES/rev: [using SP6 sequencing oligomer (Promega) and IRES 5'-oligomer, 5'-G CTT CGG CCA GTA ACG-3', SEQ.ID:67:]

```
SEQ.ID:68:
5'-TTG CAT GCC TGC AGG T/ GGT ACA TGA TCA GAT ATC G CCC GGG /C CGA GAT CTT CAG ACT TGG AGG AGG AGA TAT
     pGEM-3                  RRE                            IRES-5'

GAG GGA CAA TTG GAG-3'

SEQ.ID:69:
5'-GGG GCG GAA TT/T AGA GTC A/ATT GAT CAG CTT GTG TAA TTG TTA ATT TCT CTG TCC CAC TCC ATC CAG GTC GTG
                                             RRE-3'

TGA TTC...-3'
```

6. V1Jns-(tat/rev SD): [used for V1Jns-gp160$_{IIIB}$/IRES/rev$_{IIIB}$ (SD) and V1Jns-gp160$_{IIIB}$(SD); sequenced using an oligomer complementary to gp160 reading towards 5'-end of gp160 and into CMVintA: 5-CCA TCT CCA CAA GTG CTG-3', SEQ.ID:70:]

```
SEQ.ID:71:
5'-AGA TCT A AGG ACG GTG ACT GCA/TGT ACT ACT TAC TGC TTT GAT AGA GGA CGG TGA/CTG CAG AAA AGA CCC ATG
       CMVintA                         tat/rev SD                               CMVintA

GAA A-3'
```

7. V1Jns-g IRES/rev$_{IIIB}$ (SD): [gp160/IRES junction sequenced using IRES 5'-oligomer, 5'-G CTT CGG CCA GTA ACG-3', SEQ.ID:72:]

```
SEQ.ID:73:
5'-GGC ACA GCA GAT C/AG ATG GGG ATC TGA TA TCG CAC TAT TCT TTA GCT CCT GAC TCC TGA CTC-3'
      BGH                   rev

SEQ.ID:74:
5'-GGA ATT/ TGA GTC ATC/CCC ATC TTA TAG CAA AAT CCT TTC CAA-3'
      IRES                       gp160

8. V1JnS-gag-prtIIIB (SD)

SEQ.ID:75:
5'-CTT AGA TC/C CCG CAC GGC AAG AGG CGA GGG GCG GCG ACT GGT-3'
       CMVintA                  gag (SD)

SEQ.ID:76:
5'-GGC ACA GCA GAT C/CGC CCG GGC TTA CAT CTC TGT ACA AAT TTC TAC TAA TGC TTT TAT TTT TCT TCT GTC...-3'
      BGH                       prt
```

9. V1Jns-gag-prt$_{IIIB}$:

```
SEQ.ID:77:
5'-CTT AGA TC/CAC CAT GGG TGC GAG AGC GTC AGT ATT AA GCG GGG GGA GAA TTA GAT CGA TGG GAA AAA ATT...-3'
CMVintA                    gag

SEQ.ID:78:
5'-GGC ACA GCA GAT C/CGC CCG GGC TTA CAT CTC TGT ACA AAT TTC TAC TAA TGC TTT TAT TTT TCT TCT GTC...-3'
      BGH                         prt
```

10. V1Jns-tPA:

```
SEQ.ID:79:
5'-TCA CCG TCC TTA GAT C/ACC ATG GAT GCA ATG AAG AGA GGG CTC TGC TGT GTG CTG CTG CTG TGT GGA GCA GTC
     CMVintA                    tPA leader                           BGH

TTC GTT TCG CCC AGC GA/G ATC TGC TGT GCC TTC TAG TTG CCA GCC-3'
```

11. V1Jns-tPA-gp120$_{MN}$:

```
SEQ.ID:80:
5'-TTC GTT TCG CCC AGC GA/TCA CAG AAA AAT TGT GGG TCA CAG TC-3'
      tPA                       gp120MN

SEQ.ID:81:
5'-GGC ACA GCA GAT C/CAC GTG TTA GCG CTT TTC TCT CTC CAC CAC-3'
      BGH                     gp120MN
```

12. V1J-SIV$_{MAC251}$ p28 gag

```
SEQ.ID:82:
5'-TCA CCG TCC TTA GAT CT/ACC ATG GGA CCA GTA CAA CAA ATA GGT GGT AAC TAT GTC CAC CTG CCA TTA AGC CCG
       CMVintA                  p28 gag...

AGA ACA-3'

SEQ ID:83:
5'-GGC ACA GCA GAT CT/TTA CAT TAA TCT AGC CTT CTG TCC CGG TCC-3'
      BGH                       p28 gag
```

13. V1J-$SIV_{MAC251}$nef

```
SEQ.ID:84:
5'-TCA CCG TCC TTA GAT C/GGT ACA ACC ATG GGT GGA GCT ATT TCC ATG AGG CAA TCC AAG CCG GCT GGA GAT CTG
      CMVintA                              nef.....

ACA GAA A-3'

SEQ ID:85:
5'-GGC ACA GCA GAT CA/C CTA GGT TAG CCT TCT TCT AAC CTC TTC CTC TGA CAG GCC TGA CTT GCT TCC AAC TCT
      BGH               nef....

TCT GGG TAT CTA G-3'
```

14. V1Jns-tat/rev/env:

```
SEQ.ID:86:
5'-ACC GTC CTT AGA T/TC GAC ATA GCA GAA TAG GCG TTA CTC GAC AGA GGA GAG CAA GAA ATG GAG CCA GTA GAT
     CMVintA              tat/rev/env

CCT AGA CTA GAG CCC TGG-3'

SEQ.ID:87:
5'-GGC ACA GCA GAT C/C GAG ATG CTG CTC CCA CCC CAT CTG CTG-3'
      BGH                tat/rev/env
```

EXAMPLE 12

T Cell Proliferation Assays

PBMCs can be obtained as described in Example 6 from above and tested for recall responses to specific antigen as determined by proliferation within the PBMC population. Proliferation is monitored using $^3$H-thymidine which is added to the cell cultures for the last 18–24 hours of incubation before harvest. Cell harvesters retain isotope-containing DNA on filters if proliferation has occurred while quiescent cells do not incorporate the isotope which is not retained on the filter in free form. For either rodent or primate species $4\times10^5$ cells are plated in 96 well microtiter plates in a total of 200 $\mu$l of complete media (RPMI/10% fetal calf serum). Background proliferation responses are determined using PBMCs and media alone while nonspecific responses are generated by using lectins such as phytohaemagglutin (PHA) or concanavalin A (ConA) at 1–5 $\mu$g/ml concentrations to serve as a positive control. Specific antigen consists of either known peptide epitopes, purified protein, or inactivated virus. Antigen concentrations range from 1–10 $\mu$M for peptides and 1–10 $\mu$g/ml for protein. Lectin-induced proliferation peaks at 3–5 days of cell culture incubation while antigen-specific responses peak at 5–7 days. Specific proliferation occurs when radiation counts are obtained which are at least three-fold over the media background and is often given as a ratio to background, Or Stimulation Index (SI). HIV gp160 is known to contain several peptides known to cause T cell proliferation of gp160/gp120 immunized or HIV-infected individuals. The most commonly used of these are: T1 (LysGlnIleIleAsnMetTrpGlnGluValGlyLysAlaMetTyrAla, SEQ.ID:88:); T2 (HisGluAspIleIleSerLeuTrpAspGlnSerLeuLys, SEQ.ID:89:); and, TH4 (AspArgValIleGluValValGlnGlyAalTyr ArgAlaIleArg, SEQ.ID:90:). These peptides have been demonstrated to stimulate proliferation of PBMC from antigen-sensitized mice, nonhuman primates, and humans.

REFERENCES

L. Arthur et al., J. Virol. 63, 5046 (1989). [chimp/HIV challenge model/virus neut. assay]

T. Maniatis et al., Molec. cloning: a lab. manual, p. 280 Cold Spring Harbor

Lab., CSH, NY (1982) [genomic DNA purif.]

E. Emini et al., J. Virol. 64, 3674 (1990) [chimp challenge, neut assay]

EXAMPLE 13

Vector V1R Preparation

In an effort to continue to optimize our basic vaccination vector, we prepared a derivative of V1Jns which was designated as V1R. The purpose for this vector construction was to obtain a minimum-sized vaccine vector, i.e., without unnecessary DNA sequences, which still retained the overall optimized heterologous gene expression characteristics and high plasmid yields that V1J and V1Jns afford. We determined from the literature as well as by experiment that (1) regions within the pUC backbone comprising the *E. coli* origin of replication could be removed without affecting plasmid yield from bacteria; (2) the 3'-region of the $kan^r$ gene following the kanamycin open reading frame could be removed if a bacterial terminator was inserted in its stead; and, (3) ~300 bp from the 3'-half of the BGH terminator could be removed without affecting its regulatory function (following the original KpnI restriction enzyme site within the BGH element).

V1R was constructed by using PCR to synthesize three segments of DNA from V1Jns representing the CMVintA promoter/BGH terminator, origin of replication, and kanamycin resistance elements, respectively. Restriction enzymes unique for each segment were added to each segment end using the PCR oligomers: SspI and XhoI for CMVintA/BGH; EcoRV and BamHI for the $kan^r$ gene; and, BclI and SalI for the $ori^r$. These enzyme sites were chosen because they allow directional ligation of each of the PCR-derived DNA segments with subsequent loss of each site:

EcoRV and SspI leave blunt-ended DNAs which are compatible for ligation while BamHI and BclI leave complementary overhangs as do SalI and XhoI. After obtaining these segments by PCR each segment was digested with the appropriate restriction enzymes indicated above and then ligated together in a single reaction mixture containing all three DNA segments. The 5'-end of the ori $^r$ was designed to include the T2 rho independent terminator sequence that is normally found in this region so that it could provide termination information for the kanamycin resistance gene. The ligated product was confirmed by restriction enzyme digestion (>8 enzymes) as well as by DNA sequencing of the ligation junctions. DNA plasmid yields and heterologous expression using viral genes within V1R appear similar to V1Jns. The net reduction in vector size achieved was 1346 bp (V1Jns=4.86 kb; V1R=3.52 kb), see FIG. 11, SEQ.ID: 100:.

PCR oligomer sequences used to synthesize V1R (restriction enzyme sites are underlined and identified in brackets following sequence):

(1) 5'-GGT ACA AATATT GG CTA TTG GCC ATT GCA TAC G-3' [Sspl], SEQ.ID:91:,
(2) 5'-CCA CAT CTCGAG GM CCG GGT CAA TTC TTC AGC ACC-3' [Xhol], SEQ.ID:92:
(for CMVintA/BGH segment)
(3) 5'-GGT ACA GATATC GGA AAG CCA CGT TGT GTC TCA AAA TC-3'[EcoRV], SEQ.ID:93:
(4) 5'-CCA CAT GGATCC G TAA TGC TCT GCC AGT GTT ACA ACC-3' [BamHI], SEQ.ID:94:
(for kanamycin resistance gene segment)
(5) 5'-GGT ACA TGATCA CGT AGA AAA GAT CAA AGG ATC TTC TTG-3'[Bcll], SEQ.ID:95:,
(6) 5'-CCA CAT GTCGAC CC GTA MA AGG CCG CGT TGC TGG-3' [Sall], SEQ.ID:96:
(for E.*coli* origin of replication)

Ligation junctions were sequenced for V1R using the following oligomers:

5'-GAG CCA ATA TAA ATG TAC-3', SEQ.ID:97: [CMVintA/kan$^r$ junction]

5'-CAA TAG CAG GCA TGC-3', SEQ.ID:98: [BGH/ori junction] 5'-G CAA GCA GCA GAT TAC-3', SEQ.ID:99: [ori/kan$^r$ junction]

EXAMPLE 14

The HIV genes which appear to be the most important for PNV development are env and gag. Both env and gag require the HIV regulatory protein, rev, for either viral or heterologous expression. Because efficient expression of these gene products is essential for PNV function, two types of vectors, rev-dependent and rev-independent, were tested for vaccination purposes. Unless stated otherwise, all genes were derived from the HIV-1 (IIIB) laboratory isolate.

A. env: Depending upon how large a gene segment is used, varying efficiencies of rev-independent envy expression may be achieved by replacing the native leader peptide of env with the leader peptide from the tissue-specific plasminogen activator (tPA) gene and expressing the resulting chimeric gene behind the CMV promoter with the CMV intronA. V1Jns-tPA-gp120 is an example of a secreted gp120 vector constructed in this fashion which functions to yield anti-gp120 immune responses in vaccinated mice and monkeys.

Published reports indicate that membrane-anchored proteins may induce a more substantial antibody responses compared to secreted proteins. Membrane-anchored proteins may also induce antibody responses to additional immune epitopes. To test this hypothesis, V1Jns-tPA-gp160 and V1Jns-rev/env were prepared. The tPA-gp160 vector produced detectable quantities of gp160 and gp120, without the addition of rev, as shown by immunoblot analysis of RD cells transfected in vitro, although expression was much lower than that obtained for rev/env, a rev-dependent gp160-expressing plasmid. This may be due to the presence of inhibitory regions, which confer rev dependence upon the gp160 transcript occur at multiple sites within gp 160 including at the COOH-terminus of gp41.

Vectors containing truncated forms of tPA-gp160, tPA-gp143 and tPA-gp150, designed to increase the overall expression of env by elimination of these inhibitory sequences, were prepared. The truncated gp 160 vectors lack intracellular gp41 regions containing peptide motifs (such as leu—leu) which are known to cause diversion of membrane proteins to the lysosomes rather than the cell surface. Thus, gp143 and gp150 may be expected to increase the transport of protein to the cell surface compared to full-length gp 160 where these proteins may be better able to elicit anti-gp160 antibodies following DNA vaccination.

A quantitative ELISA for gp160/gp120 expression in cell transfectants was developed to determine the relative expression capabilities for these vectors as well as for an additional vector which combines the features of tPA-gp160 and rev/env (vector rev/tPA-gp 160). In vitro transfection of 293 cells followed by quantitation of cell-associated vs. secreted/released gp120 yielded the following results:

(1) for the analogous plasmid pair, rev/env and rev/tPA-gp 160, substitution of the native leader peptide in gp160 with the tPA leader sequence did not increase the total expression of gp160 or the amount of released gp120. This suggests that the leader peptide is not responsible for inefficient trafficking of gp160 to the cell surface in these cells.
(2) tPA-gp 160 expresses 5–10× less gp 160 than rev/env with similar proportions retained intracellularly vs. trafficked to the cell surface.
(3) tPA-gp143 gave 3–6× greater secretion of gp120 than rev/env with only low levels of cell-associated gp143 confirming that the cytoplasmic tail of gp160 causes intracellular retention of gp160 which can be overcome by partial deletion of this sequence.
(4) tPA-gp150 gave only low levels of gp160 in both cells and media, indicating either a problem with this construct or inherent instability of the truncated protein.

tPA-gp120 derived from a primary HIV isolate (containing the North American consensus V3 peptide loop; macrophage tropic and nonsyncytia-inducing phenotypes) gave high expression/secretion of gp120 with transfected 293 cells demonstrating that it was cloned in a functional form.

EXAMPLE 15

Serological Assays

A. Antibody Responses:

1. gp120 PNVs

An ID vs. IM vaccination experiment in mice was completed using V1Jns-tPA-gp120 (100, 10, 1 $\mu$g: 3×). ID vaccination appeared superior at the lower doses following initial rounds but all doses were equivalent after three rounds.

Rhesus monkeys (RHM) and African green monkeys (AGM) were vaccinated with the V1Jns-tPA-gp120 (MN) PNV. Peak GMTs for gp120 antibodies differed by more than five-fold between these two primate species: 1780 (AGM) and 310 (RHM). These results indicate that substantially larger antibody titers can be elicited in AGM compared to RHM and suggest that higher HIV neutralization titers may be obtained by AGM vaccination.

2. gp160 PNVs: V1Jns-rev/env vaccination (IM) of mice did not yield antibodies to gp160 until three injections while ID vaccination yielded responses after one round which remained higher than those produced by IM throughout the experiment (GMTs=2115 (ID) and 95 (IM); 200 μg/mouse). This suggests that rev-dependent constructs can function as immunogens better by the ID route.

RHM receiving ID or IM inoculations with V1Jns-rev/env showed peak GMTs=790 and 140, respectively, following 4–5 inoculations (2 mg/round). These results agree with those found for mice showing that this rev dependent PNV has greater efficacy for antibody generation by ID vaccination although the rev-independent construct V1Jns-tPA-gp120 did not. RHM receiving tPA-gp160 DNA (IM) showed lower, more variable antibody responses than those receiving rev/env which corroborate our determination that this vector expresses gp160 4–7× less efficiently than rev/env.

B. In Vitro Virus Neutralization

An infectivity reduction neutralization assay (p24 gag production readout) using HIV(MN) as a virus source was performed by Quality Biologicals, Inc. (QBI). At low virus input (100 $TCID_{50}$) complete neutralization was seen at 1/10 dilutions of sera for all three antisera with at least 80–90% reduction in virus production observed in all samples up to 1/80 dilutions as compared to matched prebleed sera. However, at higher virus input (1000 $TCID_{50}$), no neutralization was observed for any sample.

RHM were tested for HIV (IIIB) neutralization (QBI), using 100 $TCID_{50}$ of input virus, following vaccinations with tPA-gp120 (IIIB) DNA. In two different experiments the best neutralization results were obtained at serum dilutions of 10 (40–99% reduction of p24 gag) with gag reduction observed in some samples at dilutions as high as 80-fold. The most consistent samples in this assay had anti-gp120 antibody ELISA endpoint titers of at least 2000–3000.

RHM were similarly tested for HIV (IIIB) neutralization (QBI) following vaccinations with rev/env DNA. Overall, low levels of neutralization were observed: two of three RHM showed neutralization ranging up to 84% at a serum dilution of 10 with p24 gag reduction observed at subsequent dilutions of 20 or 40 while one sample did not show any evidence of neutralization. These samples had anti-gp120 antibody ELISA titers of 700–800 indicating that this is the minimum useful titer range for testing sera derived from gp160 DNA vaccine experiments in neutralization assays.

C. Facilitators for Enhanced Immunity

Several experiments were initiated to test plasmid DNA formulations which have been reported to enhance DNA uptake following vaccination and increase either reporter gene expression or immune responses in mouse or monkey vaccinees. Hypertonic sucrose (up to 20–25%, w/v) DNA solutions have been reported to give more uniform distribution of DNA uptake, as evidenced by reporter gene expression, and was used in experiments in which substantial gp160-specific antibodies were elicited in rodents and nonhuman primates vaccinated with a rev/gp160 plasmid. The anesthetic, bupivicaine (0.25–0.75%, w/v), has also been reported to significantly enhance DNA vaccine-mediated immune responses in mice and nonhuman primates when used either as a pretreatment for IM injection, or as by co-injection with DNA in isotonic saline solution.

Our initial results with bupivicaine showed that substantial mortality was caused by IM treatment with 0.5% solutions. Mortality varied depending on the volume of solution used and whether the mice were injected while under anesthetic (≧0.1 mL w/o anesthetic gave highest mortality). Our experiments have used 0.25% solutions without significant mortality either as a pre-treatment or a co-treatment and using gp120 or rev/env PNVs. A preliminary experiment using bupivicaine as a pre-treatment for three vaccination rounds did not show any enhancement of immune responses relative to control mice while a larger experiment using both ID and IM sites as a pre-treatment or co-treatment has not shown any increased antibody levels following one injection and appeared to decrease antibody responses in some groups. Three vaccinations are planned in the current study.

This sucrose formulation experiment tested a variety of conditions described in the literature. Sucrose concentration was tested at 10, 15, 20, and 25% in saline or PBS solution containing 0.1 mg/mL of tPA-gp120 plasmid. All samples were tested as a co-injection by IM or ID routes except for a 25% sucrose/PBS group that received this solution 15–30 minutes prior to IM DNA/PBS injection. Serum data derived from bleeds following the first vaccination did not show any enhancement of antibody responses.

EXAMPLE 16

T Lymphocyte Responses:

A. Proliferation and Cytokine Secretion

T lymphocytes which have been primed in vivo with antigen can proliferate and secrete cytokines during in vitro cell culture after exogenous addition of priming antigen. Responding T cells usually have a MHC Class II-restricted, CD4+ (helper) phenotype. Helper T cells can be functionally grouped according to the types of cytokines they secrete following stimulation by antigen: $T_H1$ cells secrete primarily IL-2 and g-interferon while $T_H2$ cells are associated with IL-4, IL-5, and IL-10 secretion. $T_H1$ lymphocytes and cytokines promote cellular immunity, including CTL and DTH responses, while $T_H2$ cells and cytokines promote B cell activation for humoral immunity. We have previously tested for these responses in mice and nonhuman primates (AGM and RHM), using $rgp120_{IIIB}$ for antigen in vitro, after vaccination with HIV tPA-gp120 PNVs and shown that T cells from vaccinees of both species exhibit proliferative responses to gp120 in vitro and that these responses are $T_H1$-like and long-lived (>6 months) in mice. These studies were continued with a rev PNV.

1. mouse studies: Mice vaccinated either 3× or 1× with 200 μg V1Jns-rev were tested for in vitro proliferation to recombinant rev (r-rev) protein. Mice vaccinated 3× showed stimulation indices (SI: ratio of proliferation of immune cells with and without immunizing antigen) of 9–12 while mice receiving IX were the same as background (SIs=2–3). Splenic T cells from all rev vaccinees, but not control mice, secreted g-interferon in response to r-rev antigen (2.4–2.8 ng/ml, 3X; 0.4–0.7 ng/ml, IX) while no IL-4 was detected in culture supernatants (detection sensitivities=47 pg/ml and 15 pg/ml for g-interferon and IL-4, respectively) showing these T cell responses to be $T_H1$-like in nature as we found for gp120 DNA vaccinees. Cytokine secretion may be a more sensitive assay than proliferation to specific antigen for determining T cell memory responses. Similar results were found for mice tested at least six months post vaccination. Antibodies to rev were not detected in any vaccinee sera as may be expected for this intracellular protein.

2. Monkey Studies: Three RHM showed strong in vitro T cell proliferation (SIs=9–30) to r-rev following two vaccinations with V1Jns-rev. No anti-rev antibodies were detected in any monkeys. These results corroborate the above mouse/rev experiments and confirm that strong T cell responses can be induced by rev PNVs without concomitant induction of antibody responses.

Further experiments using tPA-gp120 DNA vaccination of RHM showed that (i) in vitro T cell proliferation to rgp120 was obtained following one vaccination; (ii) primary responses were boosted following a second vaccination; and, (iii) similar proliferations were obtained with these vaccinees as for SHIV-infected RHM (SIs=5–70 and 5–35, respectively).

B. Anti-env Cytotoxic T Lymphocytes

Two of four RHM monkeys vaccinated with tPA-gp120 (IM) and gp 160/IRES/rev (ID) PNVs showed significant CTL activities (>20% lysis at 10:1 E/T) against homologous target cells six weeks following one vaccination. Two weeks post a second vaccination all four monkeys showed cytotoxicities ranging from 20–35% lysis at 20:1 E/T. All CTL activities in this assay design were MHC Class I restricted: removal of CD8+ T cells completely removed cytotoxicities in all four monkeys. CTL responses waned over several months and were boosted to ≧original levels with subsequent re-vaccination. These CTL activities were characterized as the most potent for vaccine-mediated responses observed in RHM.

What is claimed is:

1. A plasmid DNA polynucleotide which cannot replicate in eukaryotic cells in vivo and which comprises contiguous nucleic acid sequences capable of being expressed to produce a gene product upon introduction of the polynucleotide into eukaryotic tissues in vivo, wherein the gene product either acts as an immunostimulant or as an antigen capable of generating an immune response, wherein the nucleic acid sequences comprise:

a) a spliced REV gene;

b) a spliced sequence encoding a human immunodeficiency virus (HIV) immunogenic epitope; and, c) optionally, a sequence encoding a cytokine or a T-cell recognition element.

2. The plasmid DNA polynucleotide of claim 1 wherein the HIV immunogenic epitope of step b) is a gene product expressed from an HIV gene selected from the group of HIV genes consisting of gag, gag-protease, and env or an immunogenic subportion thereof; the cytokine is interleukin-12, and the T-cell costimulatory element is a B7 protein.

3. The plasmid DNA polynucleotide of claim 2 wherein the env immunogenic epitope is a gene product expressed from an env open reading frame selected from the group consisting of HIV gp160, HIV gp120 and HIV gp41.

4. The plasmid DNA polynucleotide of claim 2 wherein the gag immunogenic epitope is p17, p24, or p15.

5. A plasmid DNA polynucleotide comprising a first gene encoding an HIV gag, gag-protease, or env immunogenic epitope, the first gene containing a REV responsive element (RRE) or having been modified to contain an RRE, the first gene being operatively linked with a transcriptional promoter suitable for gene expression in a mammal, the first gene being linked with an internal ribosome entry site (IRES), and the IRES being linked with a second gene encoding a REV gene product, wherein said polynucleotide is non-replicating in eukaryotic cells in vivo.

6. A plasmid DNA polynucleotide which is non-replicating in eukaryotic cells in vivo, comprising:

a) a eukaryotic transcriptional promoter;

b) an open reading frame 3' to the transcriptional promoter encoding an immunogenic HIV epitope wherein the open reading frame has a splice donor sequence at the 5'-side of the open reading frame, a REV responsive element anywhere within the open reading frame, and a stop codon encoding the termination of translation of the open reading frame;

c) an internal ribosome entry site (IRES) 3' to the translation stop codon of the open reading frame;

d) an open reading frame encoding a spliced HIV REV gene at the 3' end of which is a translation stop codon;

e) optionally, 3' to the REV translation stop codon, a second IRES, followed by an open reading frame encoding immunomodulatory or immunostimulatory genes being selected from the group consisting of GM-CSF, IL-12, interferon, and a B7 protein; and, f) a transcription-termination signal 3' of the most downstream open reading frame of step d) or optionally, step e).

7. A plasmid DNA polynucleotide which is non-replicating in eukaryotic cells in vivo, comprising sequences encoding:

a) a eukaryotic transcription initiation signal;

b) an HIV gene open reading frame (ORF) preceded by a heterologous leader sequence such that expression of the HIV gene ORF does not depend on availability of the HIV REV gene product;

c) a sequence which operates as an internal ribosome entry site (IRES) 3' to the translation stop codon of the HIV ORF;

d) a sequence encoding an ORF of a T-cell costimulatory element 3' to the IRES; and e) a transcription termination signal 3' to the translation stop codon of the T-cell costimulatory element.

8. The plasmid DNA polynucleotide of claim 7 wherein the HIV gene ORF in (b) is tPAgp120 or tPAgp160.

9. A plasmid DNA polynucleotide which is non-replicating in eukaryotic cells in vivo, comprising sequences encoding:

a) a eukaryotic transcription initiation signal;

b) a first HIV gene open reading frame (ORF) preceded by a heterologous leader sequence such that expression of the HIV gene ORF does not depend on availability of the HIV REV gene product;

c) a sequence which operates as an internal ribosome entry site (IRES) 3' to the translation stop codon of the first HIV ORF;

d) a second HIV gene open reading frame (ORF) preceded by a heterologous leader sequence such that expression of the second HIV gene ORF does not depend on availability of the HIV REV gene product; and e) a transcription termination signal 3' to the translation stop codon of the second HIV gene ORF.

10. A plasmid DNA polynucleotide construct selected from the group consisting of V1Jns-(tat/rev SD), V1Jns-gp160$_{IIIB}$/IRES/rev $_{IIIB}$ (SD), V1Jns-gag-prt$_{IIIB}$ (SD), V1Jns-gag-prt$_{IIIB}$, V1J- SIV$_{MAC251}$p28 gag, V1J-SIV$_{MAC251}$,nef, and V1Jns-tat/rev/env.

11. A plasmid DNA polynucleotide which is non-replicating upon in vivo introduction into a mammalian cell and induces the co-expression of three gene products from a first cistron, a second cistron and a third cistron, wherein the first cistron contains an HIV gag gene or portion thereof which encodes a gag immunogenic epitope, the second cistron encodes a cytokine, and the third cistron encodes a T-cell costimulatory element, wherein the first, second and third cistron may be presented in any combination.

12. The plasmid DNA polynucleotide of claim 11 wherein the second cistron encodes an interleukin, an interferon, or GM-CSF, and the third cistron encodes a B7 protein.

* * * * *

SEQUENCE LISTING

```
(1) GENERAL INFORMATION:

   (iii) NUMBER OF SEQUENCES: 100


(2) INFORMATION FOR SEQ ID NO: 1:

     (i) SEQUENCE CHARACTERISTICS:
          (A) LENGTH: 35 amino acids
          (B) TYPE: amino acid
          (C) STRANDEDNESS: single
          (D) TOPOLOGY: both

    (ii) MOLECULE TYPE: peptide

   (iii) HYPOTHETICAL: NO

    (iv) ANTI-SENSE: NO

     (v) FRAGMENT TYPE: internal

    (xi) SEQUENCE DESCRIPTION: SEQ ID NO: 1:

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35


(2) INFORMATION FOR SEQ ID NO: 2:

     (i) SEQUENCE CHARACTERISTICS:
          (A) LENGTH: 35 amino acids
          (B) TYPE: amino acid
          (C) STRANDEDNESS: single
          (D) TOPOLOGY: both

    (ii) MOLECULE TYPE: peptide

   (iii) HYPOTHETICAL: NO

    (iv) ANTI-SENSE: NO

     (v) FRAGMENT TYPE: internal

    (xi) SEQUENCE DESCRIPTION: SEQ ID NO: 2:

Cys Thr Arg Pro Asn Tyr Asn Lys Arg Lys Arg Ile His Ile Gly Pro
1               5                   10                  15
```

-continued

```
Gly Arg Ala Phe Tyr Thr Thr Lys Asn Ile Ile Gly Thr Ile Arg Gln
            20                  25                  30

Ala His Cys
        35
```

(2) INFORMATION FOR SEQ ID NO: 3:

(i) SEQUENCE CHARACTERISTICS:
(A) LENGTH: 36 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 3:

```
Cys Thr Arg Pro Asn Asn Asn Thr Arg Lys Arg Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
        35
```

(2) INFORMATION FOR SEQ ID NO: 4:

(i) SEQUENCE CHARACTERISTICS:
(A) LENGTH: 35 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 4:

```
Cys Thr Arg Pro Asn Asn Asn Thr Arg Lys Gly Ile His Ile Gly Pro
1               5                   10                  15

Gly Arg Ala Phe Tyr Thr Thr Gly Lys Ile Ile Gly Asn Ile Arg Gln
            20                  25                  30

Ala His Cys
        35
```

(2) INFORMATION FOR SEQ ID NO: 5:

(i) SEQUENCE CHARACTERISTICS:
(A) LENGTH: 36 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: internal -continued (xi) SEQUENCE DESCRIPTION: SEQ ID NO: 5:

```
Cys Thr Arg Pro Ser Asn Asn Asn Thr Arg Lys Ser Ile His Ile Gly
1               5                   10                  15

Pro Gly Lys Ala Phe Tyr Ala Thr Gly Ala Ile Ile Gly Asp Ile Arg
            20                  25                  30

Gln Ala His Cys
        35
```

(2) INFORMATION FOR SEQ ID NO: 6:

(i) SEQUENCE CHARACTERISTICS:
(A) LENGTH: 35 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 6:

```
Cys Thr Arg Pro Asn Asn Asn Thr Arg Arg Ser Ile His Ile Ala Pro
1               5                   10                  15

Gly Arg Ala Phe Tyr Ala Thr Gly Asp Ile Ile Gly Asp Ile Arg Gln
            20                  25                  30

Ala His Cys
        35
```

(2) INFORMATION FOR SEQ ID NO: 7:

(i) SEQUENCE CHARACTERISTICS:
(A) LENGTH: 23 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

```
CTATATAAGC AGAGCTCGTT TAG                                              23
```

(2) INFORMATION FOR SEQ ID NO: 8:

(i) SEQUENCE CHARACTERISTICS:
(A) LENGTH: 30 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

```
GTAGCAAAGA TCTAAGGACG GTGACTGCAG                                       30
```

(2) INFORMATION FOR SEQ ID NO: 9:

-continued (i) SEQUENCE CHARACTERISTICS:
(A) LENGTH: 39 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 9:

GTATGTGTCT GAAAATGAGC GTGGAGATTG GGCTCGCAC 39

(2) INFORMATION FOR SEQ ID NO: 10:

(i) SEQUENCE CHARACTERISTICS:
(A) LENGTH: 39 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 10:

GTGCGAGCCC AATCTCCACG CTCATTTTCA GACACATAC 39

(2) INFORMATION FOR SEQ ID NO: 11:

(i) SEQUENCE CHARACTERISTICS:
(A) LENGTH: 36 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 11:

GGTACAAGAT CTACTATAGG GAGACCGGAA TTCCGC 36

(2) INFORMATION FOR SEQ ID NO: 12:

(i) SEQUENCE CHARACTERISTICS:
(A) LENGTH: 4432 base pairs
(B) TYPE: nucleic acid
(C) STRANDEDNESS: double
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 12:

TCGCGCGTTT CGGTGATGAC GGTGAAAACC TCTGACACAT GCAGCTCCCG GAGACGGTCA 60

CAGCTTGTCT GTAAGCGGAT GCCGGGAGCA GACAAGCCCG TCAGGGCGCG TCAGCGGGTG 120

TTGGCGGGTG TCGGGGCTGG CTTAACTATG CGGCATCAGA GCAGATTGTA CTGAGAGTGC 180

ACCATATGCG GTGTGAAATA CCGCACAGAT GCGTAAGGAG AAAATACCGC ATCAGATTGG 240

-continued

```
CTATTGGCCA TTGCATACGT TGTATCCATA TCATAATATG TACATTTATA TTGGCTCATG    300
TCCAACATTA CCGCCATGTT GACATTGATT ATTGACTAGT TATTAATAGT AATCAATTAC    360
GGGGTCATTA GTTCATAGCC CATATATGGA GTTCCGCGTT ACATAACTTA CGGTAAATGG    420
CCCGCCTGGC TGACCGCCCA ACGACCCCCG CCCATTGACG TCAATAATGA CGTATGTTCC    480
CATAGTAACG CCAATAGGGA CTTTCCATTG ACGTCAATGG GTGGAGTATT TACGGTAAAC    540
TGCCCACTTG GCAGTACATC AAGTGTATCA TATGCCAAGT ACGCCCCCTA TTGACGTCAA    600
TGACGGTAAA TGGCCCGCCT GGCATTATGC CCAGTACATG ACCTTATGGG ACTTTCCTAC    660
TTGGCAGTAC ATCTACGTAT TAGTCATCGC TATTACCATG GTGATGCGGT TTTGGCAGTA    720
CATCAATGGG CGTGGATAGC GGTTTGACTC ACGGGGATTT CCAAGTCTCC ACCCCATTGA    780
CGTCAATGGG AGTTTGTTTT GGCACCAAAA TCAACGGGAC TTTCCAAAAT GTCGTAACAA    840
CTCCGCCCCA TTGACGCAAA TGGGCGGTAG GCGTGTACGG TGGGAGGTCT ATATAAGCAG    900
AGCTCGTTTA GTGAACCGTC AGATCGCCTG GAGACGCCAT CCACGCTGTT TTGACCTCCA    960
TAGAAGACAC CGGGACCGAT CCAGCCTCCG CGGCCGGGAA CGGTGCATTG GAACGCGGAT   1020
TCCCCGTGCC AAGAGTGACG TAAGTACCGC CTATAGAGTC TATAGGCCCA CCCCCTTGGC   1080
TTCTTATGCA TGCTATACTG TTTTTGGCTT GGGGTCTATA CACCCCCGCT TCCTCATGTT   1140
ATAGGTGATG GTATAGCTTA GCCTATAGGT GTGGGTTATT GACCATTATT GACCACTCCC   1200
CTATTGGTGA CGATACTTTC CATTACTAAT CCATAACATG GCTCTTTGCC ACAACTCTCT   1260
TTATTGGCTA TATGCCAATA CACTGTCCTT CAGAGACTGA CACGGACTCT GTATTTTTAC   1320
AGGATGGGGT CTCATTTATT ATTTACAAAT TCACATATAC AACACCACCG TCCCCAGTGC   1380
CCGCAGTTTT TATTAAACAT AACGTGGGAT CTCCACGCGA ATCTCGGGTA CGTGTTCCGG   1440
ACATGGGCTC TTCTCCGGTA GCGGCGGAGC TTCTACATCC GAGCCCTGCT CCCATGCCTC   1500
CAGCGACTCA TGGTCGCTCG GCAGCTCCTT GCTCCTAACA GTGGAGGCCA GACTTAGGCA   1560
CAGCACGATG CCCACCACCA CCAGTGTGCC GCACAAGGCC GTGGCGGTAG GGTATGTGTC   1620
TGAAAATGAG CTCGGGGAGC GGGCTTGCAC CGCTGACGCA TTTGGAAGAC TTAAGGCAGC   1680
GGCAGAAGAA GATGCAGGCA GCTGAGTTGT TGTGTTCTGA TAAGAGTCAG AGGTAACTCC   1740
CGTTGCGGTG CTGTTAACGG TGGAGGGCAG TGTAGTCTGA GCAGTACTCG TTGCTGCCGC   1800
GCGCGCCACC AGACATAATA GCTGACAGAC TAACAGACTG TTCCTTTCCA TGGGTCTTTT   1860
CTGCAGTCAC CGTCCTTAGA TCTGCTGTGC CTTCTAGTTG CCAGCCATCT GTTGTTTGCC   1920
CCTCCCCCGT GCCTTCCTTG ACCCTGGAAG GTGCCACTCC CACTGTCCTT TCCTAATAAA   1980
ATGAGGAAAT TGCATCGCAT TGTCTGAGTA GGTGTCATTC TATTCTGGGG GGTGGGGTGG   2040
GGCAGCACAG CAAGGGGGAG GATTGGGAAG ACAATAGCAG GCATGCTGGG GATGCGGTGG   2100
GCTCTATGGG TACCCAGGTG CTGAAGAATT GACCCGGTTC CTCCTGGGCC AGAAAGAAGC   2160
AGGCACATCC CCTTCTCTGT GACACACCCT GTCCACGCCC CTGGTTCTTA GTTCCAGCCC   2220
CACTCATAGG ACACTCATAG CTCAGGAGGG CTCCGCCTTC AATCCCACCC GCTAAAGTAC   2280
TTGGAGCGGT CTCTCCCTCC CTCATCAGCC CACCAAACCA AACCTAGCCT CCAAGAGTGG   2340
GAAGAAATTA AAGCAAGATA GGCTATTAAG TGCAGAGGGA GAGAAAATGC CTCCAACATG   2400
TGAGGAAGTA ATGAGAGAAA TCATAGAATT TCTTCCGCTT CCTCGCTCAC TGACTCGCTG   2460
CGCTCGGTCG TTCGGCTGCG GCGAGCGGTA TCAGCTCACT CAAAGGCGGT AATACGGTTA   2520
TCCACAGAAT CAGGGGATAA CGCAGGAAAG AACATGTGAG CAAAAGGCCA GCAAAAGGCC   2580
```

-continued

```
AGGAACCGTA AAAAGGCCGC GTTGCTGGCG TTTTTCCATA GGCTCCGCCC CCCTGACGAG   2640

CATCACAAAA ATCGACGCTC AAGTCAGAGG TGGCGAAACC CGACAGGACT ATAAAGATAC   2700

CAGGCGTTTC CCCCTGGAAG CTCCCTCGTG CGCTCTCCTG TTCCGACCCT GCCGCTTACC   2760

GGATACCTGT CCGCCTTTCT CCCTTCGGGA AGCGTGGCGC TTTCTCAATG CTCACGCTGT   2820

AGGTATCTCA GTTCGGTGTA GGTCGTTCGC TCCAAGCTGG GCTGTGTGCA CGAACCCCCC   2880

GTTCAGCCCG ACCGCTGCGC CTTATCCGGT AACTATCGTC TTGAGTCCAA CCCGGTAAGA   2940

CACGACTTAT CGCCACTGGC AGCAGCCACT GGTAACAGGA TTAGCAGAGC GAGGTATGTA   3000

GGCGGTGCTA CAGAGTTCTT GAAGTGGTGG CCTAACTACG GCTACACTAG AAGGACAGTA   3060

TTTGGTATCT GCGCTCTGCT GAAGCCAGTT ACCTTCGGAA AAAGAGTTGG TAGCTCTTGA   3120

TCCGGCAAAC AAACCACCGC TGGTAGCGGT GGTTTTTTTG TTTGCAAGCA GCAGATTACG   3180

CGCAGAAAAA AAGGATCTCA AGAAGATCCT TTGATCTTTT CTACGGGGTC TGACGCTCAG   3240

TGGAACGAAA ACTCACGTTA AGGGATTTTG GTCATGAGAT TATCAAAAAG GATCTTCACC   3300

TAGATCCTTT TAAATTAAAA ATGAAGTTTT AAATCAATCT AAAGTATATA TGAGTAAACT   3360

TGGTCTGACA GTTACCAATG CTTAATCAGT GAGGCACCTA TCTCAGCGAT CTGTCTATTT   3420

CGTTCATCCA TAGTTGCCTG ACTCCCCGTC GTGTAGATAA CTACGATACG GGAGGGCTTA   3480

CCATCTGGCC CCAGTGCTGC AATGATACCG CGAGACCCAC GCTCACCGGC TCCAGATTTA   3540

TCAGCAATAA ACCAGCCAGC CGGAAGGGCC GAGCGCAGAA GTGGTCCTGC AACTTTATCC   3600

GCCTCCATCC AGTCTATTAA TTGTTGCCGG GAAGCTAGAG TAAGTAGTTC GCCAGTTAAT   3660

AGTTTGCGCA ACGTTGTTGC CATTGCTACA GGCATCGTGG TGTCACGCTC GTCGTTTGGT   3720

ATGGCTTCAT TCAGCTCCGG TTCCCAACGA TCAAGGCGAG TTACATGATC CCCCATGTTG   3780

TGCAAAAAAG CGGTTAGCTC CTTCGGTCCT CCGATCGTTG TCAGAAGTAA GTTGGCCGCA   3840

GTGTTATCAC TCATGGTTAT GGCAGCACTG CATAATTCTC TTACTGTCAT GCCATCCGTA   3900

AGATGCTTTT CTGTGACTGG TGAGTACTCA ACCAAGTCAT TCTGAGAATA GTGTATGCGG   3960

CGACCGAGTT GCTCTTGCCC GGCGTCAATA CGGGATAATA CCGCGCCACA TAGCAGAACT   4020

TTAAAAGTGC TCATCATTGG AAAACGTTCT TCGGGGCGAA AACTCTCAAG GATCTTACCG   4080

CTGTTGAGAT CCAGTTCGAT GTAACCCACT CGTGCACCCA ACTGATCTTC AGCATCTTTT   4140

ACTTTCACCA GCGTTTCTGG GTGAGCAAAA ACAGGAAGGC AAAATGCCGC AAAAAAGGGA   4200

ATAAGGGCGA CACGGAAATG TTGAATACTC ATACTCTTCC TTTTTCAATA TTATTGAAGC   4260

ATTTATCAGG GTTATTGTCT CATGAGCGGA TACATATTTG AATGTATTTA GAAAAATAAA   4320

CAAATAGGGG TTCCGCGCAC ATTTCCCCGA AAAGTGCCAC CTGACGTCTA AGAAACCATT   4380

ATTATCATGA CATTAACCTA TAAAAATAGG CGTATCACGA GGCCCTTTCG TC           4432
```

(2) INFORMATION FOR SEQ ID NO: 13:

(i) SEQUENCE CHARACTERISTICS:
(A) LENGTH: 2196 base pairs
(B) TYPE: nucleic acid
(C) STRANDEDNESS: double
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 13:

-continued

```
ATTGGCTATT GGCCATTGCA TACGTTGTAT CCATATCATA ATATGTACAT TTATATTGGC     60

TCATGTCCAA CATTACCGCC ATGTTGACAT TGATTATTGA CTAGTTATTA ATAGTAATCA    120

ATTACGGGGT CATTAGTTCA TAGCCCATAT ATGGAGTTCC GCGTTACATA ACTTACGGTA    180

AATGGCCCGC CTGGCTGACC GCCCAACGAC CCCCGCCCAT TGACGTCAAT AATGACGTAT    240

GTTCCCATAG TAACGCCAAT AGGGACTTTC CATTGACGTC AATGGGTGGA GTATTTACGG    300

TAAACTGCCC ACTTGGCAGT ACATCAAGTG TATCATATGC CAAGTACGCC CCCTATTGAC    360

GTCAATGACG GTAAATGGCC CGCCTGGCAT TATGCCCAGT ACATGACCTT ATGGGACTTT    420

CCTACTTGGC AGTACATCTA CGTATTAGTC ATCGCTATTA CCATGGTGAT GCGGTTTTGG    480

CAGTACATCA ATGGGCGTGG ATAGCGGTTT GACTCACGGG GATTTCCAAG TCTCCACCCC    540

ATTGACGTCA ATGGGAGTTT GTTTTGGCAC CAAAATCAAC GGGACTTTCC AAAATGTCGT    600

AACAACTCCG CCCCATTGAC GCAAATGGGC GGTAGGCGTG TACGGTGGGA GGTCTATATA    660

AGCAGAGCTC GTTTAGTGAA CCGTCAGATC GCCTGGAGAC GCCATCCACG CTGTTTTGAC    720

CTCCATAGAA GACACCGGGA CCGATCCAGC CTCCGCGGCC GGGAACGGTG CATTGGAACG    780

CGGATTCCCC GTGCCAAGAG TGACGTAAGT ACCGCCTATA GAGTCTATAG GCCCACCCCC    840

TTGGCTTCTT ATGCATGCTA TACTGTTTTT GGCTTGGGGT CTATACACCC CCGCTTCCTC    900

ATGTTATAGG TGATGGTATA GCTTAGCCTA TAGGTGTGGG TTATTGACCA TTATTGACCA    960

CTCCCCTATT GGTGACGATA CTTTCCATTA CTAATCCATA ACATGGCTCT TTGCCACAAC   1020

TCTCTTTATT GGCTATATGC CAATACACTG TCCTTCAGAG ACTGACACGG ACTCTGTATT   1080

TTTACAGGAT GGGGTCTCAT TTATTATTTA CAAATTCACA TATACAACAC CACCGTCCCC   1140

AGTGCCCGCA GTTTTTATTA AACATAACGT GGGATCTCCA CGCGAATCTC GGGTACGTGT   1200

TCCGGACATG GGCTCTTCTC CGGTAGCGGC GGAGCTTCTA CATCCGAGCC CTGCTCCCAT   1260

GCCTCCAGCG ACTCATGGTC GCTCGGCAGC TCCTTGCTCC TAACAGTGGA GGCCAGACTT   1320

AGGCACAGCA CGATGCCCAC CACCACCAGT GTGCCGCACA AGGCCGTGGC GGTAGGGTAT   1380

GTGTCTGAAA ATGAGCTCGG GGAGCGGGCT TGCACCGCTG ACGCATTTGG AAGACTTAAG   1440

GCAGCGGCAG AAGAAGATGC AGGCAGCTGA GTTGTTGTGT TCTGATAAGA GTCAGAGGTA   1500

ACTCCCGTTG CGGTGCTGTT AACGGTGGAG GGCAGTGTAG TCTGAGCAGT ACTCGTTGCT   1560

GCCGCGCGCG CCACCAGACA TAATAGCTGA CAGACTAACA GACTGTTCCT TTCCATGGGT   1620

CTTTTCTGCA GTCACCGTCC TTAGATCTGC TGTGCCTTCT AGTTGCCAGC CATCTGTTGT   1680

TTGCCCCTCC CCCGTGCCTT CCTTGACCCT GGAAGGTGCC ACTCCCACTG TCCTTTCCTA   1740

ATAAAATGAG GAAATTGCAT CGCATTGTCT GAGTAGGTGT CATTCTATTC TGGGGGGTGG   1800

GGTGGGGCAG CACAGCAAGG GGGAGGATTG GGAAGACAAT AGCAGGCATG CTGGGGATGC   1860

GGTGGGCTCT ATGGGTACCC AGGTGCTGAA GAATTGACCC GGTTCCTCCT GGGCCAGAAA   1920

GAAGCAGGCA CATCCCCTTC TCTGTGACAC ACCCTGTCCA CGCCCCTGGT TCTTAGTTCC   1980

AGCCCCACTC ATAGGACACT CATAGCTCAG GAGGGCTCCG CCTTCAATCC CACCCGCTAA   2040

AGTACTTGGA GCGGTCTCTC CCTCCCTCAT CAGCCCACCA AACCAAACCT AGCCTCCAAG   2100

AGTGGGAAGA AATTAAAGCA AGATAGGCTA TTAAGTGCAG AGGGAGAGAA AATGCCTCCA   2160

ACATGTGAGG AAGTAATGAG AGAAATCATA GAATTC                             2196
```

(2) INFORMATION FOR SEQ ID NO: 14:

(i) SEQUENCE CHARACTERISTICS:
(A) LENGTH: 4864 base pairs

-continued (B) TYPE: nucleic acid
(C) STRANDEDNESS: double
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 14:

```
TCGCGCGTTT CGGTGATGAC GGTGAAAACC TCTGACACAT GCAGCTCCCG GAGACGGTCA     60
CAGCTTGTCT GTAAGCGGAT GCCGGGAGCA GACAAGCCCG TCAGGGCGCG TCAGCGGGTG    120
TTGGCGGGTG TCGGGGCTGG CTTAACTATG CGGCATCAGA GCAGATTGTA CTGAGAGTGC    180
ACCATATGCG GTGTGAAATA CCGCACAGAT GCGTAAGGAG AAAATACCGC ATCAGATTGG    240
CTATTGGCCA TTGCATACGT TGTATCCATA TCATAATATG TACATTTATA TTGGCTCATG    300
TCCAACATTA CCGCCATGTT GACATTGATT ATTGACTAGT TATTAATAGT AATCAATTAC    360
GGGGTCATTA GTTCATAGCC CATATATGGA GTTCCGCGTT ACATAACTTA CGGTAAATGG    420
CCCGCCTGGC TGACCGCCCA ACGACCCCCG CCCATTGACG TCAATAATGA CGTATGTTCC    480
CATAGTAACG CCAATAGGGA CTTTCCATTG ACGTCAATGG GTGGAGTATT TACGGTAAAC    540
TGCCCACTTG GCAGTACATC AAGTGTATCA TATGCCAAGT ACGCCCCCTA TTGACGTCAA    600
TGACGGTAAA TGGCCCGCCT GGCATTATGC CCAGTACATG ACCTTATGGG ACTTTCCTAC    660
TTGGCAGTAC ATCTACGTAT TAGTCATCGC TATTACCATG GTGATGCGGT TTTGGCAGTA    720
CATCAATGGG CGTGGATAGC GGTTTGACTC ACGGGGATTT CCAAGTCTCC ACCCCATTGA    780
CGTCAATGGG AGTTTGTTTT GGCACCAAAA TCAACGGGAC TTTCCAAAAT GTCGTAACAA    840
CTCCGCCCCA TTGACGCAAA TGGGCGGTAG GCGTGTACGG TGGGAGGTCT ATATAAGCAG    900
AGCTCGTTTA GTGAACCGTC AGATCGCCTG GAGACGCCAT CCACGCTGTT TTGACCTCCA    960
TAGAAGACAC CGGGACCGAT CCAGCCTCCG CGGCCGGGAA CGGTGCATTG GAACGCGGAT   1020
TCCCCGTGCC AAGAGTGACG TAAGTACCGC CTATAGAGTC TATAGGCCCA CCCCCTTGGC   1080
TTCTTATGCA TGCTATACTG TTTTTGGCTT GGGGTCTATA CACCCCCGCT TCCTCATGTT   1140
ATAGGTGATG GTATAGCTTA GCCTATAGGT GTGGGTTATT GACCATTATT GACCACTCCC   1200
CTATTGGTGA CGATACTTTC CATTACTAAT CCATAACATG GCTCTTTGCC ACAACTCTCT   1260
TTATTGGCTA TATGCCAATA CACTGTCCTT CAGAGACTGA CACGGACTCT GTATTTTTAC   1320
AGGATGGGGT CTCATTTATT ATTTACAAAT TCACATATAC AACACCACCG TCCCCAGTGC   1380
CCGCAGTTTT TATTAAACAT AACGTGGGAT CTCCACGCGA ATCTCGGGTA CGTGTTCCGG   1440
ACATGGGCTC TTCTCCGGTA GCGGCGGAGC TTCTACATCC GAGCCCTGCT CCCATGCCTC   1500
CAGCGACTCA TGGTCGCTCG GCAGCTCCTT GCTCCTAACA GTGGAGGCCA GACTTAGGCA   1560
CAGCACGATG CCCACCACCA CCAGTGTGCC GCACAAGGCC GTGGCGGTAG GGTATGTGTC   1620
TGAAAATGAG CTCGGGGAGC GGGCTTGCAC CGCTGACGCA TTTGGAAGAC TTAAGGCAGC   1680
GGCAGAAGAA GATGCAGGCA GCTGAGTTGT TGTGTTCTGA TAAGAGTCAG AGGTAACTCC   1740
CGTTGCGGTG CTGTTAACGG TGGAGGGCAG TGTAGTCTGA GCAGTACTCG TTGCTGCCGC   1800
GCGCGCCACC AGACATAATA GCTGACAGAC TAACAGACTG TTCCTTTCCA TGGGTCTTTT   1860
CTGCAGTCAC CGTCCTTAGA TCTGCTGTGC CTTCTAGTTG CCAGCCATCT GTTGTTTGCC   1920
CCTCCCCCGT GCCTTCCTTG ACCCTGGAAG GTGCCACTCC CACTGTCCTT TCCTAATAAA   1980
ATGAGGAAAT TGCATCGCAT TGTCTGAGTA GGTGTCATTC TATTCTGGGG GGTGGGGTGG   2040
```

-continued

```
GGCAGCACAG CAAGGGGGAG GATTGGGAAG ACAATAGCAG GCATGCTGGG GATGCGGTGG   2100
GCTCTATGGG TACCCAGGTG CTGAAGAATT GACCCGGTTC CTCCTGGGCC AGAAAGAAGC   2160
AGGCACATCC CCTTCTCTGT GACACACCCT GTCCACGCCC CTGGTTCTTA GTTCCAGCCC   2220
CACTCATAGG ACACTCATAG CTCAGGAGGG CTCCGCCTTC AATCCCACCC GCTAAAGTAC   2280
TTGGAGCGGT CTCTCCCTCC CTCATCAGCC CACCAAACCA AACCTAGCCT CCAAGAGTGG   2340
GAAGAAATTA AAGCAAGATA GGCTATTAAG TGCAGAGGGA GAGAAAATGC CTCCAACATG   2400
TGAGGAAGTA ATGAGAGAAA TCATAGAATT TCTTCCGCTT CCTCGCTCAC TGACTCGCTG   2460
CGCTCGGTCG TTCGGCTGCG GCGAGCGGTA TCAGCTCACT CAAAGGCGGT AATACGGTTA   2520
TCCACAGAAT CAGGGGATAA CGCAGGAAAG AACATGTGAG CAAAAGGCCA GCAAAAGGCC   2580
AGGAACCGTA AAAAGGCCGC GTTGCTGGCG TTTTTCCATA GGCTCCGCCC CCCTGACGAG   2640
CATCACAAAA ATCGACGCTC AAGTCAGAGG TGGCGAAACC CGACAGGACT ATAAAGATAC   2700
CAGGCGTTTC CCCCTGGAAG CTCCCTCGTG CGCTCTCCTG TTCCGACCCT GCCGCTTACC   2760
GGATACCTGT CCGCCTTTCT CCCTTCGGGA AGCGTGGCGC TTTCTCAATG CTCACGCTGT   2820
AGGTATCTCA GTTCGGTGTA GGTCGTTCGC TCCAAGCTGG GCTGTGTGCA CGAACCCCCC   2880
GTTCAGCCCG ACCGCTGCGC CTTATCCGGT AACTATCGTC TTGAGTCCAA CCCGGTAAGA   2940
CACGACTTAT CGCCACTGGC AGCAGCCACT GGTAACAGGA TTAGCAGAGC GAGGTATGTA   3000
GGCGGTGCTA CAGAGTTCTT GAAGTGGTGG CCTAACTACG GCTACACTAG AAGGACAGTA   3060
TTTGGTATCT GCGCTCTGCT GAAGCCAGTT ACCTTCGGAA AAAGAGTTGG TAGCTCTTGA   3120
TCCGGCAAAC AAACCACCGC TGGTAGCGGT GGTTTTTTTG TTTGCAAGCA GCAGATTACG   3180
CGCAGAAAAA AAGGATCTCA AGAAGATCCT TTGATCTTTT CTACGGGGTC TGACGCTCAG   3240
TGGAACGAAA ACTCACGTTA AGGGATTTTG GTCATGAGAT TATCAAAAAG GATCTTCACC   3300
TAGATCCTTT TAAATTAAAA ATGAAGTTTT AAATCAATCT AAAGTATATA TGAGTAAACT   3360
TGGTCTGACA GTTACCAATG CTTAATCAGT GAGGCACCTA TCTCAGCGAT CTGTCTATTT   3420
CGTTCATCCA TAGTTGCCTG ACTCCGGGGG GGGGGGGCGC TGAGGTCTGC CTCGTGAAGA   3480
AGGTGTTGCT GACTCATACC AGGCCTGAAT CGCCCCATCA TCCAGCCAGA AAGTGAGGGA   3540
GCCACGGTTG ATGAGAGCTT TGTTGTAGGT GGACCAGTTG GTGATTTTGA ACTTTTGCTT   3600
TGCCACGGAA CGGTCTGCGT TGTCGGGAAG ATGCGTGATC TGATCCTTCA ACTCAGCAAA   3660
AGTTCGATTT ATTCAACAAA GCCGCCGTCC CGTCAAGTCA GCGTAATGCT CTGCCAGTGT   3720
TACAACCAAT TAACCAATTC TGATTAGAAA AACTCATCGA GCATCAAATG AAACTGCAAT   3780
TTATTCATAT CAGGATTATC AATACCATAT TTTTGAAAAA GCCGTTTCTG TAATGAAGGA   3840
GAAAACTCAC CGAGGCAGTT CCATAGGATG GCAAGATCCT GGTATCGGTC TGCGATTCCG   3900
ACTCGTCCAA CATCAATACA ACCTATTAAT TTCCCCTCGT CAAAAATAAG GTTATCAAGT   3960
GAGAAATCAC CATGAGTGAC GACTGAATCC GGTGAGAATG GCAAAAGCTT ATGCATTTCT   4020
TTCCAGACTT GTTCAACAGG CCAGCCATTA CGCTCGTCAT CAAAATCACT CGCATCAACC   4080
AAACCGTTAT TCATTCGTGA TTGCGCCTGA GCGAGACGAA ATACGCGATC GCTGTTAAAA   4140
GGACAATTAC AAACAGGAAT CGAATGCAAC CGGCGCAGGA ACACTGCCAG CGCATCAACA   4200
ATATTTTCAC CTGAATCAGG ATATTCTTCT AATACCTGGA ATGCTGTTTT CCCGGGGATC   4260
GCAGTGGTGA GTAACCATGC ATCATCAGGA GTACGGATAA AATGCTTGAT GGTCGGAAGA   4320
GGCATAAATT CCGTCAGCCA GTTTAGTCTG ACCATCTCAT CTGTAACATC ATTGGCAACG   4380
```

-continued

```
CTACCTTTGC CATGTTTCAG AAACAACTCT GGCGCATCGG GCTTCCCATA CAATCGATAG   4440

ATTGTCGCAC CTGATTGCCC GACATTATCG CGAGCCCATT TATACCCATA TAAATCAGCA   4500

TCCATGTTGG AATTTAATCG CGGCCTCGAG CAAGACGTTT CCCGTTGAAT ATGGCTCATA   4560

ACACCCCTTG TATTACTGTT TATGTAAGCA GACAGTTTTA TTGTTCATGA TGATATATTT   4620

TTATCTTGTG CAATGTAACA TCAGAGATTT TGAGACACAA CGTGGCTTTC CCCCCCCCCC   4680

CATTATTGAA GCATTTATCA GGGTTATTGT CTCATGAGCG GATACATATT TGAATGTATT   4740

TAGAAAAATA AACAAATAGG GGTTCCGCGC ACATTTCCCC GAAAAGTGCC ACCTGACGTC   4800

TAAGAAACCA TTATTATCAT GACATTAACC TATAAAAATA GGCGTATCAC GAGGCCCTTT   4860

CGTC                                                                4864
```

(2) INFORMATION FOR SEQ ID NO: 15:

(i) SEQUENCE CHARACTERISTICS:
(A) LENGTH: 41 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

```
CCACATAGAT CTGTTCCATG GTTGTGGCAA TATTATCATC G                         41
```

(2) INFORMATION FOR SEQ ID NO: 16:

(i) SEQUENCE CHARACTERISTICS:
(A) LENGTH: 39 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

```
GGTACAAGAT CTACCATGGC AGGAAGAAGC GGAGACAGC                            39
```

(2) INFORMATION FOR SEQ ID NO: 17:

(i) SEQUENCE CHARACTERISTICS:
(A) LENGTH: 43 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

```
CCACATAGAT CTGATATCGC ACTATTCTTT AGCTCCTGAC TCC                      43
```

(2) INFORMATION FOR SEQ ID NO: 18:

(i) SEQUENCE CHARACTERISTICS:

-continued (A) LENGTH: 78 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

GATCACCATG GATGCAATGA AGAGAGGGCT CTGCTGTGTG CTGCTGCTGT GTGGAGCAGT 60

CTTCGTTTCG CCCAGCGA 78

(2) INFORMATION FOR SEQ ID NO: 19:

(i) SEQUENCE CHARACTERISTICS:
(A) LENGTH: 78 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

GATCTCGCTG GGCGAAACGA AGACTGCTCC ACACAGCAGC AGCACACAGC AGAGCCCTCT 60

CTTCATTGCA TCCATGGT 78

(2) INFORMATION FOR SEQ ID NO: 20:

(i) SEQUENCE CHARACTERISTICS:
(A) LENGTH: 52 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

GGTACATGAT CAGATATCGC CCGGGCCGAG ATCTTCAGAC TTGGAGGAGG AG 52

(2) INFORMATION FOR SEQ ID NO: 21:

(i) SEQUENCE CHARACTERISTICS:
(A) LENGTH: 40 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 21:

CCACATTGAT CAGCTTGTGT AATTGTTAAT TTCTCTGTCC 40

(2) INFORMATION FOR SEQ ID NO: 22:

-continued (i) SEQUENCE CHARACTERISTICS:
(A) LENGTH: 39 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 22:

CCCCGGATCC TGATCACAGA AAAATTGTGG GTCACAGTC 39

(2) INFORMATION FOR SEQ ID NO: 23:

(i) SEQUENCE CHARACTERISTICS:
(A) LENGTH: 48 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 23:

CCCCAGGAAT CCACCTGTTA GCGCTTTTCT CTCTGCACCA CTCTTCTC 48

(2) INFORMATION FOR SEQ ID NO: 24:

(i) SEQUENCE CHARACTERISTICS:
(A) LENGTH: 35 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 24:

GGTACATGAT CACAGAAAAA TTGTGGGTCA CAGTC 35

(2) INFORMATION FOR SEQ ID NO: 25:

(i) SEQUENCE CHARACTERISTICS:
(A) LENGTH: 47 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 25:

CCACATTGAT CAGATATCTT ATCTTTTTTC TCTCTGCACC ACTCTTC 47

(2) INFORMATION FOR SEQ ID NO: 26:

(i) SEQUENCE CHARACTERISTICS:
(A) LENGTH: 38 base pairs
(B) TYPE: nucleic acid

-continued (C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 26:

GTCACCGTCC TCTATCAAAG CAGTAAGTAG TACATGCA 38

(2) INFORMATION FOR SEQ ID NO: 27:

(i) SEQUENCE CHARACTERISTICS:
(A) LENGTH: 38 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 27:

TGTACTACTT ACTGCTTTGA TAGAGGACGG TGACTGCA 38

(2) INFORMATION FOR SEQ ID NO: 28:

(i) SEQUENCE CHARACTERISTICS:
(A) LENGTH: 40 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 28:

GGTACATGAT CAACCATGAG AGTGAAGGAG AAATATCAGC 40

(2) INFORMATION FOR SEQ ID NO: 29:

(i) SEQUENCE CHARACTERISTICS:
(A) LENGTH: 43 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

CCACATTGAT CAGATATCCC CATCTTATAG CAAAATCCTT TCC 43

(2) INFORMATION FOR SEQ ID NO: 30:

(i) SEQUENCE CHARACTERISTICS:
(A) LENGTH: 43 base pairs
(B) TYPE: nucleic acid
(C) STRANDEDNESS: both
(D) TOPOLOGY: linear -continued (ii) MOLECULE TYPE: cDNA (iii) HYPOTHETICAL: NO (iv) ANTI-SENSE: NO (xi) SEQUENCE DESCRIPTION: SEQ ID NO: 30:

CCACATTGAT CAGATATCCC CATCTTATAG CAAAATCCTT TCC 43

(2) INFORMATION FOR SEQ ID NO: 31:

(i) SEQUENCE CHARACTERISTICS:
(A) LENGTH: 43 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 31:

GGTACACTGC AGTCACCGTC CTATGGCAGG AAGAAGCGGA GAC 43

(2) INFORMATION FOR SEQ ID NO: 32:

(i) SEQUENCE CHARACTERISTICS:
(A) LENGTH: 32 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 32:

CCACATCAGG TACCCCATAA TAGACTGTGA CC 32

(2) INFORMATION FOR SEQ ID NO: 33:

(i) SEQUENCE CHARACTERISTICS:
(A) LENGTH: 45 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

GGTACAAGAT CTACCATGGG ACCAGTACAA CAAATAGGTG GTAAC 45

(2) INFORMATION FOR SEQ ID NO: 34:

(i) SEQUENCE CHARACTERISTICS:
(A) LENGTH: 37 base pairs
(B) TYPE: nucleic acid
(C) STRANDEDNESS: both
(D) TOPOLOGY: linear (ii) MOLECULE TYPE: cDNA (iii) HYPOTHETICAL: NO -continued (iv) ANTI-SENSE: NO (xi) SEQUENCE DESCRIPTION: SEQ ID NO: 34:

CCACATAGAT CTTTACATTA ATCTAGCCTT CTGTCCC 37

(2) INFORMATION FOR SEQ ID NO: 35:

(i) SEQUENCE CHARACTERISTICS:
(A) LENGTH: 33 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 35:

GGTACAACCA TGGGTGGAGC TATTTCCATG AGG 33

(2) INFORMATION FOR SEQ ID NO: 36:

(i) SEQUENCE CHARACTERISTICS:
(A) LENGTH: 29 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 36:

CCTAGGTTAG CCTTCTTCTA ACCTCTTCC 29

(2) INFORMATION FOR SEQ ID NO: 37:

(i) SEQUENCE CHARACTERISTICS:
(A) LENGTH: 37 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 37:

GGTACAAGAT CTACCATGGG ATGTCTTGGG AATCAGC 37

(2) INFORMATION FOR SEQ ID NO: 38:

(i) SEQUENCE CHARACTERISTICS:
(A) LENGTH: 43 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO -continued (xi) SEQUENCE DESCRIPTION: SEQ ID NO: 38:

CCACATAGAT CTGATATCGT ATGAGTCTAC TGGAAATAAG AGG 43

(2) INFORMATION FOR SEQ ID NO: 39:

(i) SEQUENCE CHARACTERISTICS:
(A) LENGTH: 42 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 39:

GGTACAGGAT CCACCATGGG TGCGAGAGCG TCAGTATTAA GC 42

(2) INFORMATION FOR SEQ ID NO: 40:

(i) SEQUENCE CHARACTERISTICS:
(A) LENGTH: 50 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 40:

CCACATGGAT CCGCCCGGGC TTACATCTCT GTACAAATTT CTACTAATGC 50

(2) INFORMATION FOR SEQ ID NO: 41:

(i) SEQUENCE CHARACTERISTICS:
(A) LENGTH: 33 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 41:

GGTACAGGAT CCCCGCACGG CAAGAGGCGA GGG 33

(2) INFORMATION FOR SEQ ID NO: 42:

(i) SEQUENCE CHARACTERISTICS:
(A) LENGTH: 42 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 42:

GGTACAGGAT CCACCATGGC TGCGAGAGCG TCAGTATTAA GC 42

-continued (2) INFORMATION FOR SEQ ID NO: 43:

(i) SEQUENCE CHARACTERISTICS:
(A) LENGTH: 45 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 43:

CCACATGGAT CCGCCCGGGC CTTTATTGTG ACGAGGGGTC GTTGC 45

(2) INFORMATION FOR SEQ ID NO: 44:

(i) SEQUENCE CHARACTERISTICS:
(A) LENGTH: 33 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 44:

GGTACAGGAT CCCCGCACGG CAAGAGGCGA GGG 33

(2) INFORMATION FOR SEQ ID NO: 45:

(i) SEQUENCE CHARACTERISTICS:
(A) LENGTH: 42 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 45:

GGTACAGGAT CCACCATGGC TGCGAGAGCG TCAGTATTAA GC 42

(2) INFORMATION FOR SEQ ID NO: 46:

(i) SEQUENCE CHARACTERISTICS:
(A) LENGTH: 27 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 46:

GTACCTCATG AGCCACATAA TACCATG 27

(2) INFORMATION FOR SEQ ID NO: 47:

-continued (i) SEQUENCE CHARACTERISTICS:
(A) LENGTH: 40 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 47:

GGTACAAGAT CTACCATGGC TTGCAATTGT CAGTTGATGC 40

(2) INFORMATION FOR SEQ ID NO: 48:

(i) SEQUENCE CHARACTERISTICS:
(A) LENGTH: 42 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 48:

CCACATAGAT CTCCATGGGA ACTAAAGGAA GACGGTCTGT TC 42

(2) INFORMATION FOR SEQ ID NO: 49:

(i) SEQUENCE CHARACTERISTICS:
(A) LENGTH: 39 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 49:

GGTACAAGAT CTACCATGAA GGCAAACCTA CTGGTCCTG 39

(2) INFORMATION FOR SEQ ID NO: 50:

(i) SEQUENCE CHARACTERISTICS:
(A) LENGTH: 46 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 50:

CCACATAGAT CTGATATCCT AATCTCAGAT GCATATTCTG CACTGC 46

(2) INFORMATION FOR SEQ ID NO: 51:

(i) SEQUENCE CHARACTERISTICS:
(A) LENGTH: 15 amino acids

-continued (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 51:

```
Arg Ile His Ile Gly Pro Gly Arg Ala Phe Tyr Thr Thr Lys Asn
1               5                   10                  15
```

(2) INFORMATION FOR SEQ ID NO: 52:

(i) SEQUENCE CHARACTERISTICS:
(A) LENGTH: 26 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 52:

GAAAGAGCAG AAGACAGTGG CAATGA 26

(2) INFORMATION FOR SEQ ID NO: 53:

(i) SEQUENCE CHARACTERISTICS:
(A) LENGTH: 40 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 53:

GGGCTTTGCT AAATGGGTGG CAAGTGGCCC GGGCATGTGG 40

(2) INFORMATION FOR SEQ ID NO: 54:

(i) SEQUENCE CHARACTERISTICS:
(A) LENGTH: 23 base pairs
(B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 54:

CTAACAGACT GTTCCTTTCC ATG 23

(2) INFORMATION FOR SEQ ID NO: 55:

(i) SEQUENCE CHARACTERISTICS:
(A) LENGTH: 18 base pairs

-continued (B) TYPE: nucleic acid
(C) STRANDEDNESS: both
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 55:

GGAGTGGCAC CTTCCAGG 18

(2) INFORMATION FOR SEQ ID NO: 56:

(i) SEQUENCE CHARACTERISTICS:
(A) LENGTH: 45 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 56:

GGAGACAGCG ACGAAGACCT CCTCAAGGCA GTCAGACTCA TCAAG 45

(2) INFORMATION FOR SEQ ID NO: 57:

(i) SEQUENCE CHARACTERISTICS:
(A) LENGTH: 71 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 57:

GATGGCTGGC AACTAGAAGG CACAGCAGAT CTGATATCGC ACTATTCTTT AGCTCCTGAC 60

TCCAATATTG T 71

(2) INFORMATION FOR SEQ ID NO: 58:

(i) SEQUENCE CHARACTERISTICS:
(A) LENGTH: 119 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 58:

CTTAGATCAA CCATGAGAGT GAAGGAGAAA TATCAGCACT TGTGGAGATG GGGGTGGAGA 60

TGGGGCACCA TGCTCCTTGG GATGTTGATG ATCTGTAGTG CTACAGAAAA ATTGTGGGT 119

(2) INFORMATION FOR SEQ ID NO: 59:

(i) SEQUENCE CHARACTERISTICS:

-continued (A) LENGTH: 78 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 59:

CTGGCAACTA GAAGGCACAG CAGATCAGAT AGTGTCCCCA TCTTATAGCA AAATCCTTTC 60

CAAGCCCTGT CTTATTCT 78

(2) INFORMATION FOR SEQ ID NO: 60:

(i) SEQUENCE CHARACTERISTICS:
(A) LENGTH: 19 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 60:

GATTTAGGTG ACACTATAG 19

(2) INFORMATION FOR SEQ ID NO: 61:

(i) SEQUENCE CHARACTERISTICS:
(A) LENGTH: 20 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 61:

TAATACGACT CACTATAGGG 20

(2) INFORMATION FOR SEQ ID NO: 62:

(i) SEQUENCE CHARACTERISTICS:
(A) LENGTH: 28 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 62:

CATGCCTGCA GGTCGACTCT AAATTCCG 28

(2) INFORMATION FOR SEQ ID NO: 63:

(i) SEQUENCE CHARACTERISTICS:
(A) LENGTH: 37 base pairs

-continued (B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 63:

ACCCGGGGAT CCTCTAGCGC GCTTGTCTCT TGTTCCA 37

(2) INFORMATION FOR SEQ ID NO: 64:

(i) SEQUENCE CHARACTERISTICS:
(A) LENGTH: 15 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 64:

GGGACGTGGT TTTCC 15

(2) INFORMATION FOR SEQ ID NO: 65:

(i) SEQUENCE CHARACTERISTICS:
(A) LENGTH: 66 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 65:

TATGGCCACA ACCATGGCAG GAAGAAGCGG AGACAGCGAC GAAGACCTCC TCAAGGCAGT 60

CAGACT 66

(2) INFORMATION FOR SEQ ID NO: 66:

(i) SEQUENCE CHARACTERISTICS:
(A) LENGTH: 90 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 66:

CTCGAGCCAT GGGCCCCTAG ACTATAGCGT GATAAGAAAT CGAGGACTGA GGTTATAACA 60

TCCTCTAAGG TGGTTATAAA CTCCCGAAGG 90

(2) INFORMATION FOR SEQ ID NO: 67:

(i) SEQUENCE CHARACTERISTICS:

-continued (A) LENGTH: 16 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 67:

GCTTCGGCCA GTAACG 16

(2) INFORMATION FOR SEQ ID NO: 68:

(i) SEQUENCE CHARACTERISTICS:
(A) LENGTH: 87 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 68:

TTGCATGCCT GCAGGTGGTA CATGATCAGA TATCGCCCGG GCCGAGATCT TCAGACTTGG 60

AGGAGGAGAT ATGAGGGACA ATTGGAG 87

(2) INFORMATION FOR SEQ ID NO: 69:

(i) SEQUENCE CHARACTERISTICS:
(A) LENGTH: 79 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 69:

GGGGCGGAAT TTAGAGTCAA TTGATCAGCT TGTGTAATTG TTAATTTCTC TGTCCCACTC 60

CATCCAGGTC GTGTGATTC 79

(2) INFORMATION FOR SEQ ID NO: 70:

(i) SEQUENCE CHARACTERISTICS:
(A) LENGTH: 18 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 70:

CCATCTCCAC AAGTGCTG 18

(2) INFORMATION FOR SEQ ID NO: 71:

-continued (i) SEQUENCE CHARACTERISTICS:
(A) LENGTH: 77 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 71:

AGATCTAAGG ACGGTGACTG CATGTACTAC TTACTGCTTT GATAGAGGAC GGTGACTGCA 60

GAAAAGACCC ATGGAAA 77

(2) INFORMATION FOR SEQ ID NO: 72:

(i) SEQUENCE CHARACTERISTICS:
(A) LENGTH: 16 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 72:

GCTTCGGCCA GTAACG 16

(2) INFORMATION FOR SEQ ID NO: 73:

(i) SEQUENCE CHARACTERISTICS:
(A) LENGTH: 62 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 73:

GGCACAGCAG ATCAGATGGG GATCTGATAT CGCACTATTC TTTAGCTCCT GACTCCTGAC 60

TC 62

(2) INFORMATION FOR SEQ ID NO: 74:

(i) SEQUENCE CHARACTERISTICS:
(A) LENGTH: 42 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 74:

GGAATTTGAG TCATCCCCAT CTTATAGCAA AATCCTTTCC AA 42

(2) INFORMATION FOR SEQ ID NO: 75:

-continued (i) SEQUENCE CHARACTERISTICS:
(A) LENGTH: 42 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 75:

CTTAGATCCC CGCACGGCAA GAGGCGAGGG GCGGCGACTG GT 42

(2) INFORMATION FOR SEQ ID NO: 76:

(i) SEQUENCE CHARACTERISTICS:
(A) LENGTH: 70 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 76:

GGCACAGCAG ATCCGCCCGG GCTTACATCT CTGTACAAAT TTCTACTAAT GCTTTTATTT 60

TTCTTCTGTC 70

(2) INFORMATION FOR SEQ ID NO: 77:

(i) SEQUENCE CHARACTERISTICS:
(A) LENGTH: 70 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 77:

CTTAGATCCA CCATGGGTGC GAGAGCGTCA GTATTAAGCG GGGGAGAAT TAGATCGATG 60

GGAAAAAATT 70

(2) INFORMATION FOR SEQ ID NO: 78:

(i) SEQUENCE CHARACTERISTICS:
(A) LENGTH: 70 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 78:

GGCACAGCAG ATCCGCCCGG GCTTACATCT CTGTACAAAT TTCTACTAAT GCTTTTATTT 60

TTCTTCTGTC 70

-continued (2) INFORMATION FOR SEQ ID NO: 79:

(i) SEQUENCE CHARACTERISTICS:
(A) LENGTH: 118 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 79:

TCACCGTCCT TAGATCACCA TGGATGCAAT GAAGAGAGGG CTCTGCTGTG TGCTGCTGCT 60

GTGTGGAGCA GTCTTCGTTT CGCCCAGCGA GATCTGCTGT GCCTTCTAGT TGCCAGCC 118

(2) INFORMATION FOR SEQ ID NO: 80:

(i) SEQUENCE CHARACTERISTICS:
(A) LENGTH: 43 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 80:

TTCGTTTCGC CCAGCGATCA CAGAAAAATT GTGGGTCACA GTC 43

(2) INFORMATION FOR SEQ ID NO: 81:

(i) SEQUENCE CHARACTERISTICS:
(A) LENGTH: 43 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 81:

GGCACAGCAG ATCCACGTGT TAGCGCTTTT CTCTCTCCAC CAC 43

(2) INFORMATION FOR SEQ ID NO: 82:

(i) SEQUENCE CHARACTERISTICS:
(A) LENGTH: 80 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 82:

TCACCGTCCT TAGATCTACC ATGGGACCAG TACAACAAAT AGGTGGTAAC TATGTCCACC 60

-continued

TGCCATTAAG CCCGAGAACA 80

(2) INFORMATION FOR SEQ ID NO: 83:

(i) SEQUENCE CHARACTERISTICS:
(A) LENGTH: 44 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 83:

GGCACAGCAG ATCTTTACAT TAATCTAGCC TTCTGTCCCG GTCC 44

(2) INFORMATION FOR SEQ ID NO: 84:

(i) SEQUENCE CHARACTERISTICS:
(A) LENGTH: 80 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 84:

TCACCGTCCT TAGATCGGTA CAACCATGGG TGGAGCTATT TCCATGAGGC AATCCAAGCC 60

GGCTGGAGAT CTGACAGAAA 80

(2) INFORMATION FOR SEQ ID NO: 85:

(i) SEQUENCE CHARACTERISTICS:
(A) LENGTH: 85 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 85:

GGCACAGCAG ATCACCTAGG TTAGCCTTCT TCTAACCTCT TCCTCTGACA GGCCTGACTT 60

GCTTCCAACT CTTCTGGGTA TCTAG 85

(2) INFORMATION FOR SEQ ID NO: 86:

(i) SEQUENCE CHARACTERISTICS:
(A) LENGTH: 90 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 86:

-continued

ACCGTCCTTA GATTCGACAT AGCAGAATAG GCGTTACTCG ACAGAGGAGA GCAAGAAATG 60

GAGCCAGTAG ATCCTAGACT AGAGCCCTGG 90

(2) INFORMATION FOR SEQ ID NO: 87:

(i) SEQUENCE CHARACTERISTICS:
(A) LENGTH: 41 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 87:

GGCACAGCAG ATCCGAGATG CTGCTCCCAC CCCATCTGCT G 41

(2) INFORMATION FOR SEQ ID NO: 88:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 88:

Lys Gln Ile Ile Asn Met Trp Gln Glu Val Gly Lys Ala Met Tyr Ala
1 5 10 15

(2) INFORMATION FOR SEQ ID NO: 89:

(i) SEQUENCE CHARACTERISTICS:
(A) LENGTH: 13 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 89:

His Glu Asp Ile Ile Ser Leu Trp Asp Gln Ser Leu Lys
1 5 10

(2) INFORMATION FOR SEQ ID NO: 90:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide -continued (iii) HYPOTHETICAL: NO (iv) ANTI-SENSE: NO (v) FRAGMENT TYPE: internal (xi) SEQUENCE DESCRIPTION: SEQ ID NO: 90:

```
Asp Arg Val Ile Glu Val Val Gln Gly Xaa Tyr Arg Ala Ile Arg
1               5                   10                  15
```

(2) INFORMATION FOR SEQ ID NO: 91:

(i) SEQUENCE CHARACTERISTICS:
(A) LENGTH: 33 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 91:

```
GGTACAAATA TTGGCTATTG GCCATTGCAT ACG                                33
```

(2) INFORMATION FOR SEQ ID NO: 92:

(i) SEQUENCE CHARACTERISTICS:
(A) LENGTH: 36 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 92:

```
CCACATCTCG AGGAACCGGG TCAATTCTTC AGCACC                             36
```

(2) INFORMATION FOR SEQ ID NO: 93:

(i) SEQUENCE CHARACTERISTICS:
(A) LENGTH: 38 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 93:

```
GGTACAGATA TCGGAAAGCC ACGTTGTGTC TCAAAATC                           38
```

(2) INFORMATION FOR SEQ ID NO: 94:

(i) SEQUENCE CHARACTERISTICS:
(A) LENGTH: 37 base pairs
(B) TYPE: nucleic acid
(C) STRANDEDNESS: both
(D) TOPOLOGY: both (ii) MOLECULE TYPE: cDNA -continued (iii) HYPOTHETICAL: NO (iv) ANTI-SENSE: NO (xi) SEQUENCE DESCRIPTION: SEQ ID NO: 94:

CCACATGGAT CCGTAATGCT CTGCCAGTGT TACAACC 37

(2) INFORMATION FOR SEQ ID NO: 95:

(i) SEQUENCE CHARACTERISTICS:
(A) LENGTH: 39 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 95:

GGTACATGAT CACGTAGAAA AGATCAAAGG ATCTTCTTG 39

(2) INFORMATION FOR SEQ ID NO: 96:

(i) SEQUENCE CHARACTERISTICS:
(A) LENGTH: 35 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 96:

CCACATGTCG ACCCGTAAAA AGGCCGCGTT GCTGG 35

(2) INFORMATION FOR SEQ ID NO: 97:

(i) SEQUENCE CHARACTERISTICS:
(A) LENGTH: 18 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 97:

GAGCCAATAT AAATGTAC 18

(2) INFORMATION FOR SEQ ID NO: 98:

(i) SEQUENCE CHARACTERISTICS:
(A) LENGTH: 15 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO -continued (xi) SEQUENCE DESCRIPTION: SEQ ID NO: 98:

CAATAGCAGG CATGC 15

(2) INFORMATION FOR SEQ ID NO: 99:

(i) SEQUENCE CHARACTERISTICS:
(A) LENGTH: 16 base pairs
(B) TYPE: nucleic acid
(C) STRANDEDNESS: both
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 99:

GCAAGCAGCA GATTAC 16

(2) INFORMATION FOR SEQ ID NO: 100:

(i) SEQUENCE CHARACTERISTICS:
(A) LENGTH: 3547 base pairs
(B) TYPE: nucleic acid
(C) STRANDEDNESS: double
(D) TOPOLOGY: both (ii) MOLECULE TYPE: cDNA (iii) HYPOTHETICAL: NO (iv) ANTI-SENSE: NO (xi) SEQUENCE DESCRIPTION: SEQ ID NO: 100:

GATATTGGCT ATTGGCCATT GCATACGTTG TATCCATATC ATAATATGTA CATTTATATT 60

GGCTCATGTC CAACATTACC GCCATGTTGA CATTGATTAT TGACTAGTTA TTAATAGTAA 120

TCAATTACGG GGTCATTAGT TCATAGCCCA TATATGGAGT TCCGCGTTAC ATAACTTACG 180

GTAAATGGCC CGCCTGGCTG ACCGCCCAAC GACCCCCGCC CATTGACGTC AATAATGACG 240

TATGTTCCCA TAGTAACGCC AATAGGGACT TTCCATTGAC GTCAATGGGT GGAGTATTTA 300

CGGTAAACTG CCCACTTGGC AGTACATCAA GTGTATCATA TGCCAAGTAC GCCCCCTATT 360

GACGTCAATG ACGGTAAATG GCCCGCCTGG CATTATGCCC AGTACATGAC CTTATGGGAC 420

TTTCCTACTT GGCAGTACAT CTACGTATTA GTCATCGCTA TTACCATGGT GATGCGGTTT 480

TGGCAGTACA TCAATGGGCG TGGATAGCGG TTTGACTCAC GGGGATTTCC AAGTCTCCAC 540

CCCATTGACG TCAATGGGAG TTTGTTTTGG CACCAAAATC AACGGGACTT TCCAAAATGT 600

CGTAACAACT CCGCCCCATT GACGCAAATG GGCGGTAGGC GTGTACGGTG GGAGGTCTAT 660

ATAAGCAGAG CTCGTTTAGT GAACCGTCAG ATCGCCTGGA GACGCCATCC ACGCTGTTTT 720

GACCTCCATA GAAGACACCG GGACCGATCC AGCCTCCGCG GCCGGGAACG GTGCATTGGA 780

ACGCGGATTC CCCGTGCCAA GAGTGACGTA AGTACCGCCT ATAGAGTCTA TAGGCCCACC 840

CCCTTGGCTT CTTATGCATG CTATACTGTT TTTGGCTTGG GGTCTATACA CCCCCGCTTC 900

CTCATGTTAT AGGTGATGGT ATAGCTTAGC CTATAGGTGT GGGTTATTGA CCATTATTGA 960

CCACTCCCCT ATTGGTGACG ATACTTTCCA TTACTAATCC ATAACATGGC TCTTTGCCAC 1020

AACTCTCTTT ATTGGCTATA TGCCAATACA CTGTCCTTCA GAGACTGACA CGGACTCTGT 1080

ATTTTTACAG GATGGGGTCT CATTTATTAT TTACAAATTC ACATATACAA CACCACCGTC 1140

-continued

```
CCCAGTGCCC GCAGTTTTTA TTAAACATAA CGTGGGATCT CCACGCGAAT CTCGGGTACG   1200
TGTTCCGGAC ATGGGCTCTT CTCCGGTAGC GGCGGAGCTT CTACATCCGA GCCCTGCTCC   1260
CATGCCTCCA GCGACTCATG GTCGCTCGGC AGCTCCTTGC TCCTAACAGT GGAGGCCAGA   1320
CTTAGGCACA GCACGATGCC CACCACCACC AGTGTGCCGC ACAAGGCCGT GGCGGTAGGG   1380
TATGTGTCTG AAAATGAGCT CGGGGAGCGG GCTTGCACCG CTGACGCATT TGGAAGACTT   1440
AAGGCAGCGG CAGAAGAAGA TGCAGGCAGC TGAGTTGTTG TGTTCTGATA AGAGTCAGAG   1500
GTAACTCCCG TTGCGGTGCT GTTAACGGTG GAGGGCAGTG TAGTCTGAGC AGTACTCGTT   1560
GCTGCCGCGC GCGCCACCAG ACATAATAGC TGACAGACTA ACAGACTGTT CCTTTCCATG   1620
GGTCTTTTCT GCAGTCACCG TCCTTAGATC TGCTGTGCCT TCTAGTTGCC AGCCATCTGT   1680
TGTTTGCCCC TCCCCCGTGC CTTCCTTGAC CCTGGAAGGT GCCACTCCCA CTGTCCTTTC   1740
CTAATAAAAT GAGGAAATTG CATCGCATTG TCTGAGTAGG TGTCATTCTA TTCTGGGGGG   1800
TGGGGTGGGG CAGCACAGCA AGGGGGAGGA TTGGGAAGAC AATAGCAGGC ATGCTGGGGA   1860
TGCGGTGGGC TCTATGGGTA CGGCCGCAGC GGCCGTACCC AGGTGCTGAA GAATTGACCC   1920
GGTTCCTCGA CCCGTAAAAA GGCCGCGTTG CTGGCGTTTT TCCATAGGCT CCGCCCCCCT   1980
GACGAGCATC ACAAAAATCG ACGCTCAAGT CAGAGGTGGC GAAACCCGAC AGGACTATAA   2040
AGATACCAGG CGTTTCCCCC TGGAAGCTCC CTCGTGCGCT CTCCTGTTCC GACCCTGCCG   2100
CTTACCGGAT ACCTGTCCGC CTTTCTCCCT TCGGGAAGCG TGGCGCTTTC TCAATGCTCA   2160
CGCTGTAGGT ATCTCAGTTC GGTGTAGGTC GTTCGCTCCA AGCTGGGCTG TGTGCACGAA   2220
CCCCCCGTTC AGCCCGACCG CTGCGCCTTA TCCGGTAACT ATCGTCTTGA GTCCAACCCG   2280
GTAAGACACG ACTTATCGCC ACTGGCAGCA GCCACTGGTA ACAGGATTAG CAGAGCGAGG   2340
TATGTAGGCG GTGCTACAGA GTTCTTGAAG TGGTGGCCTA ACTACGGCTA CACTAGAAGG   2400
ACAGTATTTG GTATCTGCGC TCTGCTGAAG CCAGTTACCT TCGGAAAAAG AGTTGGTAGC   2460
TCTTGATCCG GCAAACAAAC CACCGCTGGT AGCGGTGGTT TTTTTGTTTG CAAGCAGCAG   2520
ATTACGCGCA GAAAAAAAGG ATCTCAAGAA GATCCTTTGA TCTTTTCTAC GTGATCCCGT   2580
AATGCTCTGC CAGTGTTACA ACCAATTAAC CAATTCTGAT TAGAAAAACT CATCGAGCAT   2640
CAAATGAAAC TGCAATTTAT TCATATCAGG ATTATCAATA CCATATTTTT GAAAAAGCCG   2700
TTTCTGTAAT GAAGGAGAAA ACTCACCGAG GCAGTTCCAT AGGATGGCAA GATCCTGGTA   2760
TCGGTCTGCG ATTCCGACTC GTCCAACATC AATACAACCT ATTAATTTCC CCTCGTCAAA   2820
AATAAGGTTA TCAAGTGAGA AATCACCATG AGTGACGACT GAATCCGGTG AGAATGGCAA   2880
AAGCTTATGC ATTTCTTTCC AGACTTGTTC AACAGGCCAG CCATTACGCT CGTCATCAAA   2940
ATCACTCGCA TCAACCAAAC CGTTATTCAT TCGTGATTGC GCCTGAGCGA GACGAAATAC   3000
GCGATCGCTG TTAAAAGGAC AATTACAAAC AGGAATCGAA TGCAACCGGC GCAGGAACAC   3060
TGCCAGCGCA TCAACAATAT TTTCACCTGA ATCAGGATAT TCTTCTAATA CCTGGAATGC   3120
TGTTTTCCCG GGGATCGCAG TGGTGAGTAA CCATGCATCA TCAGGAGTAC GGATAAAATG   3180
CTTGATGGTC GGAAGAGGCA TAAATTCCGT CAGCCAGTTT AGTCTGACCA TCTCATCTGT   3240
AACATCATTG GCAACGCTAC CTTTGCCATG TTTCAGAAAC AACTCTGGCG CATCGGGCTT   3300
CCCATACAAT CGATAGATTG TCGCACCTGA TTGCCCGACA TTATCGCGAG CCCATTTATA   3360
CCCATATAAA TCAGCATCCA TGTTGGAATT TAATCGCGGC CTCGAGCAAG ACGTTTCCCG   3420
TTGAATATGG CTCATAACAC CCCTTGTATT ACTGTTTATG TAAGCAGACA GTTTTATTGT   3480
```

-continued

```
TCATGATGAT ATATTTTTAT CTTGTGCAAT GTAACATCAG AGATTTTGAG ACACAACGTG   3540

GCTTTCC                                                             3547
```